(12) United States Patent
D'Agostino et al.

(10) Patent No.: US 11,207,109 B2
(45) Date of Patent: Dec. 28, 2021

(54) METHOD AND APPARATUS FOR TREATING BONE FRACTURES, AND/OR FOR FORTIFYING AND/OR AUGMENTING BONE, INCLUDING THE PROVISION AND USE OF COMPOSITE IMPLANTS, AND NOVEL COMPOSITE STRUCTURES WHICH MAY BE USED FOR MEDICAL AND NON-MEDICAL APPLICATIONS

(71) Applicant: 206 ORTHO, Inc., Deerfield, NH (US)

(72) Inventors: Jeffrey A. D'Agostino, Deerfield, NH (US); Robert S. Whitehouse, Lexington, MA (US); Arthur Watterson, Nashua, NH (US); Werner Blank, Wilton, CT (US); Charles Hegedus, Allentown, PA (US); Sandip Agarwal, Arlington, MA (US); Elizabeth Nelson, Wellesley, MA (US)

(73) Assignee: 206 ORTHO, INC., Deerfield, NH (US)

( * ) Notice: Subject to any disclaimer, the term of this patent is extended or adjusted under 35 U.S.C. 154(b) by 0 days.

(21) Appl. No.: 16/672,206

(22) Filed: Nov. 1, 2019

(65) Prior Publication Data

US 2020/0305936 A1  Oct. 1, 2020

Related U.S. Application Data

(63) Continuation-in-part of application No. 16/657,610, filed on Oct. 18, 2019, which is a continuation of
(Continued)

(51) Int. Cl.
*A61B 17/72* (2006.01)
*A61F 2/28* (2006.01)
(Continued)

(52) U.S. Cl.
CPC .......... *A61B 17/72* (2013.01); *A61B 17/7097* (2013.01); *A61B 17/7275* (2013.01);
(Continued)

(58) Field of Classification Search
CPC .............. A61B 17/7097; A61B 17/164; A61B 17/7095; A61B 17/72; A61B 17/8852;
(Continued)

(56) References Cited

U.S. PATENT DOCUMENTS 534,293 A 2/1895 Stevens
2,902,462 A 9/1959 Harry et al.
(Continued)

FOREIGN PATENT DOCUMENTS

EP 0656215 6/1995
EP 0677297 10/1995
(Continued)

OTHER PUBLICATIONS

Arif Iftekhar (Biomedical Composites, Chap 12, 12.1 to 12.17, 2004). (Year: 2004).*
(Continued)

*Primary Examiner* — Blessing M Fubara
(74) *Attorney, Agent, or Firm* — The Dobrusin Law Firm, P.C.

(57) ABSTRACT

A composite comprising: a barrier, said barrier being configured to selectively pass water, and said barrier being degradable in the presence of water; a matrix material for disposition within said barrier, wherein said matrix material has a flowable state and a set state, and wherein said matrix material is degradable in the presence of water; and at least one reinforcing element for disposition within said barrier and integration with said matrix material, wherein said at least one reinforcing element is degradable in the presence of water, and further wherein, upon the degradation of said
(Continued)

at least one reinforcing element in the presence of water, provides an agent for modulating the degradation rate of said matrix material in the presence of water.

45 Claims, 39 Drawing Sheets

Related U.S. Application Data application No. 16/040,164, filed on Jul. 19, 2018, now Pat. No. 10,517,654, which is a continuation of application No. 15/138,578, filed on Apr. 26, 2016, now Pat. No. 10,028,776, which is a continuation of application No. 13/781,473, filed on Feb. 28, 2013, now Pat. No. 9,320,601, which is a continuation-in-part of application No. 13/452,273, filed on Apr. 20, 2012, now abandoned, which is a continuation-in-part of application No. PCT/US2011/057124, filed on Oct. 20, 2011, said application No. 16/657,610 is a continuation-in-part of application No. 15/156,782, filed on May 17, 2016, now Pat. No. 10,857,261, which is a continuation of application No. 14/193,619, filed on Feb. 28, 2014, now abandoned, which is a continuation of application No. 13/452,273, filed on Apr. 20, 2012, now abandoned, which is a continuation-in-part of application No. PCT/US2011/057124, filed on Oct. 20, 2011, said application No. 16/657,610 is a continuation-in-part of application No. 16/025,639, filed on Jul. 2, 2018, which is a continuation of application No. 14/893,441, filed as application No. PCT/US2014/039394 on May 23, 2014, now Pat. No. 10,010,609, said application No. 16/025,639 is a continuation-in-part of application No. 15/138,578, filed on Apr. 26, 2016, now Pat. No. 10,028,776, which is a continuation of application No. 13/781,473, filed on Feb. 28, 2013, now Pat. No. 9,320,601, which is a continuation-in-part of application No. 13/452,273, filed on Apr. 20, 2012, now abandoned, which is a continuation-in-part of application No. PCT/US2011/057124, filed on Oct. 20, 2011, said application No. 16/657,610 is a continuation-in-part of application No. 15/106,754, filed as application No. PCT/US2014/071572 on Dec. 19, 2014, now Pat. No. 10,525,168, and a continuation-in-part of application No. PCT/US2014/039394, filed on May 23, 2014, said application No. 15/106,754 is a continuation-in-part of application No. 13/781,473, filed on Feb. 28, 2013, now Pat. No. 9,320,601, which is a continuation-in-part of application No. 13/452,273, filed on Apr. 20, 2012, now abandoned, which is a continuation-in-part of application No. PCT/US2011/057124, filed on Oct. 20, 2011, said application No. 16/657,610 is a continuation-in-part of application No. PCT/US2019/031617, filed on May 9, 2019, and a continuation-in-part of application No. 15/309,663, filed as application No. PCT/US2015/030017 on May 8, 2015, now Pat. No. 10,525,169, which is a continuation-in-part of application No. PCT/US2014/071572, filed on Dec. 19, 2014, and a continuation-in-part of application No. PCT/US2014/039394, filed on May 23, 2014, said application No. PCT/US2015/030017 is a continuation-in-part of application No. PCT/US2014/039394, filed on May 23, 2014, said application No. 15/309,663 is a continuation-in-part of application No. 13/781,473, filed on Feb. 28, 2013, now Pat. No. 9,320,601, which is a continuation-in-part of application No. 13/452,273, filed on Apr. 20, 2012, now abandoned, which is a continuation-in-part of application No. PCT/US2011/057124, filed on Oct. 20, 2011, said application No. 16/657,610 is a continuation-in-part of application No. 16/349,086, filed as application No. PCT/US2017/061398 on Nov. 13, 2017, now Pat. No. 11,058,796, which is a continuation-in-part of application No. 15/156,782, filed on May 17, 2016, now Pat. No. 10,857,261, which is a continuation of application No. 14/193,619, filed on Feb. 28, 2014, now abandoned, which is a continuation of application No. 13/452,273, filed on Apr. 20, 2012, now abandoned, which is a continuation-in-part of application No. PCT/US2011/057124, filed on Oct. 20, 2011, said application No. 16/349,086 is a continuation-in-part of application No. 16/040,164, filed on Jul. 19, 2018, now Pat. No. 10,517,654, which is a continuation of application No. 15/138,578, filed on Apr. 26, 2016, now Pat. No. 10,028,776, which is a continuation of application No. 13/781,473, filed on Feb. 28, 2013, now Pat. No. 9,320,601, which is a continuation-in-part of application No. 13/452,273, filed on Apr. 20, 2012, now abandoned, which is a continuation-in-part of application No. PCT/US2011/057124, filed on Oct. 20, 2011, said application No. 16/349,086 is a continuation-in-part of application No. 16/025,637, filed on Jul. 2, 2018, which is a continuation of application No. 14/893,441, filed as application No. PCT/US2014/039394 on May 23, 2014, now Pat. No. 10,010,609, said application No. 16/025,639 is a continuation-in-part of application No. 15/138,578, filed on Apr. 26, 2016, now Pat. No. 10,028,776, which is a continuation of application No. 13/781,473, filed on Feb. 28, 2013, now Pat. No. 9,320,601, which is a continuation-in-part of application No. 13/452,273, filed on Apr. 20, 2012, now abandoned, which is a continuation-in-part of application No. PCT/US2011/057124, filed on Oct. 20, 2011, said application No. 16/349,086 is a continuation-in-part of application No. 15/106,754, filed as application No. PCT/US2014/071572 on Dec. 19, 2014, now Pat. No. 10,525,168, and a continuation-in-part of application No. PCT/US2014/039394, filed on May 23, 2014, said application No. 15/106,754 is a continuation-in-part of application No. 13/781,473, filed on Feb. 28, 2013, now Pat. No. 9,320,601, which is a continuation-in-part of application No. 13/452,273, filed on Apr. 20, 2012, now abandoned, which is a continuation-in-part of application No. PCT/US2011/057124, filed on Oct. 20, 2011, said application No. 16/349,086 is a continuation-in-part of application No. PCT/US2019/031617, filed on May 9, 2019, and a continuation-in-part of application No. 15/309,663, filed as application No. PCT/US2015/030017 on May 8, 2015, now Pat. No. 10,525,169, which is a continuation-in-part of application No. PCT/US2014/071572, filed on Dec. 19, 2014, and a continuation-in-part of application No. PCT/US2014/039394, filed on May 23, 2014, said application No. PCT/US2015/030017 is a continuation-in-part of application No. PCT/US2014/039394, filed on May 23, 2014, said application No. 15/309,663 is a continuation-in-part of application No. 13/781,473, filed on Feb. 28, 2013, now Pat. No. 9,320,601, which is a continuation-in-part of application No. 13/452,273, filed on Apr. 20, 2012, now abandoned, which is a continuation-in-part of application No. PCT/US2011/057124, filed on Oct. 20, 2011, application No. 16/672,206, which is a continuation of application No. 15/309,663, filed as application No. PCT/US2015/030017 on May 8, 2015, now Pat. No. 10,525,169, which is a continuation-in-part of application No. PCT/US2014/071572, filed on Dec. 19, 2014, which is a continuation-in-part of application No. PCT/US2014/039394, filed on May 23, 2014, said application No. 15/309,663 is a continuation-in-part of application No. 13/781,473, filed on Feb. 28, 2013, now Pat. No. 9,320,601, which is a continuation-in-part of application No. 13/452,273, filed on Apr. 20, 2012, now abandoned, which is a continuation-in-part of application No. PCT/US2011/057124, filed on Oct. 20, 2011.

(60) Provisional application No. 61/394,968, filed on Oct. 20, 2010, provisional application No. 61/604,632, filed on Feb. 29, 2012, provisional application No. 61/826,983, filed on May 23, 2013, provisional application No. 61/826,994, filed on May 23, 2013, provisional application No. 61/828,463, filed on May 29, 2013, provisional application No. 61/883,062, filed on Sep. 26, 2013, provisional application No. 61/394,968, filed on Oct. 20, 2010, provisional application No. 61/918,088, filed on Dec. 19, 2013, provisional application No. 61/944,629, filed on Feb. 26, 2014, provisional application No. 61/944,634, filed on Feb. 26, 2014, provisional application No. 61/944,636, filed on Feb. 26, 2014, provisional application No. 61/944,640, filed on Feb. 26, 2014, provisional application No. 61/944,644, filed on Feb. 26, 2014, provisional application No. 61/944,649, filed on Feb. 26, 2014, provisional application No. 61/990,464, filed on May 8, 2014, provisional application No. 62/059,059, filed on Oct. 2, 2014, provisional application No. 62/420,429, filed on Nov. 10, 2016, provisional application No. 62/669,271, filed on May 9, 2018.

(51) Int. Cl.
*A61B 17/70* (2006.01)
*A61K 9/00* (2006.01)
*A61K 47/34* (2017.01)
*A61B 17/00* (2006.01)

(52) U.S. Cl.
CPC .............. *A61F 2/28* (2013.01); *A61K 9/0024* (2013.01); *A61K 47/34* (2013.01); *A61B 2017/00004* (2013.01); *A61B 2017/00867* (2013.01); *A61B 2017/00964* (2013.01); *Y10T 428/13* (2015.01); *Y10T 428/249924* (2015.04); *Y10T 428/2915* (2015.01); *Y10T 428/2936* (2015.01); *Y10T 428/2971* (2015.01); *Y10T 442/2033* (2015.04)

(58) Field of Classification Search
CPC ............ A61B 17/8805; A61B 17/7275; A61B 2017/00938; A61B 2017/00867; A61B 2017/00004; A61B 2017/00964; A61F 2/28; A61F 2/2846; A61F 2002/2835; A61L 27/50; A61L 31/129; A61L 27/00; A61L 31/14; A61L 31/128; A61L 27/443; A61L 27/48; A61L 31/126; A61L 27/446; A61L 2400/06; A61L 2430/02; A61K 47/34; A61K 9/0024; Y10T 428/2915; Y10T 442/2033; Y10T 428/2971; Y10T 428/249924; Y10T 428/2936; Y10T 428/13

See application file for complete search history.

(56) References Cited

U.S. PATENT DOCUMENTS

| | | |
|---|---|---|
| 2,951,823 A | 9/1960 | Hubert |
| 2,961,374 A | 11/1960 | Hans et al. |
| 3,830,750 A | 8/1974 | Wellman |
| 4,241,537 A | 12/1980 | Wood |
| 4,356,228 A | 10/1982 | Kobayashi et al. |
| 4,645,503 A | 2/1987 | Lin et al. |
| 4,653,487 A | 3/1987 | Maale |
| 4,843,112 A | 6/1989 | Gerhart et al. |
| 4,916,193 A | 4/1990 | Tang et al. |
| 4,919,679 A | 4/1990 | Averill et al. |
| 4,955,911 A | 9/1990 | Frey et al. |
| 4,993,410 A | 2/1991 | Kimsey |
| 5,010,145 A | 4/1991 | Ikada et al. |
| 5,026,373 A | 6/1991 | Ray et al. |
| 5,047,054 A | 9/1991 | Vijayan et al. |
| 5,064,427 A | 11/1991 | Burkinshaw |
| 5,126,170 A | 6/1992 | Zwiener et al. |
| 5,175,199 A | 12/1992 | Asano et al. |
| 5,190,549 A | 3/1993 | Miller et al. |
| 5,190,550 A | 3/1993 | Miller et al. |
| 5,236,741 A | 8/1993 | Zwiener et al. |
| 5,243,012 A | 9/1993 | Wicks et al. |
| 5,336,699 A | 8/1994 | Cooke et al. |
| 5,352,230 A | 10/1994 | Hood |
| 5,362,834 A | 11/1994 | Schapel et al. |
| 5,401,693 A | 3/1995 | Bauer et al. |
| 5,409,492 A | 4/1995 | Jones et al. |
| 5,443,471 A | 8/1995 | Swajger |
| 5,458,641 A | 10/1995 | Jimenez |
| 5,476,466 A | 12/1995 | Barrette et al. |
| 5,489,704 A | 2/1996 | Squiller et al. |
| 5,501,706 A | 3/1996 | Arenberg |
| 5,514,136 A | 5/1996 | Richelsoph |
| 5,514,137 A | 5/1996 | Coutts |
| 5,516,873 A | 5/1996 | Hicks et al. |
| 5,549,679 A | 8/1996 | Kuslich |
| 5,580,945 A | 12/1996 | Wade et al. |
| 5,591,453 A | 1/1997 | Ducheyne et al. |
| 5,597,930 A | 1/1997 | Wicks et al. |
| 5,623,045 A | 4/1997 | Zwiener et al. |
| 5,633,389 A | 5/1997 | Jonsson et al. |
| 5,644,049 A | 7/1997 | Giusti et al. |
| 5,681,872 A | 10/1997 | Erbe |
| 5,683,395 A | 11/1997 | Miktiail |
| 5,725,580 A | 3/1998 | Cloutier et al. |
| 5,739,176 A | 4/1998 | Dunn et al. |
| 5,785,642 A | 7/1998 | Wallace et al. |
| 5,821,326 A | 10/1998 | Kurek et al. |
| 5,827,289 A | 10/1998 | Reiley et al. |
| 5,847,195 A | 12/1998 | Roesler |
| 5,849,015 A | 12/1998 | Hayl |
| 5,852,203 A | 12/1998 | Jonsson et al. |
| 5,863,551 A | 1/1999 | Woerly |
| 5,899,907 A | 5/1999 | Johnson |
| 5,916,585 A | 6/1999 | Cook et al. |
| 5,951,564 A | 9/1999 | Schroder et al. |
| 5,989,259 A | 11/1999 | Penenberg et al. |
| 6,027,742 A | 2/2000 | Lee et al. |
| 6,086,556 A | 7/2000 | Hamilton et al. |
| 6,107,436 A | 8/2000 | Goeb et al. |
| 6,110,179 A | 8/2000 | Flivik et al. |
| 6,113,605 A | 9/2000 | Storer |
| 6,127,597 A | 10/2000 | Beyar et al. |
| 6,139,963 A | 10/2000 | Fujii et al. |
| 6,165,177 A | 12/2000 | Wilson et al. |
| 6,168,777 B1 | 1/2001 | Greff et al. |
| 6,183,870 B1 | 2/2001 | Hergenrother et al. |
| 6,228,092 B1 | 5/2001 | Mikhail |

(56) References Cited

U.S. PATENT DOCUMENTS

| | | | |
|---|---|---|---|
| 6,238,435 B1 | 5/2001 | Meulink et al. |
| 6,270,502 B1 | 8/2001 | Stulberg |
| 6,274,164 B1 | 8/2001 | Novich |
| 6,306,243 B1 | 10/2001 | Clark et al. |
| 6,355,829 B2 | 3/2002 | Roesler et al. |
| 6,447,514 B1 | 9/2002 | Stalcup et al. |
| 6,511,748 B1 | 1/2003 | Barrows |
| 6,521,736 B2 | 2/2003 | Watterson et al. |
| 6,524,327 B1 | 2/2003 | Spacek |
| 6,530,958 B1 | 3/2003 | Cima et al. |
| 6,548,002 B2 | 4/2003 | Gresser et al. |
| 6,602,293 B1 | 8/2003 | Biermann et al. |
| 6,626,913 B1 | 9/2003 | McKinnon et al. |
| 6,679,890 B2 | 1/2004 | Margulies et al. |
| 6,884,264 B2 | 4/2005 | Spiegelberg et al. |
| 6,962,963 B2 | 11/2005 | Kumar et al. |
| 7,037,311 B2 | 5/2006 | Parkinson et al. |
| 7,255,712 B1 | 8/2007 | Steinberg |
| 7,368,503 B2 | 5/2008 | Hale |
| 7,494,491 B2 | 2/2009 | Fankhauser et al. |
| 7,517,539 B1 | 4/2009 | Lee et al. |
| 7,682,335 B2 | 3/2010 | Pepper et al. |
| 7,708,979 B2 | 5/2010 | Lowman et al. |
| 7,754,782 B2 | 7/2010 | Heckroth et al. |
| 7,781,038 B2 | 8/2010 | Hamilton et al. |
| 7,806,900 B2 | 10/2010 | Rabiner |
| 7,879,107 B2 | 2/2011 | Tate et al. |
| 7,964,206 B2 | 6/2011 | Suokas et al. |
| 8,007,498 B2 | 8/2011 | Mische |
| 8,128,626 B2 | 3/2012 | Justin |
| 8,137,777 B2 | 3/2012 | Chen |
| 8,147,492 B2 | 4/2012 | Justin et al. |
| 8,162,943 B2 | 4/2012 | Justin et al. |
| 8,167,881 B2 | 5/2012 | Justin |
| 8,246,371 B2 | 8/2012 | Emerson |
| 8,246,628 B2 | 8/2012 | Rabiner |
| 8,348,956 B2 | 1/2013 | Rabiner |
| 8,366,711 B2 | 2/2013 | Rabiner et al. |
| 8,492,484 B2 | 7/2013 | Lorenz |
| 8,497,342 B2 | 7/2013 | Chen et al. |
| 8,512,338 B2 | 8/2013 | Rabiner et al. |
| 8,524,856 B2 | 9/2013 | Krishnaswamy et al. |
| 8,546,456 B2 | 10/2013 | Rose et al. |
| 8,722,783 B2 | 5/2014 | Rose et al. |
| 8,834,468 B2 | 9/2014 | Justin |
| 8,870,965 B2 | 10/2014 | Rabiner et al. |
| 8,912,149 B1 | 12/2014 | Rawat et al. |
| 9,320,601 B2 | 4/2016 | D'Agostino et al. |
| 9,381,277 B2 | 7/2016 | Lehtonen et al. |
| 9,492,210 B2 | 11/2016 | Rains et al. |
| 10,010,609 B2 | 7/2018 | D'Agostino et al. |
| 10,028,776 B2 | 7/2018 | D'Agostino et al. |
| 2002/0150604 A1 | 10/2002 | Yi et al. |
| 2003/0044467 A1 | 3/2003 | Brodbeck et al. |
| 2003/0114552 A1 | 6/2003 | Schacht |
| 2004/0010261 A1 | 1/2004 | Hoag et al. |
| 2004/0010262 A1 | 1/2004 | Parkinson et al. |
| 2004/0028655 A1 | 2/2004 | Nelson et al. |
| 2004/0078090 A1 | 4/2004 | Binette et al. |
| 2004/0082954 A1 | 4/2004 | Teitelbaum et al. |
| 2004/0220672 A1 | 11/2004 | Shadduck |
| 2004/0221615 A1 | 11/2004 | Postupack et al. |
| 2004/0230309 A1 | 11/2004 | Dimauro et al. |
| 2004/0242722 A1 | 12/2004 | Rose et al. |
| 2004/0265355 A1 | 12/2004 | Shalaby |
| 2005/0010231 A1 | 1/2005 | Myers |
| 2005/0055094 A1 | 3/2005 | Kuslich |
| 2005/0081750 A1 | 4/2005 | Xu et al. |
| 2005/0136764 A1 | 6/2005 | Sherman et al. |
| 2005/0142163 A1 | 6/2005 | Hunter |
| 2005/0208094 A1 | 9/2005 | Armitage et al. |
| 2005/0233062 A1 | 10/2005 | Hossainy et al. |
| 2006/0064164 A1 | 3/2006 | Thelen et al. |
| 2006/0009513 A1 | 5/2006 | Truckai et al. |
| 2006/0100174 A1 | 5/2006 | Hu et al. |
| 2006/0141101 A1 | 6/2006 | Chen et al. |
| 2006/0184250 A1 | 8/2006 | Bandoh et al. |
| 2006/0200150 A1 | 9/2006 | Tlomaki et al. |
| 2006/0208393 A1 | 9/2006 | Karmaker et al. |
| 2007/0059281 A1 | 3/2007 | Moseley et al. |
| 2007/0191963 A1 | 8/2007 | Winterbottom |
| 2007/0208134 A1 | 9/2007 | Hunter |
| 2007/0255422 A1 | 11/2007 | Wei et al. |
| 2008/0004628 A1 | 1/2008 | White |
| 2008/0051797 A1 | 2/2008 | Surrna et al. |
| 2008/0160259 A1 | 7/2008 | Nielson et al. |
| 2008/0172061 A1 | 7/2008 | Ragbir |
| 2008/0206716 A1 | 8/2008 | Asgary |
| 2008/0221576 A1 | 9/2008 | Keller |
| 2008/0228284 A1 | 9/2008 | Fritz et al. |
| 2008/0255560 A1* | 10/2008 | Myers ............... A61B 17/7225 606/63 |
| 2009/0099267 A1 | 4/2009 | Kumar et al. |
| 2009/0148487 A1 | 6/2009 | Siedler |
| 2009/0182425 A1 | 7/2009 | Duda et al. |
| 2009/0204196 A1 | 8/2009 | Weber |
| 2010/0076503 A1 | 3/2010 | Beyar et al. |
| 2010/0099779 A1 | 4/2010 | Hnojewyj et al. |
| 2010/0137491 A1 | 6/2010 | Rose et al. |
| 2010/0168798 A1 | 7/2010 | Clineff et al. |
| 2010/0248260 A1 | 9/2010 | Ban et al. |
| 2010/0318085 A1 | 12/2010 | Austin et al. |
| 2010/0330260 A1 | 12/2010 | McKay |
| 2010/0331850 A1 | 12/2010 | Rabiner |
| 2011/0013958 A1 | 1/2011 | Shona et al. |
| 2011/0045069 A1 | 2/2011 | Ley |
| 2011/0066252 A1 | 3/2011 | Hanssen et al. |
| 2011/0159071 A1 | 6/2011 | Cool et al. |
| 2011/0184115 A1 | 7/2011 | Debras et al. |
| 2011/0184530 A1 | 7/2011 | Datta et al. |
| 2011/0189414 A1 | 8/2011 | Whitehouse |
| 2011/0218646 A1* | 9/2011 | Pertici ............... A61L 27/44 623/23.56 |
| 2011/0237704 A1 | 9/2011 | Guelcher et al. |
| 2011/0244017 A1 | 10/2011 | Kleiner et al. |
| 2012/0028047 A1 | 2/2012 | Imai et al. |
| 2012/0029102 A1* | 2/2012 | Rose ............... A61F 2/2846 521/88 |
| 2012/0040002 A1 | 2/2012 | Letitonen et al. |
| 2012/0048769 A1 | 3/2012 | Sivik et al. |
| 2012/0059376 A1 | 3/2012 | Rains et al. |
| 2012/0095463 A1 | 4/2012 | Rains et al. |
| 2012/0101593 A1 | 4/2012 | D'Agostino et al. |
| 2012/0149844 A1 | 6/2012 | Whitehouse |
| 2012/0203264 A1 | 8/2012 | Karwa et al. |
| 2012/0238523 A1 | 9/2012 | Cool et al. |
| 2012/0263797 A1 | 10/2012 | D'Agostino et al. |
| 2012/0310368 A1 | 12/2012 | Voisard et al. |
| 2012/0315225 A1 | 12/2012 | Porbeni et al. |
| 2013/0045249 A1 | 2/2013 | Cool et al. |
| 2013/0065046 A1 | 3/2013 | Krishnaswamy |
| 2013/0071443 A1 | 3/2013 | Cool et al. |
| 2013/0101593 A1 | 4/2013 | Keler et al. |
| 2013/0171397 A1 | 7/2013 | Ghost et al. |
| 2013/0219965 A1 | 8/2013 | Allan et al. |
| 2013/0233545 A1 | 9/2013 | Mahoney et al. |
| 2013/0253661 A1 | 9/2013 | D'Agostino et al. |
| 2013/0323468 A1 | 12/2013 | Myers et al. |
| 2014/0030536 A1 | 1/2014 | Krishnaswamy |
| 2014/0046454 A1 | 2/2014 | Rose et al. |
| 2014/0079789 A1 | 3/2014 | Pomrink et al. |
| 2014/0127500 A1 | 5/2014 | Carberry et al. |
| 2014/0178328 A1 | 6/2014 | D'Agostino et al. |
| 2014/0235754 A1 | 8/2014 | Rose et al. |
| 2015/0328251 A1 | 11/2015 | Cool et al. |
| 2016/0346435 A1 | 12/2016 | D'Agostino et al. |

FOREIGN PATENT DOCUMENTS

| | | |
|---|---|---|
| EP | 0927214 | 7/2007 |
| EP | 2223707 | 9/2010 |
| WO | 89/00431 | 1/1989 |
| WO | 92/20738 | 11/1992 |
| WO | 98/19617 | 5/1998 |

(56) References Cited

FOREIGN PATENT DOCUMENTS

| WO | 01/64139 | 9/2001 |
|---|---|---|
| WO | 2004/073563 | 9/2004 |
| WO | 2004/103208 | 12/2004 |
| WO | 2005/112804 | 12/2005 |
| WO | 2007/082186 | 7/2007 |
| WO | 2008/067531 | 6/2008 |
| WO | 2008/096363 | 8/2008 |
| WO | 2010/011943 | 1/2010 |
| WO | 2010/122098 | 10/2010 |
| WO | 2011/071453 | 6/2011 |
| WO | 2013/012731 | 1/2013 |
| WO | 2013/130877 | 9/2013 |
| WO | 2013/184822 | 12/2013 |
| WO | 2013/184836 | 12/2013 |
| WO | 2014/028943 | 2/2014 |
| WO | 2014/190289 | 11/2014 |
| WO | 2015/172101 | 11/2015 |
| WO | 2015/175682 | 11/2015 |
| WO | 2016/035088 | 3/2016 |
| WO | 2016/035089 | 3/2016 |
| WO | 2016/103049 | 6/2016 |
| WO | 2017/155956 | 9/2017 |
| WO | 2018/002917 | 1/2018 |

OTHER PUBLICATIONS

Baravarian et al., Advancements in Bone Fixation Utilizing Novel Biointegrative Fixation Technology, Clin Podiatr Med Surg, 2018, vol. 35, pp. 53-62.
Bibekananda, D. et al., Biodegradable Hyperbranced Epoxy From Castor Oil-Based Hyperbranched Polyester Polyoi, ACS Sustainabie Chemistry & Engineering, Mar. 2014, vol. 2, No. 3, pp. 445-453.
Chen et al., Comparison of biodegradable and metallic tension-band fixation for patella fractures: 38 patients followed for 2 years, Acta Orthopaedica Scandinavica, 1998.
Dow Answer Center, Dow Polyurethanes—Prepolymer Definition, Oracle, 2014.
Feng, X. et al., Overview of Advances in Sugar-Based Polymers, Polymers for Advanced Technologies, Nov. 10, 2010, vol. 22, pp. 139-150.
http://v1Avw.iflscience.com/health-and-medicine/new-drug-delivery-system-co uld-replace-injections.
http://wernerblank.com/equat/ViSCTEMP3.htm.
http://wernerblank.com/polyur/chemistry/isocyanate/isocyanat_overview.htm.
https://bonnieplants.com/growing/growing-cauliflower.
https://en,wikipediaorg/wiki/Fracture_toughness.
J.-W. Rhim et al., Bio-Nanocomposites for Food Packaging Applications, Progress in Polymer Science, 2013, vol. 38, pp. 1629-1652.
M. Barry et al., Flexible Intramedullary Nails for Fractures in Children, Journal of Bone & Joint Surgery, 2004, pp. 947-950.
M. L. Williams et al., The Temperature Dependence of Relaxation Mechanisms in Amorphous Polymers and Other Glass-Forming Liquids, Journal of the American Chemical Society, 195 5, vol. 7 7, p. 370-,-3707.
Middleton et al., Synthetic biodegradable polymers as orthopedic devices, Biomaterials, 2000.
R Shogren, Water Vapor Permeability of Biodegradable Polymers, Journal of Environmental Polymer Degradation, 1997, vol. 5, No. 2, pp. 91-95.
Soluble Silicates, OECD SIDS, Apr. 2004.
T. Hirvikorpi et al., Enhanced Water Vapor Barrier Properties for Biopolymer Films by Polyelectrolyte Multilayer and Atomic Layer Deposited Al2O3 Double-Coating. Applied Surface Science, 2011, vol. 257, No. 22, pp. 9451-9454.

\* cited by examiner

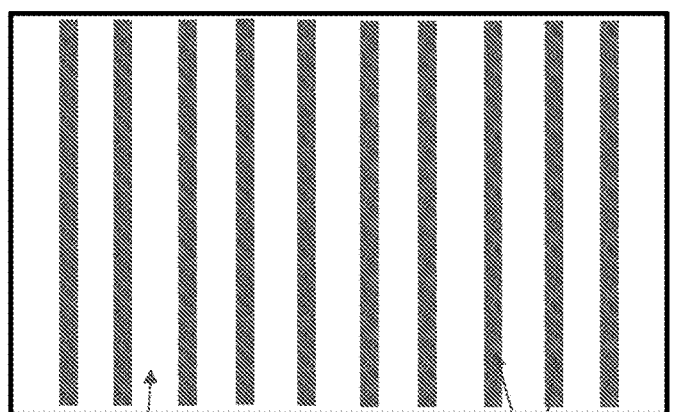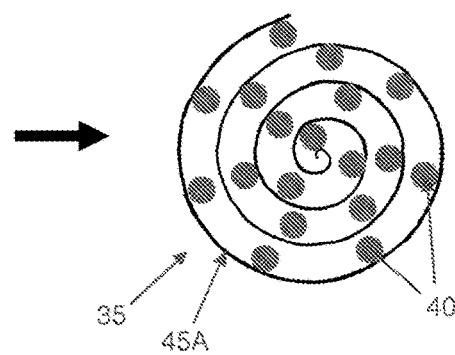

METHOD AND APPARATUS FOR TREATING BONE FRACTURES, AND/OR FOR FORTIFYING AND/OR AUGMENTING BONE, INCLUDING THE PROVISION AND USE OF COMPOSITE IMPLANTS, AND NOVEL COMPOSITE STRUCTURES WHICH MAY BE USED FOR MEDICAL AND NON-MEDICAL APPLICATIONS

REFERENCE TO PENDING PRIOR PATENT APPLICATIONS

This patent application:
(1) is a continuation-in-part of pending prior International (PCT) Patent Application No. PCT/US14/71572, filed Dec. 19, 2014 by 206 ORTHO, Inc. for METHOD AND APPARATUS FOR TREATING BONE FRACTURES, AND/OR FOR FORTIFYING AND/OR AUGMENTING BONE, INCLUDING THE PROVISION AND USE OF COMPOSITE IMPLANTS, AND NOVEL COMPOSITE STRUCTURES WHICH MAY BE USED FOR MEDICAL AND NON-MEDICAL APPLICATIONS, which patent application:
 (A) is a continuation-in-part of pending prior International (PCT) Patent Application No. PCT/US14/39394, filed May 23, 2014 by 206 ORTHO, Inc. for METHOD AND APPARATUS FOR TREATING BONE FRACTURES, AND/OR FOR FORTIFYING AND/OR AUGMENTING BONE, INCLUDING THE PROVISION AND USE OF COMPOSITE IMPLANTS, which patent application:
  (i) is a continuation-in-part of pending prior U.S. patent application Ser. No. 13/781,473, filed Feb. 28, 2013 by Jeffrey A. D'Agostino et al. for METHOD AND APPARATUS FOR TREATING BONE FRACTURES, AND/OR FOR FORTIFYING AND/OR AUGMENTING BONE, INCLUDING THE PROVISION AND USE OF COMPOSITE IMPLANTS, which patent application:
   (a) is a continuation-in-part of prior U.S. patent application Ser. No. 13/452,273, filed Apr. 20, 2012 by Jeffrey A. D'Agostino et al. for IMPLANTABLE POLYMER FOR BONE AND VASCULAR LESIONS, which patent application in turn (1) is a continuation-in-part of prior International (PCT) Patent Application No. PCT/US2011/057124, filed Oct. 20, 2011, and (2) claims benefit of prior U.S. Provisional Patent Application Ser. No. 61/394,968, filed Oct. 20, 2010; and
   (b) claims benefit of prior U.S. Provisional Patent Application Ser. No. 61/604,632, filed Feb. 29, 2012 by Jeffrey D'Agostino et al. for SPLINT INJECTION;
  (ii) claims benefit of prior U.S. Provisional Patent Application Ser. No. 61/826,983, filed May 23, 2013 by Jeffrey D'Agostino et al. for METHOD AND APPARATUS FOR TREATING BONE FRACTURES, AND/OR FOR FORTIFYING AND/OR AUGMENTING BONE, INCLUDING THE PROVISION AND USE OF COMPOSITE IMPLANTS INCLUDING THERMOPLASTICS;
  (iii) claims benefit of prior U.S. Provisional Patent Application Ser. No. 61/826,994, filed May 23, 2013 by Jeffrey D'Agostino et al. for METHOD AND APPARATUS FOR TREATING BONE FRACTURES, AND/OR FOR FORTIFYING AND/OR AUGMENTING BONE, INCLUDING THE PROVISION AND USE OF COMPOSITE IMPLANTS INCLUDING URETHANES;
  (iv) claims benefit of prior U.S. Provisional Patent Application Ser. No. 61/828,463, filed May 29, 2013 by Jeffrey A. D'Agostino et al. for METHOD AND APPARATUS FOR TREATING BONE FRACTURES, AND/OR FOR FORTIFYING AND/OR AUGMENTING BONE, INCLUDING THE PROVISION AND USE OF COMPOSITE IMPLANTS; and
  (v) claims benefit of prior U.S. Provisional Patent Application Ser. No. 61/883,062, filed Sep. 26, 2013 by 206 ORTHO, Inc. and Jeffrey A. D'Agostino et al. for METHOD AND APPARATUS FOR TREATING BONE FRACTURES, AND/OR FOR FORTIFYING AND/OR AUGMENTING BONE, INCLUDING THE PROVISION AND USE OF COMPOSITE IMPLANTS;
 (B) claims benefit of prior U.S. Provisional Patent Application Ser. No. 61/918,088, filed Dec. 19, 2013 by 206 ORTHO, Inc. and Robert S. Whitehouse et al. for BIORESORBABLE AND BIODEGRADEABLE COMPOSITE MATERIALS; and
 (C) claims benefit of prior U.S. Provisional Patent Application Ser. No. 61/944,629, filed Feb. 26, 2014 by 206 ORTHO, Inc. and Robert S. Whitehouse for NOVEL BALLOON FOR MEDICAL IMPLANTS;
(2) claims benefit of pending prior U.S. Provisional Patent Application Ser. No. 61/990,464, filed May 8, 2014 by 206 ORTHO, Inc. and Jeffrey A. D'Agostino et al. for METHODS AND COMPOSITIONS FOR PREDICTABLY CONTROLLING THE ONSET AND RATE OF MATERIAL DEGREDATION; and
(3) claims benefit of pending prior U.S. Provisional Patent Application Ser. No. 62/059,059, filed Oct. 2, 2014 by 206 ORTHO, Inc. and Arthur Watterson et al. for HIGH PERFORMANCE BIODEGRADABLE MATERIAL WITH TUNABLE DURATION PROPERTIES.

The fifteen (15) above-identified patent applications are hereby incorporated herein by reference.

FIELD OF THE INVENTION

This invention relates to methods and apparatus for treating bones, and more particularly to methods and apparatus for treating bone fractures and/or for fortifying and/or augmenting bone in mammals, and relates to novel composite structures which may be used for medical and non-medical applications.

BACKGROUND OF THE INVENTION

It is common for bones to become fractured as the result of a fall, an automobile accident, a sporting injury, etc. In these circumstances, it is common to reinforce the bone in the area of the fracture so as to support the bone during healing.

To this end, current treatment options typically comprise external stabilizers (e.g., plaster casts, braces, etc.) and internal stabilizers (e.g., screws, bone plates, intramedullary nails, etc.).

External stabilizers such as casts and external braces suffer from a number of disadvantages. For one thing, they can interfere with a patient's normal daily activities, e.g., it can be difficult to wear clothing over a cast, or to operate a motor vehicle with a cast, etc. Furthermore, with animals, external casting and bracing of some fractures can be extremely difficult. In addition, with external stabilizers, the soft tissue interposed between the bone and the external stabilizer is used to transmit load from the bone to the external stabilizer. As a result, shortly after application of the external stabilizer, the patient's intervening soft tissue will begin to atrophy through disuse, thereby requiring further rehabilitation for the patient. Furthermore, as the intervening soft tissue atrophies, the close supporting fit of the external stabilizer is disrupted and, as a result, effective load transfer is undermined.

Internal stabilizers such as pins, screws, bone plates, intramedullary nails, etc. generally provide a more effective stabilization of the fracture, since they are able to directly interface with the bone. However, installing these internal stabilizers requires an invasive surgical procedure, e.g., a relatively large incision, etc. Furthermore, after healing of the fracture, the internal stabilizers (screws, bone plates, intramedullary nails, etc.) should, ideally, be removed so as to allow the bone to fully recover its mechanical strength. This, however, requires a second surgical procedure, with additional trauma to the patient.

In some circumstances (e.g., such as with fractures in vertebral bodies), bone cements may be injected into the interior of the bone in an attempt to stabilize the bone. However, such bone cements suffer from disadvantages of their own. More particularly, such bone cements are typically ceramic cements, polymer-based cements (e.g., polymethyl methacrylate, also known as PMMA) or calcium salt-based cements. While these bone cements are typically capable of withstanding significant compressive loading, they are also extremely brittle and typically cannot withstand significant tensile loading. This limits their application in instances where the loading on the bone may include a tensile component. This means that bone cements are not suitable for use in many situations, particularly in long bones (e.g., the tibia). Additionally, the failure mode for brittle materials results in catastrophic failure that includes the creation of shards of material which are difficult to remove and create potential dangers for the anatomy.

The aforementioned polymers and cements can be molded into useful shapes or injected (i.e., applied in situ) which results in an anisotropic alignment of the polymer crystals, or they can be drawn and annealed by extrusion or pultrusion methods, which align the polymer crystals in an isotropic manner such that a favored directional mechanical advantage can be established that is greater than the molded or injected method. This is the way some polymer pins are formed. There are drawbacks to this practice and the materials used. There remains a top strength to the final form that may not be appropriate for all bone-reinforcement activities. There is a limit to the diameter of the final form that can be aligned, since pultrusion and extrusion heat from the outside to aid in aligning the polymer crystals, and larger diameter devices will have a core of material which is not heated and therefore is not aligned. Finally, the isotropic alignment augments performance in one direction such as compression but may increase brittleness in side shear or torsion.

Thus it will be seen that a new approach is needed for treating bone fractures.

In addition to the foregoing, in some circumstances a medical condition (e.g., osteoporosis) can weaken or damage a bone, including the creation of voids within the bone, and it may be desirable to fortify and/or augment a bone so that it can better withstand the forces associated with normal physical activity. Unfortunately, however, the aforementioned external stabilizers, internal stabilizers and bone cements have all proven inadequate for fortifying and/or augmenting a bone, e.g., for the reasons given above.

Thus it will be seen that a new approach is also needed for fortifying and/or augmenting a bone.

The present invention also relates to novel composite structures which may be used for medical and non-medical applications.

SUMMARY OF THE INVENTION

The present invention provides a new approach for treating bone fractures.

The present invention also provides a new approach for fortifying and/or augmenting a bone.

More particularly, the present invention comprises the provision and use of a novel composite implant for treating bone fractures and/or for fortifying and/or augmenting a bone. The composite implant is created from at least one reinforcing element, embedded within a matrix. The matrix material of the composite implant can be either anisotropic or isotropic, depending on the requirements of the final construct. The composite implant is disposed within the intramedullary canal of a bone, or within another opening in the bone, either directly or within a containment bag, so as to function as an internal "splint", whereby to carry the stress created during patient activity. This allows a bone fracture to heal, or provides fortification and/or augmentation of a bone, with minimum inconvenience to the patient. The composite implant comprises a plurality of components that are introduced sequentially into the patient, and assembled in-situ, wherein each of the components has a size and flexibility which allows it to be installed using a minimally invasive approach while collectively providing the required structural reinforcement for the bone which is being treated. Significantly, the properties of the composite implant can be custom tailored for different treatment situations, e.g., the composite implant can have different lengths and/or different cross-sectional dimensions, the composite implant can have different compressive and/or tensile strengths, etc., all according to the individual needs of a particular patient.

Composite implants have the added advantage of being tough, i.e., non-brittle, such that the failure mode does not result in catastrophic shattering. The ductility of a composite implant, and the interlocking of reinforcing and/or fibrous elements contained within the implant, is resistant to complete separation, thus there may be an element that breaks down, however, the final composite implant will not fully segment.

In one preferred form of the invention, the composite implant comprises three components: a containment bag, one or more reinforcing elements and an injectable matrix material.

The containment bag serves to protect the remaining components of the composite implant from the ingress of blood and/or other bodily fluids that might interfere with the deployment of the one or more reinforcing elements and/or interfere with the deployment or solidification of the injectable matrix material. The containment bag also serves to constrain the flow of the injectable matrix material while the injectable matrix material is in its injectable state. The containment bag is flexible and may be fabricated from a resorbable polymer such as a polyurethane, polylactic acid, glycolic acid or some mixture/copolymer thereof. Alternatively, the containment bag may be formed from fibers that are woven, braided, knit, nonwoven, and/or otherwise worked so as to form a mesh bag. Suitable fibers include polylactic acid, polyglycolic acid, polydioxanone or mixtures/copolymers thereof. In any case, the containment bag preferably has sufficient strength to allow the injectable matrix material to be injected into the containment bag under substantial pressure and/or vacuum so as to ensure good interfacial contact between the injectable matrix material and the one or more reinforcing elements, and to minimize voids within the containment bag, and to ensure good interfacial contact between the composite implant and the bone. Ideally the mesh bag is hydrophobic so as to minimize the ingress of bodily fluids into the containment bag that may otherwise interfere with the deployment or solidification of the various components of the composite implant.

Alternatively, the mesh bag may have a limited porosity to allow some egress of the injectable matrix material out of the containment bag, e.g., to osseointegrate with the surrounding bone. The containment bag may have a hydrophobicity and porosity that affects the biocompatibility and degradation of the composite implant by modulating the ingress of water into the interior of the containment bag. Where the containment bag is filled through a filling port, the filling port is preferably constructed so that it may be closed off, e.g., by incorporating a one-way valve in the filling port or by providing a closure mechanism (e.g., a cap). The containment bag also provides a way to control the degradation rate of the composite implant, by modifying the diffusion of water, blood, or other bodily fluids into the composite implant. Such ingress of fluids can degrade the composite implant (and/or its components) and reduce the mechanical properties of the composite implant at a faster (or slower) rate than may be desirable. Potential approaches for forming a water vapor barrier include ceramic coatings, metal coatings, and water-reactive coatings on the containment bag. Furthermore, the degradation of the composite implant (and/or its components) can also be slowed (or accelerated) by the addition of high aspect ratio platelet-shaped additives, water-reactive compounds, and/or inorganic or organic buffering agents in the containment bag. These additives, compounds and/or buffering agents can be mixed (as additives) into the formulation of the containment bag, or can be contained in protective micro- or nano-capsules.

Also, one or more compliant containment bags can be used for each composite implant. This approach can provide an improved barrier, and can also serve as a "backup" in case the first containment bag leaks, e.g., due to tearing, scratching, or contact during a surgical procedure. Microspheres that contain "self-healing" (or "self-sealing") polymerizable chemistries can also be added into the formulation of the containment bag in order to prevent leakage due to accidental scratching and tearing.

The one or more reinforcing elements comprise (i) flexible reinforcing sheets (which are preferably in the form of flexible concentric reinforcing tubes or flexible rolled reinforcing sheets), with the flexible reinforcing sheets comprising filaments formed into a textile (i.e., woven, braided, knit, nonwoven, and/or otherwise worked so as to form the flexible reinforcing sheets) or incorporated into a film so as to form the flexible reinforcing sheets, (ii) flexible reinforcing rods, with the flexible reinforcing rods comprising a plurality of filaments which are held together by an outer sheath of a textile or film (which may or may not have the same composition as the aforementioned flexible reinforcing sheets), or by a compacted (wound or compressed, etc.) connecting structure of a textile or film, or by a binder such as an adhesive, with or without surface projections for improved integration with the injectable matrix material, (iii) particulates (e.g., particles, granules, segments, nanotubes, whiskers, nanorods, etc.), or (iv) combinations of the foregoing. Where the one or more reinforcing elements comprise flexible reinforcing sheets and/or flexible reinforcing rods, the one or more reinforcing elements preferably have sufficient column strength to allow longitudinal delivery into the containment bag by pushing, and preferably have a configuration (e.g., smooth outer surfaces, tapered ends, coatings, etc.) to facilitate movement past other reinforcing elements and/or intervening structures (e.g., catheter structures). Furthermore, where the one or more reinforcing elements comprise flexible reinforcing sheets (e.g., concentric tubes or rolled sheets) which are intended to be radially compressed during delivery to facilitate passage through a small opening (e.g., a catheter or surgical opening), the flexible reinforcing sheets (e.g., concentric tubes or rolled sheets) may comprise resilient elements (e.g., resilient rings) to assist their subsequent return to an expanded state when positioned within the containment bag.

The filaments and particulates used to form the aforementioned reinforcing elements may be biodegradable or bioabsorbable, or non-biodegradable or non-bioabsorbable. By way of example but not limitation, suitable biodegradable or bioabsorbable materials include polyglycolide (PGA), glycolide copolymers, glycolide/lactide copolymers (PGA/PLA), glycolide/trimethylene carbonate copolymers (PGA/TMC), stereoisomers and copolymers of polylactide, poly-L-lactide (PLLA), poly-D-lactide (PDLA), poly-DL-lactide (PDLLA), L-lactide, DL-lactide copolymers, L-lactide, D-lactide copolymers, lactide tetramethylene glycolide copolymers, lactide/trimethylene carbonate copolymers, lactide/delta-valerolactone copolymers, lactide/epsilon-caprolactone copolymers, polydepsipeptide (glycine-DL-lactide copolymer), polylactide/ethylene oxide copolymers, asymmetrically 3,6-substituted poly-1,4-dioxane-2,4-diones, poly-β hydroxybutyrate (PHBA), PHBA/beta-hydroxyvalerate copolymers (PHBA/PHVA), poly-beta.-hydroxypropionate (PHPA), poly-beta-dioxanone (PDS), poly-DELTA-valerolactone, poly-DELTA-caprolactone, methyl methacrylate-N-vinyl pyrrolidone copolymers, citric acid polymers such as polydiolcitrates, citric acid polyurethanes, urethane-doped citric acid-based polyesters, and poly (xylitol-co-citrate), polyester amides, oxalic acid polyesters, polydihydropyrans, polypeptides from alpha-amino acids, poly-beta-maleic acid (PMLA), poly-beta-alkanoic acids, polyethylene oxide (PEO), silk, collagen, derivatized hyaluronic acid and chitin polymers, and resorbable metals, resorbable ceramics, and phosphate, borate, and silicate soluble glasses containing other inorganic ions. By way of further example but not limitation, suitable non-biodegradable or non-bioabsorbable materials include polyolefins, polyamides, polyesters and polyimides, polyetheretherketone (PEEK), and carbon fiber, and metals, ceramics, and glasses.

As will hereinafter be discussed, the one or more reinforcing elements are selected by the physician so as to provide the composite implant with the desired size, stiffness and strength. Thus, and as will hereinafter be discussed, the physician may select from a variety of different reinforcing elements, each having a particular composition and length, and preferably deliver those reinforcing elements sequentially to the patient, whereby to provide the composite implant with the desired size, stiffness and strength. The physician may, optionally, size the reinforcement elements to the appropriate length.

The injectable matrix material is preferably polymeric and is preferably biodegradable. The matrix material is preferably a multi-component polymer system that is mixed immediately prior to introduction into the patient. Preferably, each of the components and the mixture have viscosities less than 3000 cps. Optionally, the injectable matrix material may contain a biocompatible solvent, with the solvent reducing viscosity so as to allow the matrix material to be injected, and with the solvent thereafter rapidly diffusing from the composite implant so as to facilitate or provide stiffening of the composite implant. The solvent may also be used to alter the porosity of the injectable matrix material.

In one preferred form of the invention, the injectable matrix material is preferably an organic polymer that can be formed via a polymerization process.

If desired, the injectable matrix material may also comprise a bioactive or insoluble filler material, a therapeutic agent, and/or an agent to enhance visibility while imaging the composite implant.

In one preferred form of the invention, the injectable matrix material comprises a polymer comprising a blend of (i) one or more reactants with a least two functional groups, (ii) a low molecular weight functional modifier, and (iii) a poly functional aliphatic or cycloaliphatic isocyanate crosslinker. The matrix polymer may, optionally, also include (iv) a catalyst. The un-crosslinked blend has a glass transition temperature of between about 170° K to 250° K (i.e., −103.2° C. to −23.5° C.).

The first component (i.e., one or more reactants with at least two functional groups) preferably comprises (a) hydroxyl functional reaction products of a C2 to C16 aliphatic or cycloaliphatic or heterocyclic diols or triols or tetrols or blends of these polyols with a saturated or unsaturated C2 to C36 aliphatic dicarboxylic or tricarboxylic acid, anhydrides or lactones and/or lactides and/or glycolides and/or carbonates or blends of these carboxylic acids, or (b) amine functional aspartic acid ester, or (c) CH-active compounds, or blends of the foregoing.

Examples of some of the typical dicarboxylic acid and polyols to prepared polyester polyols useful in the present invention are shown in U.S. Patent Application Publication No. 2013/0171397 and in U.S. Pat. Nos. 2,951,823 and 2,902,462.

The second component (i.e., a low molecular weight functional modifier) preferably comprises an aliphatic or cycloaliphatic or heterocyclic diol with C2 to C12 carbons.

The third component (i.e., a poly functional aliphatic or cycloaliphatic isocyanate crosslinker) preferably comprises an isocyanurate (trimer), iminooxadiazine dione (asymmetric trimer), biuret, allophanate or uretdione (dimer) derivative (with an average functionality of between 2.0 to 4) of an C4 to C15 aliphatic or cycloaliphatic diisocyanate or lysine diisocyanate, or a C4 to C15 aliphatic or cycloaliphatic diisocyanate or lysine diisocyanate. The crosslinked network has a crosslink density with an average molecular weight between crosslinks of between 200 to 500.

The fourth (optional) component (i.e., a catalyst) is preferably selected from the group of metals such as bismuth, potassium, aluminum, titanium, zirconium compounds or a t-amine, or organo-tin compounds.

The foregoing polymer blend is reactive at a temperature of between 5° C. to 150° C., or 10° C. to 70° C., or 10° C. to 50° C. to form a rigid polymer matrix with a Tg (glass transition temperature) between 273.2° K (0° C.) and 423° K (150° C.), more preferably between 273° K (0° C.) and 373° K (100° C.), and more preferably between 313° K (40° C.) and 343° K (70° C.), and more preferably greater than 303° K (30° C.) and is biodegradable over a maximum 5 year period and preferably within a 3 year period. The polymer may also be cross-linked using other common energy processes such as lasers, energy processes such as lasers, energy beams and ultraviolet light or other energy sources.

The molar ratio of the above matrix is 0.8 to 1.3 reactant functional group to isocyanate functional group.

The cross-linked network is formed at a temperature of between 20° C. to 60° C. within a time period of less than 24 hours.

Optionally, the matrix may also include a non-reactive polyester plasticizer in the amount of 0-30% of the weight of the matrix. The plasticizer for the matrix may consist of non-reactive aliphatic polyesters such as shown in U.S. Pat. No. 5,047,054 among others.

Optionally, the matrix can contain other typical ingredients used in composites, and other formulated products such as paints, inks, adhesives and sealants. These other ingredients may be pigment or filler particles, surfactants, defoamers, and other commonly known and used additives The above glass transition temperature Tg of the reactant can be obtained by measurements or also by calculation using the William Landel Ferry Equation (WLF).

Above aspartic acid ester reactants are described in U.S. Pat. Nos. 7,754,782; 5,847,195; 5,126,170; 5,236,741; 5,243,012; 5,489,704; 5,516,873; 5,580,945; 5,597,930; 5,623,045; 5,633,389; 5,821,326; 5,852,203; 6,107,436; 6,183,870; and 6,355,829, among others.

The above CH active compounds are the malonic acid ester of above diols or triols or an acetoacetic ester of the above diols or triols.

In one preferred form of the invention, there is provided a novel composite comprising (i) a barrier (which may be a containment bag or coating) which is water permeable and which contains hydrolyzable sites so that the barrier will break down over time when placed in an aqueous environment (e.g., water, the body, etc.); (ii) a flowable/settable matrix which is hydrolyzable so that the matrix will break down over time when contacted by an aqueous environment; and (iii) reinforcing elements which are disposed within the flowable/settable matrix and which, when they come into contact with an aqueous environment, break down and give off catalysts which modify (e.g., increase) the hydrolysis of the matrix material. Thus, in this form of the invention, the barrier provides a means for regulating the degradation of the matrix material, and the reinforcing elements provide a means for modifying (e.g., increasing) the hydrolysis of the matrix material.

The composite implant is disposed within the intramedullary canal of a bone, or within another opening in the bone, so as to function as an internal "splint", whereby to carry the stress created during patient activity. This allows a bone fracture to heal, or provides fortification and/or augmentation of bone, with minimum inconvenience to the patient.

As a modular system, each element of the composite implant is capable of being delivered to a fracture site in a minimally invasive manner (e.g., with an access point as small as 3 mm) and assembled within the body, i.e., with an in situ construction. This form of the invention is advantageous, inasmuch as the final composite implant will have strength commensurate with the non-fractured bone and will be physically tough (i.e., non-brittle) but will have low impact on the patient's soft tissue during implantation, thereby allowing a quicker return to activities.

A containment bag can be used to protect the remaining components of the composite implant from the ingress of blood and/or other bodily fluids that might interfere with the deployment of the one or more reinforcing elements and/or interfere with the deployment or solidification of the injectable matrix material.

In one preferred form of the invention, the components of the composite implant are introduced sequentially into the patient, and assembled in-situ, thereby allowing the composite implant to be installed using a minimally invasive approach.

In another preferred embodiment of the present invention, the aforementioned composite implant is preassembled for insertion via "open" procedures when minimally invasive procedures are not required or are not advantageous to the patient. In this situation, a pre-formed composite implant may be molded or pultruded so as to form a strong composite implant with features such as barbs, threads, and/or other mechanical features advantageous for implantation or to create blanks that can be machined or over-molded to a final mechanical shape. If the composite implant is constructed using bioabsorbable materials, the composite nature of the composite implant will deliver superior strength and toughness performance over products produced with a pure or blended polymer matrix. Additionally, the protrusion pultrusion or extrusion that includes a reinforcement element will not have the restriction on diameter imposed on polymer protrusion since alignment of the matrix polymer crystals is of secondary import to the inclusion of the reinforcing element. The composite implant may be secured mechanically (threads) or by further use of injectable matrix material to fill the spaces and act as liquid threads for the composite implant.

In another preferred embodiment of the present invention, pre-cured pins or rods can be fabricated and used to assemble the composite implant. These pre-cured pins or rods may be fabricated from the reinforcement elements and injectable matrix materials described elsewhere in this application, and can be formed via processes such as extrusion, pultrusion, or molding. For example, reinforcement elements formed from fiber braids can be preassembled as pre-cured rods for insertion via "open" procedures when minimally invasive procedures are not required or are not advantageous to the patient. Depending on the application, one or more of such pre-cured rods or pins can be used in the procedure. Where pre-cured rods or pins are fabricated in this manner, the pre-cured rods or pins may be substantially rigid or they may have a limited degree of flexure. It is not required that the polymer matrix in the pins or rods be fully cured; they can be cured after assembly.

Depending on the application, one or more of such pre-cured rods or pins can be used in the procedure. In some applications, at least 3 or more, 4 or more, or 5 or more rods can be used in a procedure, preferably with maximum of 50 rods, or preferably a maximum of 40 rods, and more preferably a maximum of 30 rods. In one preferred form of the invention, 15-25 rods are used, which yields an excellent reinforcement element-to-matrix material ratio (by volume) for optimal composite implant performance. The bending modulus of the rods can be between 2 GPa to 80 GPa, preferably greater than 10 GPa, more preferably greater than 15 GPa, and more preferably greater than 20 GPa. It should be noted that it is not required for all the rods or pins to have the same material, modulus or shape, and rods of different materials, shapes and modulus can be chosen depending on the application or procedure. In some applications or procedures, the rods or pins can be heated to improve their flexibility for easier insertion in the bone, or the containment bag.

In some applications, the diameter of the rods is less than 5 mm, more preferably less than 4 mm, more preferably less than 3 mm, and most preferably between 0.25 mm and 2.5 mm. It should be noted it is not required for all the rods or pins to have the same material, modulus, diameters or shape, and rods of different materials, shapes, diameters and modulus can be chosen depending on the application or procedure.

By way of example but not limitation, the composite implant may be used in the following manner to treat a fracture in the tibia.

The first step is to create an access hole into the bone that is to be treated. When treating fractures in long bones, the hole is made into the intramedullary canal distal to, or proximal to, the fracture site.

The second step is to remove or harvest the bone marrow (and/or other matter) in the intramedullary canal, and to clean the intramedullary canal, so as to provide a space for the composite implant. This is done through the access hole previously created. In one preferred form of the invention, the device for removing or harvesting of the bone marrow from the intramedullary canal comprises a catheter with provision for introducing a liquid or gas into the intramedullary canal and suction for removal of material from the intramedullary canal. The liquid or gas can be used to disrupt the content in the intramedullary canal or prepare the intramedullary canal for a composite implant. The liquid or gas can be introduced in a continuous, pulsed, or intermittent flow. A rotatable flexible rod, with a shaped end or attachment at the distal end, is optionally used to disrupt the bone marrow in the intramedullary canal so as to aid in the removal of the bone marrow. When harvest of the bone marrow is required, a tissue trap is utilized.

The third step, if needed, is to place a flow restrictor plug in the intramedullary canal distal to, and/or proximal to, where the composite implant will be placed in the intramedullary canal. Again, this is done through the access hole previously created. The flow restrictor plugs may be placed prior to the removal or harvest of the bone marrow (and/or other matter) to define the area to be cleaned. Where two flow restrictor plugs are used, the two flow restrictor plugs may be connected to one another.

The fourth step, if needed, is to return the bone to proper alignment.

The fifth step is to introduce the containment bag into the intramedullary canal via the access hole previously created. In one preferred form of the invention, the containment bag is introduced into the intramedullary canal through a delivery catheter, and is releasably attached to a catheter that is used for subsequent delivery of the remaining components of the composite implant, i.e., the one or more reinforcement elements and the injectable matrix material. Note that the flexible (and compressible) nature of the containment bag facilitates its delivery into the intramedullary canal via a minimally invasive approach (i.e., via the access hole previously created). The containment bag may comprise an auxiliary channel to allow monitoring and control of subsequent pressure within the containment bag. The auxiliary channel may be used to remove entrapped air from the composite implant during filling of the containment bag with the injectable matrix material. The auxiliary channel may also be used to pressurize or depressurize (create a vacuum) the injectable matrix material so as to enhance bonding of the injectable matrix material with adjacent structures (e.g., the reinforcing elements, the containment bag, bone, etc.). This auxiliary channel may be parallel to the delivery catheter, or inside the delivery catheter, or the auxiliary channel may be at the distal end of the containment bag. Alternatively, there may be a valve at the distal end of the containment bag, or at other strategic regions of the containment bag, that can limit pressure within the containment bag.

The sixth step is to sequentially introduce the one or more reinforcing elements into the containment bag. This is done through the access hole previously created. Note that the flexible nature of the reinforcing elements facilitates their delivery into the containment bag via the access hole previously created. Alternatively, the reinforcing elements are reversibly made flexible via external energy, such as the application of heat or an electrical current, prior to insertion through the catheter, and attain maximum strength (or return to full strength) once delivered to the target area to be splinted. The one or more reinforcing structures are preferably introduced into the containment bag sequentially so as to build up a reinforcing mass. In one preferred form of the invention, a plurality of flexible concentric reinforcing tubes are sequentially inserted into the containment bag, with one flexible reinforcing tube being nested inside another, and a plurality of flexible reinforcing rods are sequentially inserted within the innermost concentric reinforcing tube. In one preferred form of the invention, the flexible reinforcing sheets (which are preferably in the form of concentric tubes or rolled sheets) are delivered to the interior of the containment bag by pushing them out of a delivery tube or, alternatively, by carrying them into the containment bag while held within a delivery tube and then retracting the delivery tube, whereby to expose the flexible reinforcing sheets. Preferably the size and number of concentric reinforcing tubes and reinforcing rods are selected so as to meet the individual needs of a particular patient. The number of concentric reinforcing tubes utilized in the composite implant, and/or their lengths and/or cross-sectional dimensions, and/or the number of reinforcing rods used, and/or their lengths and/or cross-sectional dimensions, may be selected according to the individual needs of a particular patient. Preferably the number, length, and cross-sectional dimensions of the reinforcing tubes, and the number, length, and cross-sectional dimensions of the reinforcing rods, are selected so as to provide a composite implant having variable stiffness along its length, e.g., a composite implant having a stiffer central region (e.g., 20 GPa) and less stiff distal and proximal ends (e.g., 3 GPa), whereby to prevent stress risers from being created at the ends of the composite implant. To this end, the reinforcing tubes, and the reinforcing rods, are preferably provided in a variety of sizes with a range of mechanical properties for appropriate selection by the physician; alternatively, the reinforcing tubes and/or reinforcing rods may be sized at the time of use by the physician. The reinforcing rods may include a polymer matrix, and the combination may be pre-cured to a rigid, or somewhat flexible, state so as to provide for the easier insertion of the reinforcing rods. If desired, a guidewire may be provided to facilitate introduction of the one or more reinforcing elements into the containment bag. This guidewire is preferably attached to the distal end of the containment bag using an adhesive or other non-permanent attachment means. After the one or more reinforcement elements have been placed in the containment bag, the guidewire can be detached from the containment bag by pulling or twisting the guidewire. Alternatively, the guidewire may be absorbable, in which case it may be left in the patient at the conclusion of the procedure.

In one embodiment, one or more of reinforcing fibers, braids, pins, or rods are placed inside the containment bag before the containment bag is inserted into the bone canal, in which case the foregoing sixth step may not be required.

The seventh step is to introduce the injectable matrix material into the containment bag. Again this is done through the access hole previously created. In one preferred form of the invention, an injection tube is used to deliver the injectable matrix material into the containment bag under pressure, where it flows over and through the one or more reinforcement structures contained within the containment bag. Vacuum may be used during the delivery of the injectable matrix material to aid in the wetting out of the reinforcement structures and removal of trapped air. Vacuum may be achieved through a medical facility's common "wall" suction or through volume evacuation via a disposable syringe, such as a 60 cc syringe from Becton-Dickinson. The injection tube is withdrawn after the matrix material is injected into the containment bag. The injection tube is, preferably, also capable of transmitting an energy wave (such as electro-magnetic, or electro-mechanical such as ultrasonic vibration, light) into the injectable matrix material in cases where pulsatile flow or the application of vibrational forces is required to aid injecting the matrix material into the containment bag or to initiate curing of the matrix material.

The eighth step is to solidify the injectable matrix material so that the matrix material, the one or more reinforcing elements and the containment bag become a single solidified structure capable of providing support across the fracture line while the bone fracture heals. This reaction can be catalyzed with energy (electromagnetic—alternating current or ultra-violet, acoustic—ultrasound, or electro-mechanical such as ultrasonic vibrations), a chemical catalyst with a time delayed action, or a chemical catalyst released at a preferable time frame as per the disruption of catalyst-filled micro-bubbles. Preferably, the solidification process occurs at a rate that allows for complete filling and wet-out of the composite structure prior to achieving a gel-like state within minutes and hardens to a reasonably immovable mass within tens of minutes with a full hard state achieved within 5 days.

The ninth step is to close the wound.

Thus it will be seen that the present invention comprises the provision and use of a novel composite implant for treating bone fractures (and/or for fortifying and augmenting a bone). The composite implant is disposed within the intramedullary canal of the bone (or within another opening in the bone) so as to function as a "splint", whereby to carry the stress created during patient activity. This approach allows the bone fracture to heal (or provides fortification and/or augmentation of a bone) with minimum inconvenience to the patient. The composite implant comprises a plurality of components that are introduced sequentially into the patient, and assembled in situ, thereby allowing the composite implant to be installed using a minimally invasive approach. Significantly, the properties of the composite implant can be custom tailored for different treatment situations, e.g., the composite implant can have different lengths and/or cross-sectional dimensions, the composite implant can have different mechanical properties, e.g. compressive and/or tensile strengths, etc., all according to the individual needs of a particular patient.

In another preferred form of the invention, the components of the composite implant are assembled or manufactured external to the body, and then introduced to the implant site, e.g., as an implant of various geometries such as pins, screws, or nails. In another form of the invention, the injectable matrix material may partially pre-manufactured external to the body, and further impregnated or interfaced with the implant site by an additional amount of the injectable matrix material hardened after the composite implant has been introduced to the implant site in order to support the bone. For example, the reinforcement braids can be combined with a polymer-based matrix and the combination of braids and matrix pre-cured so as to form pins or rods, and these pre-cured pins or rods can then be introduced into the containment bag in the bone canal, followed by the injection of additional injectable matrix material to achieve the composite implant. Note that a single braid or fiber can be combined with matrix material so as to form the pins or rods; or multiple braids or fibers can be "glued together" with matrix material so as to form the pins or rods. And note that a single pin or rod can be placed inside the containment bag with matrix material, whereby to form the composite implant; or multiple pins or rods can be placed inside the containment bag with matrix material, whereby to form the composite implant.

In another preferred form of the present invention, there is provided a method for treating a bone, the method comprising:

selecting at least one reinforcing element to be combined with an injectable matrix material so as to together form a composite implant capable of supporting the bone;

positioning the at least one reinforcing element in a cavity in the bone;

flowing the injectable matrix material into the cavity in the bone so that the injectable matrix material interfaces with the at least one reinforcing element; and transforming the injectable matrix material from a flowable state to a non-flowable state so as to establish a static structure for the composite implant, such that the composite implant supports the adjacent bone.

In another preferred form of the present invention, there is provided a composite implant comprising a containment bag, an injectable matrix material for positioning within the containment bag, wherein the injectable matrix material is flowable and settable, and at least one reinforcing element for positioning within the containment bag and integration with the injectable matrix material, the at least one reinforcing element adding sufficient strength to the injectable matrix material such that when the composite implant is disposed in a cavity in a bone, the composite implant supports the bone;

wherein the containment bag comprises a permeation barrier for providing at least one of (i) prohibiting or modulating the release of injectable matrix material out of the containment bag into the surrounding environment, and (ii) prohibiting or modulating the ingress of body fluids into the interior of the containment bag, whereby to regulate contact of body fluids with the injectable matrix material and the reinforcing elements, whereby to regulate the degredation rate of the injectable matrix material and the reinforcing elements.

In another preferred form of the present invention, there is provided a method for treating a bone, the method comprising:

providing a containment bag, at least one reinforcing element to be positioned within the containment bag, and an injectable matrix material to be positioned within the containment bag so as to together form a composite implant capable of supporting the bone, wherein the containment bag comprises a permeation barrier for providing at least one of (i) prohibiting or modulating the release of injectable matrix material out of the containment bag into the surrounding environment, and (ii) prohibiting or modulating the ingress of body fluids into the interior of the containment bag, whereby to regulate contact of body fluids with the injectable matrix material and the reinforcing elements, whereby to regulate the degredation rate of the injectable matrix material and the reinforcing elements;

positioning the containment bag in a cavity in the bone;

positioning the at least one reinforcing element in the containment bag;

flowing the injectable matrix material into the containment bag so that the injectable matrix material interfaces with the at least one reinforcing element; and transforming the injectable matrix material from a flowable state to a non-flowable state so as to establish a static structure for the composite implant, such that the composite implant supports the adjacent bone.

In another preferred form of the present invention, there is provided a thermoplastic polymer implant comprising a thermoplastic polymer matrix and a high modulus fiber component having a tensile modulus from about 8 GPa to about 400 GPa.

In another preferred form of the present invention, there is provided a method for treating a bone, the method comprising:

selecting at least one reinforcing element to be combined with an injectable matrix material so as to together form a composite implant capable of supporting the bone, wherein the at least one reinforcing element comprises a high modulus fiber component having a tensile modulus of about 8 GPa to about 400 GPa;

positioning the at least one reinforcing element in a cavity in the bone;

flowing the injectable matrix material into the cavity in the bone so that the injectable matrix material interfaces with the at least one reinforcing element; and transforming the injectable matrix material from a flowable state to a non-flowable state so as to establish a static structure for the composite implant, such that the composite implant supports the adjacent bone.

In another preferred form of the present invention, there is provided a method for treating a bone, the method comprising:

selecting at least one high modulus fiber component having a tensile modulus from about 8 GPa to about 400 GPa, wherein the at least one high modulus fiber component comprises a rod having a cross-section selected from the group consisting of round and circular;

flowing an injectable matrix material into the cavity in the bone so that the injectable matrix material interfaces with the at least one high modulus fiber component so as to form a composite implant, wherein the injectable matrix material comprises a thermoplastic polymer matrix; and transforming the injectable matrix material from a flowable state to a non-flowable state so as to establish a static structure for the composite implant, such that the composite implant supports the adjacent bone.

In another preferred form of the present invention, there is provided a method for treating a bone, the method comprising:

selecting at least one high modulus fiber component having a tensile modulus from about 8 GPa to about 400 GPa, wherein the high modulus fiber component comprises a plurality of fibers, and further wherein the high modulus fiber component is pre-loaded with an injectable matrix material just prior to implantation so as to together form a composite implant, wherein the injectable matrix material comprises a thermoplastic polymer matrix;

positioning the composite implant in a cavity in the bone;

flowing additional injectable matrix material into the high modulus fiber component so that the injectable matrix material exudes from the surfaces of the high modulus fiber component and interfaces with the surrounding bone cavity; and transforming the injectable matrix material from a flowable state to a non-flowable state so as to establish a static structure for the composite implant, such that the composite implant supports the adjacent bone and or approximated soft tissue.

In another preferred form of the present invention, there is provided a polymer implant comprising a high modulus fiber reinforcing component and a urethane polymer matrix.

In another preferred form of the present invention, there is provided a method for treating a bone, the method comprising:

selecting at least one high modulus fiber reinforcing component to be combined with a urethane polymer matrix so as to together form a polymer implant capable of supporting the bone;

positioning the at least one high modulus fiber reinforcing component in a cavity in the bone;

flowing the urethane polymer matrix into the cavity in the bone so that the urethane polymer matrix interfaces with the at least one high modulus fiber reinforcing component; and transforming the urethane polymer matrix from a flowable state to a non-flowable state so as to establish a static structure for the polymer implant, such that the polymer implant supports the adjacent bone.

In another preferred form of the present invention, there is provided a method for treating a bone, the method comprising:

selecting at least one pre-formed polymer implant created from at least one high modulus fiber reinforcing component combined with a urethane polymer matrix so as to together form a polymer implant capable of supporting the bone;

positioning the at least one pre-formed polymer implant in a cavity in the bone;

flowing a urethane polymer matrix into the cavity in the bone so that the urethane polymer matrix interfaces with the at least one pre-formed polymer implant; and transforming the urethane polymer matrix from a flowable state to a non-flowable state so as to establish a static structure for the polymer implant, such that the polymer implant supports the adjacent bone.

In another preferred form of the present invention, there is provided a method for treating a bone, the method comprising:

selecting at least one high modulus fiber reinforcing component which is pre-loaded with a urethane polymer matrix just prior to implantation so as to together form a polymer implant capable of supporting the bone once fully cured;

positioning at least one high modulus fiber reinforcing component in a cavity in the bone;

flowing additional urethane polymer matrix into the at least one high modulus fiber reinforcing component so that the urethane polymer matrix exudes from the surfaces of the at least one high modulus fiber reinforcing component and interfaces with the surrounding bone cavity; and transforming the urethane polymer matrix from a flowable state to a non-flowable state so as to establish a static structure for the polymer implant, such that the polymer implant supports the adjacent bone and or approximated soft tissue.

In another preferred form of the present invention, there is provided a composite implant comprising an injectable matrix material which is flowable and settable, and at least one reinforcing element for integration with the injectable matrix material, the injectable matrix material comprising a resin, and the at least one reinforcing element adding sufficient strength to the injectable matrix material such that when the composite implant is disposed in a cavity in a bone, the composite implant supports the bone.

The present invention also relates to novel composite structures which may be used for medical and non-medical applications.

In another preferred form of the present invention, there is provided a composite comprising:

a barrier, said barrier being configured to selectively pass water, and said barrier being degradable in the presence of water;

a matrix material for disposition within said barrier, wherein said matrix material has a flowable state and a set state, and wherein said matrix material is degradable in the presence of water; and at least one reinforcing element for disposition within said barrier and integration with said matrix material, wherein said at least one reinforcing element is degradable in the presence of water, and further wherein, upon the degradation of said at least one reinforcing element in the presence of water, provides an agent for modulating the degradation rate of said matrix material in the presence of water.

In another preferred form of the present invention, there is provided a method for using a composite, said method comprising:

providing a composite comprising:

a barrier, said barrier being configured to selectively pass water, and said barrier being degradable in the presence of water;

a matrix material for disposition within said barrier, wherein said matrix material has a flowable state and a set state, and wherein said matrix material is degradable in the presence of water; and at least one reinforcing element for disposition within said barrier and integration with said matrix material, wherein said at least one reinforcing element is degradable in the presence of water, and further wherein, upon the degradation of said at least one reinforcing element in the presence of water, provides an agent for modulating the degradation rate of said matrix material in the presence of water; and positioning said composite in an environment containing water.

In another preferred form of the present invention, there is provided a method for treating a bone, said method comprising:

providing (i) a barrier, said barrier being configured to selectively pass water, and said barrier being degradable in the presence of water; (ii) a matrix material, wherein said matrix material has a flowable state and a set state, and wherein said matrix material is degradable in the presence of water; and (iii) at least one reinforcing element which is degradable in the presence of water, and further wherein, upon the degradation of said at least one reinforcing element in the presence of water, provides an agent for modulating the degradation rate of said matrix material in the presence of water;

positioning said barrier in a cavity in the bone so as to create an enclosure;

positioning said at least one reinforcing element within said enclosure;

flowing said matrix material into said enclosure so that said matrix material interfaces with said at least one reinforcing element; and transforming said matrix material from a flowable state to a set state so as to establish a static composite structure, such that said static composite structure supports the adjacent bone.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 8A, 8B, 8C and 8D are schematic views showing alternative forms of the flexible reinforcing rods of the present invention;

DETAILED DESCRIPTION OF THE PREFERRED EMBODIMENTS

The present invention provides a new approach for treating bone fractures using a composite implant.

The present invention also provides a new approach for fortifying and/or augmenting a bone using a composite implant.

The present invention also relates to novel composite structures which may be used for medical and non-medical applications.

Composite Implant

More particularly, the present invention comprises the provision and use of a novel composite implant for treating bone fractures and/or for fortifying and/or augmenting a bone. The composite implant is disposed within the intramedullary canal of a bone, or within another opening in the bone, so as to function as an internal "splint", whereby to carry the stress created during patient activity. This allows a bone fracture to heal, or provides fortification and/or augmentation of a bone, with minimum inconvenience to the patient. The composite implant comprises a plurality of components that are introduced sequentially into the patient, and assembled in-situ, wherein each of the components has a size and flexibility that allows it to be installed using a minimally invasive approach while collectively providing the required structural reinforcement for the bone that is being treated. Significantly, the properties of the composite implant can be custom tailored for different treatment situations, e.g., the composite implant can have different lengths and/or different cross-sectional dimensions, the composite implant can have different compressive and/or tensile strengths, etc., all according to the individual needs of a particular patient. Also significantly, the composite implant of the present invention is amenable to both in situ fabrication and pre-operative assembly of more conventional means.

Figure 1:
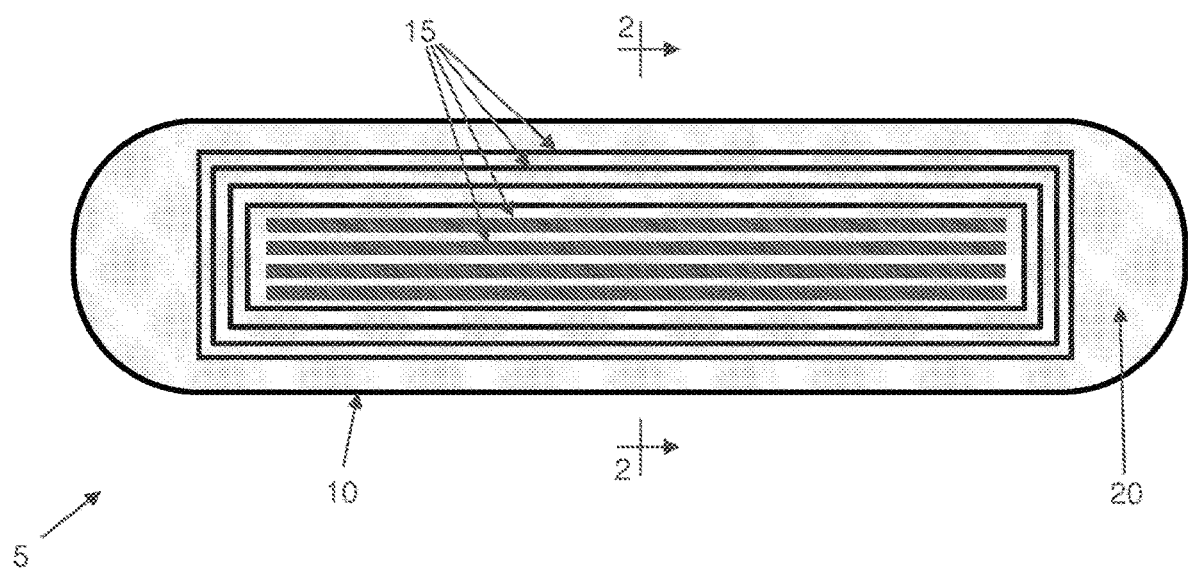
FIGS. 1 and 2 are schematic views of a composite implant formed in accordance with the present invention.
Figure 2:
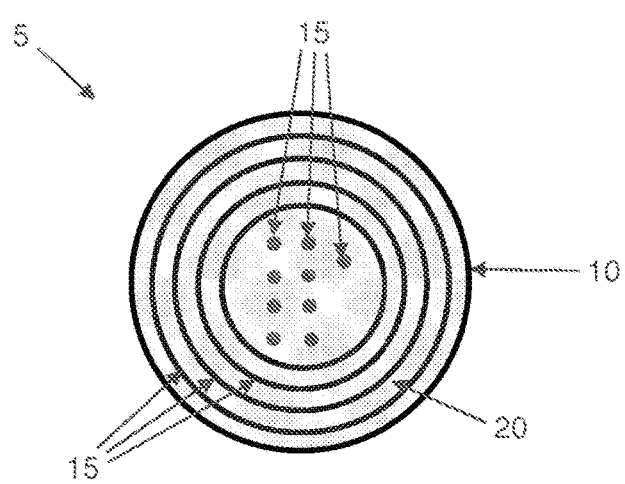

In one preferred form of the invention, and looking now at FIGS. 1 and 2, the composite implant 5 comprises three components: a containment bag 10, one or more reinforcing elements 15 and an injectable matrix material 20.

Containment Bag

The containment bag 10 serves to protect the remaining components of the composite implant from the ingress of blood and/or other bodily fluids that might interfere with the deployment of the one or more reinforcing elements 15 and/or interfere with the deployment or solidification of the injectable matrix material 20. The containment bag 10 also serves to constrain the flow of the injectable matrix material 20 while the injectable matrix material 20 is in its injectable state. Therefore, the containment bag consists of a flexible enclosure (bag) and may include a biodegradable sealing mechanism such as a valve V (see FIGS. 12, 13, 20 and 22).

The containment bag is flexible and may be fabricated from a resorbable polymer such as a polyurethane, polylactic acid, glycolic acid or some mixture/copolymer thereof, or thermoplastics such as polycaprolactones (PCL), polylactic acids (PLA), polyhydroxybutyrates (PHB), polyhydroxyalkanoates (PHA), poly(3-hydroxybutyrate-co-3-hydroxyvalerates) (PHBV), citric acid polymers such as polydiolcitrates, citric acid polyurethanes, urethane-doped citric acid-based polyesters, and poly (xylitol-co-citrate), and variations and blends and copolymers thereof, with variable crystallinity and/or molecular weight so as to adjust the rate of the ingress of water or aqueous fluid through the bag. The polymers listed previously can also be compounded within a range of 1-25% volume fraction, preferably 2-10% volume fraction, with nano- and/or micro-particulate with a range of sizes from 1 nm to 100 um, and may, optionally, have a range of aspect ratios (either aligned or misaligned), from 1-500 (length/diameter). The particulate can be inorganic materials such as bioabsorbable glasses, calcium phosphate salts of any Ca/P ratio, carbon nano-structures, or nano-clays such as cloisite, halloysite, bentonite, or montmorillonite, or modified nanoclays such as organomontmorillonite, or metal compounds including composite oxides (such as magnesium oxide or magnesium hydroxide), etc. The particulate could also be organic, such as jute or silk fibers. The particulate can be used to improve mechanical properties of the bag. Particulate that is insoluble in a time frame relative to the surrounding material and/or the composite within the barrier can act as a torturous path for water delaying ingress of aqueous media. Both improved mechanical properties and improved water barrier properties are particularly effectively implemented when the aspect ratio is 10:1 or greater, preferably 100:1 or greater, for two dimensions over a third such as with clays, iron oxide, aluminum oxide, silicon carbide, and magnesium hydroxide (after certain heating schedules). The use of particulate is not limited to these uses. To effectively use the particulates, dispersants and sizings/coatings may be required. In particular, a dispersant based on poly-hydroxy-stearic acid will be biocompatible and assure proper spacing of the particulate within the polymer layer. Similar sizings to those listed in the "sizings" section are also appropriate for aiding in bond strength and quality for the particulates in the containment bag. Alternatively, the containment bag 10 may be formed from fibers that are woven, braided, knit, electro-spun, nonwoven, and/or otherwise worked so as to form a mesh bag. Suitable fibers include polylactic acid, polyglycolic acid, polydioxanone or mixtures/copolymers thereof, carbon fibers, bioresorbable and soluble glasses, and/or metal, and/or PHBs. The containment bag can be formed by constructing sequential or alternating layers, typically between 1 and 25 layers, preferably between 2 and 7 layers, of the same or varying materials in any combination, either by alternating axial orientation or not, such as by co-extrusion, heat pressing, or by any method of combining the materials. There is a "layer multiplication" technique that can build alternating nanolayers of material that decreases the water permeation tremendously. In addition, polymer layers with and without particulate can be sequentially built using methods such as solvent dip coating, dip casting, spray coating, and vapor deposition. The layers can be designed for different purposes such as a high solvent (water) barrier layer (WVP—water vapor permeability—between $10^{-2}$ g*mm/m$^2$*days and $10^{2}$ g*mm/m$^2$*days, preferably between 0.2 and 20 g*mm/m$^2$*days, or more preferably between 0.3 and 15 g*mm/m$^2$*days, or more preferably between 0.2 and 8 g*mm/m$^2$*days); a highly compliant layer to aid with bag/balloon folding and toughness, and/or a layer for compatibalizing the balloon with the endosteum. In any case, the containment bag preferably has sufficient strength to allow the injectable matrix material to be injected into the containment bag under substantial pressure so as to ensure good interfacial contact between the injectable matrix material and the one or more reinforcing elements, the containment bag and the bone, and to minimize voids within the containment bag. The containment bag may be hydrophobic so as to minimize the ingress of bodily fluids into the containment bag that may otherwise interfere with the deployment or solidification or accelerate the degradation of the various components of the composite implant. Optionally, the containment bag may have a limited porosity to allow some egress of the injectable matrix material 20 out of the containment bag, e.g., to osseointegrate with the surrounding bone. In this respect it should be appreciated that such porosity may be varied across the extent of the containment bag so as to provide regions of greater or lesser porosity to the injectable matrix material 20, thus providing control of the ability of the injectable matrix material to infiltrate the surrounding bone.

To control the diffusion rates into and out of the containment bag, the containment bag may be coated with a resorbable metal layer, such as magnesium, silver, nickel, titanium, and/or metal alloys such as magnesium calcium alloys. Such coatings can be applied via vapor coating, sputtering, atomic layer deposition, chemical vapor deposition, or electroplating and electroless plating. Such metal layers provide reduced diffusion, but can also react with water to provide basic/alkaline products that can act as buffering and degradation control agents for the polymer matrix and/or glass fibers. Rather than using a coating, metal nano- or micro-particles can be added to the injectable matrix material and/or the containment bag.

Another possible approach could be ceramic coatings on the containment bag. Such coatings can be made by the surface reaction of ethyoxysilanes such as tetraethoxysilane, methyltriethoxysilane, dimethyldiethoxysilane, or trimethylethoxysilane; polycarbosilane, or polysilazanes such as perhydropolysilazane- or polysilazane-modified polyamines.

The above coatings can be applied to the outside and/or inside surfaces of the containment bag, or can be included as an intermediate layer, for example, magnesium- or magnesium alloy-based metal foil that is sandwiched between other layers of the containment bag.

Significantly, the porosity of the containment bag may be set so as to regulate the permeability of body fluids into the interior of the containment bag, whereby to regulate contact of those body fluids with the injectable matrix material and the reinforcing elements, whereby to regulate the degradation rate of the injectable matrix material and the reinforcing elements.

Thus, in one form of the invention, containment bag 10 comprises a structural barrier for constraining the disposition of one or more reinforcing elements 15 and injectable matrix material 20 within the bone. Significantly, containment bag 10 may comprise a permeation barrier for prohibiting or modulating the release of injectable matrix material 20 out of containment bag 10 and into the surrounding environment. Furthermore, containment bag 10 may comprise a permeation barrier for prohibiting or modulating the ingress of body fluids into the interior of the containment bag (and hence regulating the degradation rate of injectable matrix material 20 and/or reinforcing elements 15 contained within the containment bag).

In one form of the invention, containment bag 10 comprises a PHA, e.g., Polyhydroxybutyrate (PHB), poly-3-hydroxybutyrate (P3HB), poly-4-hydroxybutyrate (P4HB), polyhydroxyvalerate (PHV), polyhydroxyhexanoate (PHH), polyhydroxyoctanoate (PHO), 3HA acids, etc.

In one form of the invention, containment bag 10 comprises copolymers made from made from monomers, e.g., glycolic acid, lactic acid, 3-hydroxypropionic acid (3HP), 4-hydroxybutyrate (4HB), 5-hydroxyvalerate (5HV), 3-hydroxyhexanoate (3HH), 6-hydroxyhexanoate (6HH), 3-hydroxyoctanoate (3HO), etc.

In one form of the invention, containment bag 10 comprises a PHA copolymer, e.g., polyhydroxyoctanoate-co-hexanoate (PHOH), polyhydroxybutyrate-co-valerate (PHBV), 3-polyhydroxybutytrate-co-4-polyhydroxybutyrate (PHBco4HB), 3-polyhydroxybutytrate-co-5-polyhydroxy valerate, 3-polyhydroxybutytrate-co-6-polyhydroxyhexanoate, poly-3-hydroxybutyrate-co-4-hydroxybutyrate copolymer, PHB4HB, PHBco4HB, PLA/P(3HB-3HH), etc.

Thus, in a further form of the invention, containment bag 10 comprises a layered structural barrier for constraining the disposition of one or more reinforcing elements 15, optionally from 3 to 50 elements, or 4 to 30 elements, or 5 to 25 elements, and injectable matrix material 20 within the bone. Significantly, the inner layer of the containment bag 10 may comprise a permeation barrier for prohibiting or modulating the ingress of body fluids into the interior of the containment bag (and hence regulating the degradation rate of injectable matrix material 20 and/or reinforcing elements 15 contained within the containment bag) using a bioabsorbable polymer such as, but not limited to, poly lactic-acid with suspended insoluble particulate such as Magnesium Hydroxide with a plate-like morphology (WVP between 0.4 and 20 g*mm/m$^2$*days). A central layer of the containment bag may be constructed of an adhesive, relatively compliant bioabsorbable material such as poly (ε-capralactone) with or without suspended particulate that supplies a toughness and compliance to the bag structure. The final outer layer could be created using a bioabsorbable polymer with suspended biocompatibalizing agents, such as Hydroxy-apatite, such that the external layer of the balloon is compatibalized with the bone endosteum.

One or more such containment bags can be used for each composite implant. Where more than one containment bag is used for the composite implant, the multiple containment bags can provide an improved barrier, and/or can also serve as a "backup" in case the first containment bag leaks, due to tearing, scratching, or contact during a surgical procedure. Microspheres that contain "self-healing" (or "self-sealing") polymerizable chemistries can also be added to the formulation of the containment bag to prevent leakage due to accidental scratching and tearing.

See Examples 84-95 for exemplary constructions for biodegradable/absorbable barriers.

It should also be appreciated that containment bag 10 may be formed out of one or more of the materials used to form reinforcing elements 15 and/or one or more of the materials used to form injectable matrix material 20, appropriately processed so as to provide the functional requirements of containment bag 10.

Where the containment bag is filled through a filling port, the filling port is preferably constructed so that it may be closed off, e.g., by incorporating a one-way valve (e.g., the valve V shown in FIGS. 12, 13, 20 and 22) in the filling port or by providing a closure mechanism (e.g., a cap).

In some embodiments of the invention a sealing mechanism is required to contain and seal the resin injection entry site while the composite solidifies. In some forms of the invention, the sealing mechanism is a mechanical valve (e.g., the valve V shown in FIGS. 12, 13, 20 and 22) and further is constructed of bioabsorbable polymers including some or all of those listed for the containment bag previously. The valve can have one or more seal mechanisms such as overlapping, hinged plates, or normally closed living hinges made of a compliant material. In other forms of the invention, the sealing mechanism can be a rapidly curing reactive polymer system with or without a high barrier to water entry. A combination of a mechanical system with a polymeric system can also be envisioned.

In some embodiments of the sealing mechanism, the mechanism has structural features that allow it to be releasably connected to a catheter or other delivery device. This separable valve connection (e.g., the valve V shown in FIGS. 12, 13, 20 and 22) allows for the bag to be delivered to an intramedullary space, sequentially filled with the composite components, then sealed upon separation and removal of the directing catheter.

Thus a preferred form of the sealing mechanism envisions a structure consisting of a series of two "duck-bill" valves separated by an open space of between 1 mm and 50 mm axially or greater. The structure has a separable connection to a catheter through and within which composite components are deliverable. Upon completion of delivery of the uncured resin components, the valves close due to applied vacuum, a normally closed design, or positive pressure from the resin with a portion of the resin filling the space between the two valves. The catheter is then separated from the bag, which remains in situ.

Reinforcing Elements

Figure 3:
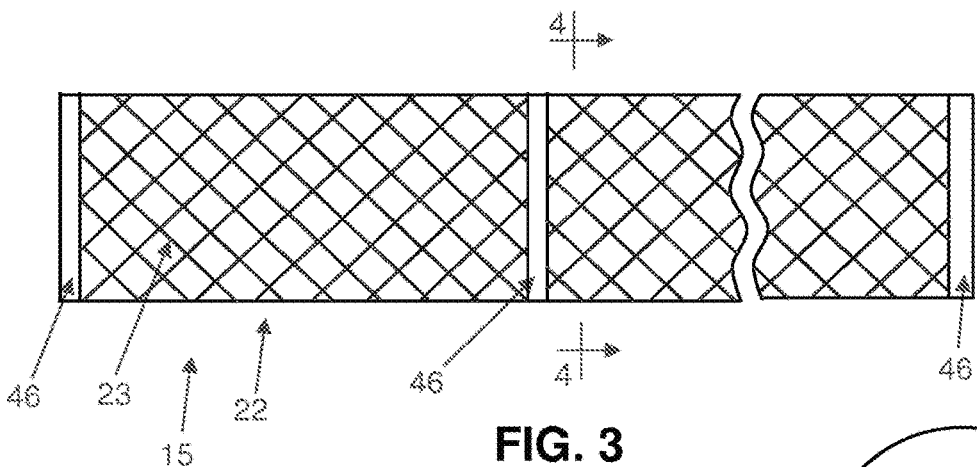
FIGS. 3 and 4 are schematic views of a concentric reinforcing tube that may be used to form the composite implant of FIGS. 1 and 2.
Figure 4:
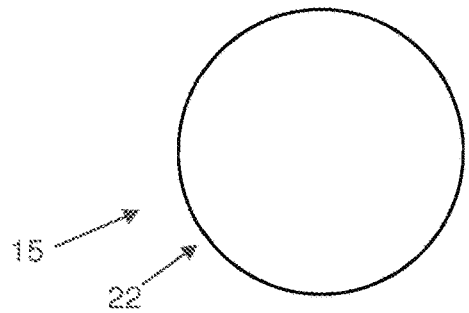
Figure 5:
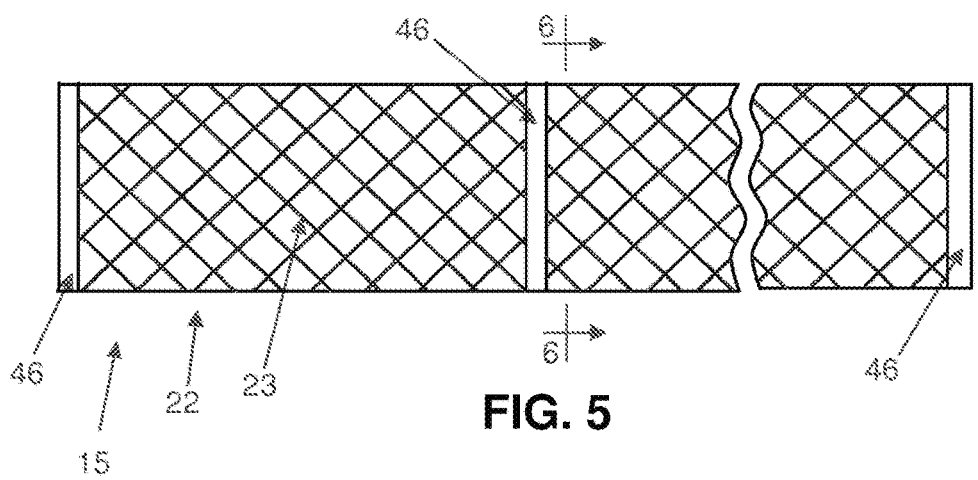
FIGS. 5 and 6 are schematic views of a rolled sheet that may be used to form the composite implant of FIGS. 1 and 2.
Figure 6:
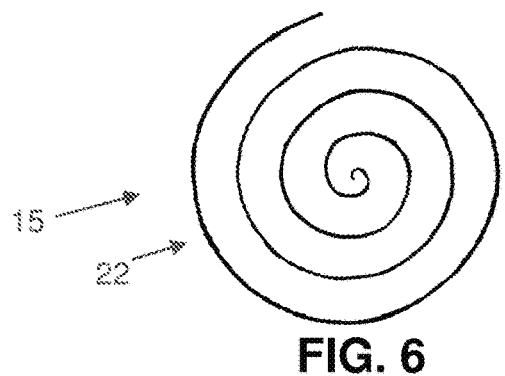
Figures 6A, 6B:
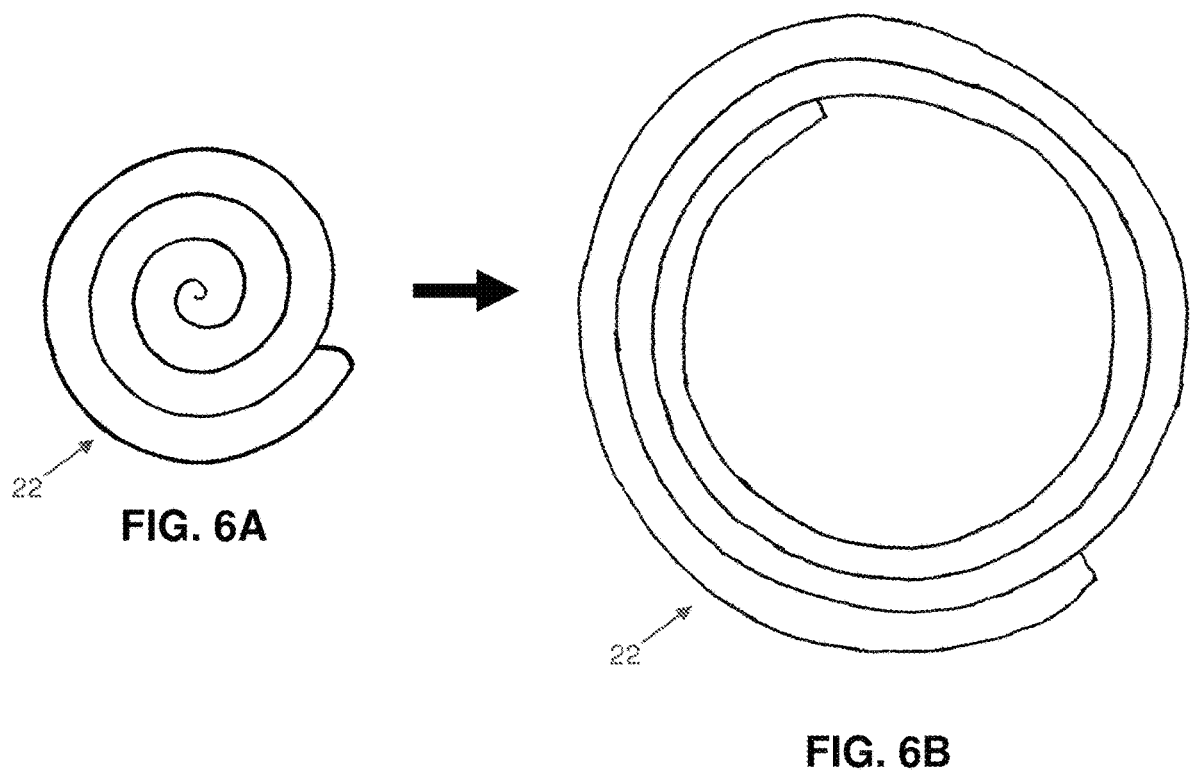
FIGS. 6A and 6B are schematic views showing how a flexible rolled reinforcing sheet may be radially compressed during delivery to the containment bag (FIG. 6A) and thereafter radially expanded (FIG. 6B) within the containment bag.
Figure 7:
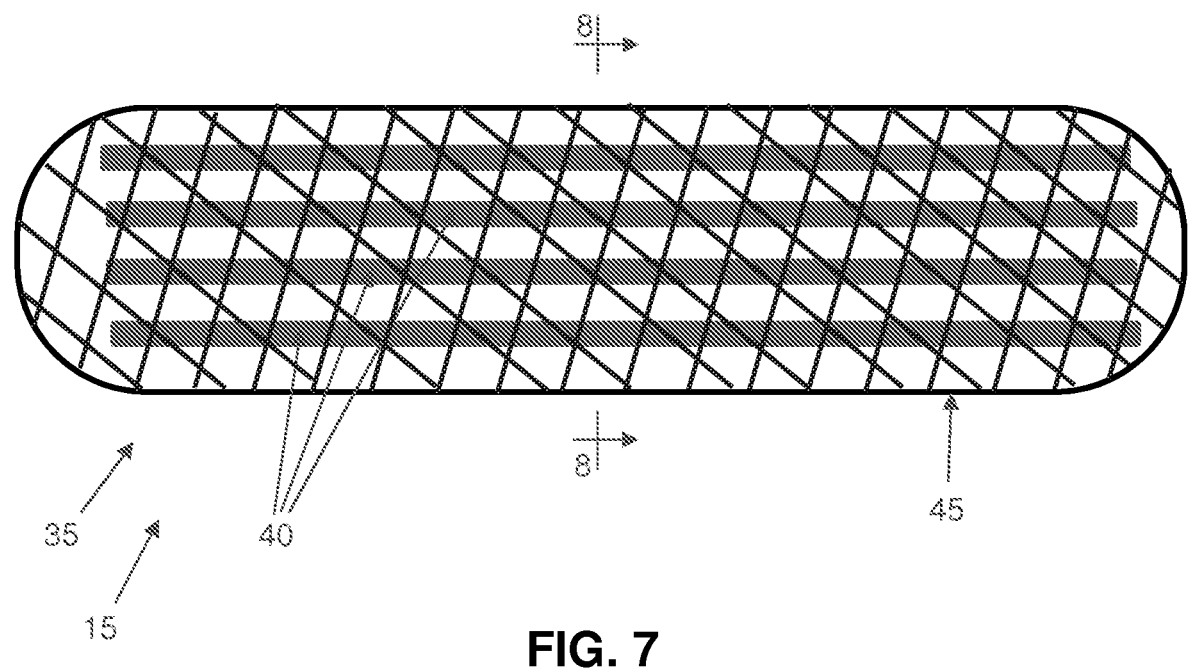
FIGS. 7 and 8 are schematic views of a flexible reinforcing rod that may be used to form the composite implant of FIGS. 1 and 2.
Figure 8:
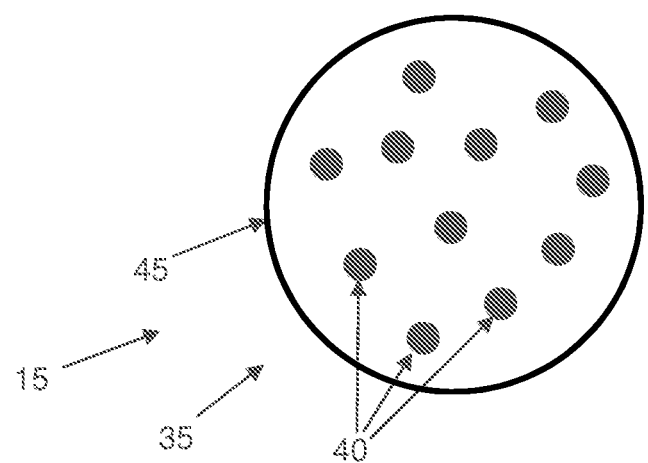
Figure 8C:
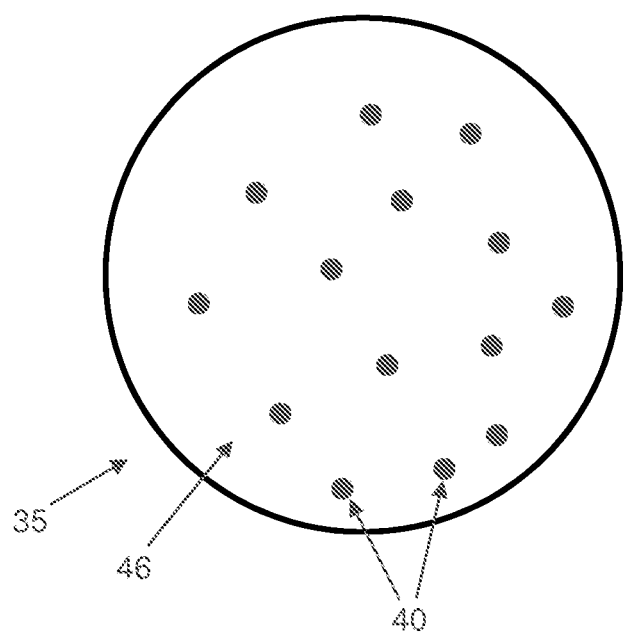
Figure 8D:
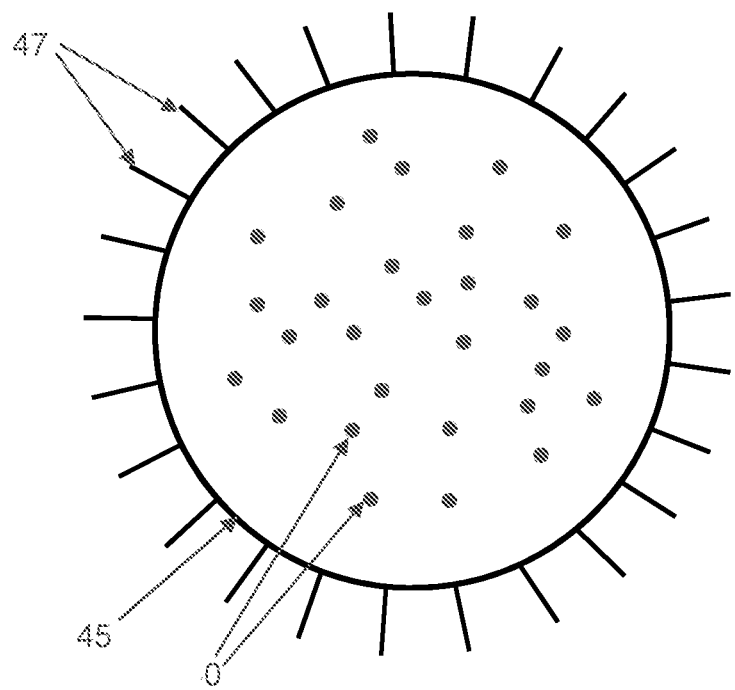

The one or more reinforcing elements 15 comprise (i) flexible reinforcing sheets 22 (which are preferably in the form of concentric tubes such as is shown in FIGS. 3 and 4 or rolled sheets such as is shown in FIGS. 5 and 6), with the flexible reinforcing sheets 22 comprising filaments 23 formed into a textile (i.e., woven, braided, knit, nonwoven, and/or otherwise worked so as to form the flexible reinforcing sheets 22) or incorporated into a film so as to form the flexible reinforcing sheets 22, (ii) flexible reinforcing rods 35 (FIGS. 7, 8, 8A, 8B, 8C and 8D), with the flexible reinforcing rods 35 comprising a plurality of filaments 40 which are held together by an outer sheath 45 (FIGS. 7 and 8) of a textile or film (which may or may not have the same composition and fiber orientation as the aforementioned flexible reinforcing sheets 22), or by a compacted (wound or compressed, etc.) connecting structure of a textile or film 45A (FIGS. 8A and 8B), or by a binder 46 (FIG. 8C) such as an adhesive, with or without surface projections 47 for improved integration with injectable matrix material 20, (iii) particulates (e.g., particles, granules, segments, whiskers, nanotubes, nanorods, etc.), or (iv) combinations of the foregoing. Where the one or more reinforcing elements comprise flexible reinforcing sheets and/or flexible reinforcing rods, the one or more reinforcing elements preferably have sufficient column strength to allow longitudinal delivery into the containment bag by pushing, and preferably have a configuration (e.g., textured outer surfaces, tapered ends, etc.) to facilitate movement past other reinforcing elements and/or intervening structures (e.g., catheter structures). The one or more reinforcing elements preferably can be introduced by means of a delivery catheter or sheath. Furthermore, where the one or more reinforcing elements comprise flexible reinforcing sheets (e.g., concentric tubes or rolled sheets) which are intended to be radially compressed during delivery to facilitate passage through a small opening (e.g., a catheter or surgical opening), the flexible reinforcing sheets (e.g., concentric tubes or rolled sheets) may comprise resilient elements 46 (e.g., resilient rings) to assist their subsequent return to an expanded state when positioned within the containment bag. The resilient elements may be thermosensitive or have a shape memory.

Thus, the composite implant of the present invention is formed from reinforcing elements that may be made up of fibers from various materials or "rods" of homogeneous or heterogeneous elements, configured in a solid, wound, braided, woven, or interlink-stacked manner. The rods may or may not be likewise interwoven by further braiding, weaving, or winding elements of similar or different fibrous elements.

The filaments, fibers, and particulates used to form the aforementioned reinforcing elements may be biodegradable or bioabsorbable, or non-biodegradable or non-bioabsorbable. By way of example but not limitation, suitable biodegradable or bioabsorbable materials include polyglycolide (PGA), glycolide copolymers, glycolide/lactide copolymers (PGA/PLA), glycolide/trimethylene carbonate copolymers (PGA/TMC), stereoisomers and copolymers of polylactide, poly-L-lactide (PLLA), poly-D-lactide (PDLA), poly-DL-lactide (PDLLA), L-lactide, DL-lactide copolymers, L-lactide, D-lactide copolymers, lactide tetramethylene glycolide copolymers, lactide/trimethylene carbonate copolymers, lactide/delta-valerolactone copolymers, lactide/epsilon-caprolactone copolymers, polydepsipeptide (glycine-DL-lactide copolymer), polylactide/ethylene oxide copolymers, asymmetrically 3,6-substituted poly-1,4-dioxane-2,4-diones, polyhydroxyalkanoates (PHA), poly(3-hydroxybutyrate-co-3-hydroxyvalerate) (PHBV), poly-β hydroxybutyrate (PHB), poly-4-hydroxybutyrate (P4HB), PHB/beta-hydroxyvalerate copolymers (PHB/PHV), poly-beta.-hydroxypropionate (PHP), poly-beta-dioxanone (PDS), polyhydroxyhexanoate (PHH), polyhydroxyoctanoate (PHO), poly-DELTA-valerolactone, poly-DELTA-caprolactone, methyl methacrylate-N-vinyl pyrrolidone copolymers, polyester amides, oxalic acid polyesters, citric acid polyesters, polydihydropyrans, polypeptides from alpha-amino acids, poly-beta-maleic acid (PMLA), poly-beta-alkanoic acids, polyethylene oxide (PEO), silk, collagen, derivatized hyaluronic acid and chitin polymers, and resorbable metals, resorbable metal alloys, resorbable ceramics, and phosphate, borate, and silicate soluble glasses containing other inorganic ions such as Fe, Ca, Sr, Zn, B, Mg, K, Mn, Ce, etc. By way of further example but not limitation, suitable non-biodegradable or non-bioabsorbable materials include polyolefins, polyamides, polyesters and polyimides, polyetheretherketone (PEEK), polyetherketoneketone (PEKK), glass, ceramic, metal, silk, metal-clad fiber, and carbon fiber.

As will hereinafter be discussed, the one or more reinforcing elements 15 are selected by the physician so as to provide the composite implant with the desired size and mechanical properties, e.g. stiffness and strength. Thus, and as will hereinafter be discussed, the physician may select from a variety of different reinforcing elements, each having a particular composition and length, and preferably deliver those reinforcing elements sequentially to the patient, whereby to provide the composite implant with the desired size and attributes of stiffness and strength.

In one preferred form of the invention, the one or more reinforcing elements 15 comprise from about 5% to 85% (by volume) of the composite implant, typically at least 20% (by volume) of the composite implant.

In another embodiment, the reinforcing properties of the one or more reinforcing elements 15 may be modified by changing the materials, dimensions, shape, and surface characteristics of the fibers, filaments, and particulates.

In another embodiment, the reinforcing properties of the one or more reinforcing elements 15 may be modified by changing the orientation, volume, twist, and angle of the fibers and filaments within the reinforcing elements. In preferred constructions, the fibers and filaments are typically set at an acute angle to intersecting fibers and filaments in order to strengthen the reinforcing structure, but the angle may be any angle between 0 degrees and 90 degrees.

In another embodiment, the properties of the composite implant may be modified by changing the orientation of one or more of the reinforcing elements 15, and/or by changing the volume of one or more of the reinforcing elements 15.

It will be appreciated that the properties of the composite implant may be modified by changing the layup or selection of one or more of the reinforcing elements 15.

It will also be appreciated that the reinforcing properties, and degradation profiles, of the one or more reinforcing elements 15 may be modified by changing the material, dimensions, shape, orientation, volume, and surface features of the fibers, filaments, and/or particulates used to form the one or more reinforcing elements 15.

Where the reinforcement elements comprise a textile, its reinforcing properties and degradation profile may be modified by changing the materials, orientation, length, shape, volume, twist, and angle of the fibers and filaments within the textile of the reinforcing elements. The fibers and filaments in a textile of a reinforcing element are preferably set at an acute angle to intersecting fibers and filaments, but the angle may vary between 0 degrees and 90 degrees or random.

It will be appreciated that the properties of the composite implant may be modified by changing the layup or selection of one or more of the reinforcing elements.

It will also be appreciated that the reinforcing properties, and the degradation profiles, of the one or more reinforcing elements may be modified by changing the material, dimensions, shape, orientation, volume, and/or surface features of the fibers, filaments, and/or particulates used to form the one or more reinforcing elements.

The shape of the reinforcement elements is generally important. For textiles, interwoven or braided materials can be formed as space fillers and skeletons for the composite implant. The shapes can be tailored for the intended use, for example, triangular- or ribbon-shaped. A triangular braided rod can be used as the reinforcement backbone of a composite implant. The triangular shape (i.e., triangular cross-section) gives advantages over cylindrical shapes (i.e., cylindrical cross-section) in that the triangular shape is more applicable to a triangular intramedullary canal, additionally, each flat providing a plane of contact to spread impact force rather than a point load as occurs with a circular configuration. Additionally, the nesting of flat against flat sides of the triangular shape provides a large surface area for inter-rod binding by the resin. The triangular shape allows for numerous configurations such as horizontal inter-locking of greater than two triangular rods resulting in a flat rod-like trapezoidal composite implant shape. This shape provides manufacturing flexibility, inasmuch as a single back-bone braid could be configured into multiple final products. The triangular shape allows for very tight groupings of materials that allow for very high fiber volumes not possible with circular braids or other reinforcement materials which will always tend to have larger gaps between parallel axial reinforcement elements.

It should be noted that the use of multiple axially-oriented reinforcement elements made from textiles can be inter-locked, either with a surrounding binding fiber or with interwoven fiber elements, so as to increase resistance to catastrophic breakdown. Many current non-metallic implants fail due to catastrophic shear and compressive fracturing. The use of interlocked textiles in sheets or intrawoven axial reinforcements can ensure failure occurs in a non-catastrophic yield rather than shear fracture mode as with metal implants. This is advantageous as an orthopedic repair element. Additionally, it is known that composite materials can be superior to metals in response to chronic dynamic loading, i.e., resisting fatigue.

The reinforcing fibers or braids can also be pre-cured with polymer matrix to form pins or rods, which can then be used for the composite implant. Forming pre-cured pins or rods can facilitate their handling and can prevent or retard degradation of the glass fiber in moisture.

Sizing.

The high modulus fiber may have a surface coated with a sizing agent or primer that provides additional adhesion between an acrylic resin injectable matrix material and the high modulus fiber, and can optionally act as a secondary catalyst for the polymerization of the acrylic monomers. In addition, the high modulus fiber may be surface coated with an amino functional material selected from at least one of the following materials: amino silanes, lysine, polyamines, amino acids and polyamino acids.

The reinforcement fibers can be cleaned or surface oxidized using various means described in the literature including plasma treatment, corona treatment, ozone treatment, and acidic/basic treatment. Such treatments can also be used to introduce specific chemical moieties, such as hydroxyl groups, on the surface of the fibers that can that react or provide improved adhesion with the polymer matrix.

Compatibility among the specific components that comprise a composite structure is essential in order to ensure optimal interfacial bonding, mechanical properties, physical properties, and osseointegration. Compounds known as coupling agents or compatibilizers, which may be incorporated into the components of the composite implant, serve to enhance the chemical bonding between the specific components of the composite implant. In a preferred embodiment, the interfacial bond strength between the containment bag, reinforcing elements, injectable matrix material, and bone can be enhanced through the addition of a variety of compatibilizers, e.g., calcium phosphate, hydroxyapatite, calcium apatite, fused-silica, aluminum oxide, apatite-wollastonite glass, bioglass, compounds of calcium salt, phosphorus, sodium salt and silicates, maleic anhydride, diisocyanate, epoxides, silane, and cellulose esters. These agents may be incorporated into, and/or applied to, the components of the composite implant through a number of methods, e.g., plasma deposition, chemical vapor deposition, dip coating, melt-blending, spin or spray-on. A specific example is the application of a silane coupling agent to glass fiber reinforcement in order to increase its interfacial bonding strength with the injectable matrix material. Another example is the vapor deposition of calcium phosphate onto the inner surface of the containment bag such that the bonding between the injectable matrix material and the containment bag is enhanced. In order to increase the compatibility between the containment bag and bone that it is supporting, dip-coating the exterior of the containment bag with an osseoconductive material (such as fused-silica with aluminum oxide) will improve their adhesion to each other and accelerate osseointegration.

The fibers may be sized with a resorbable metal layer, such as magnesium, silver, nickel, titanium or metal alloys such as magnesium calcium alloys. Such coatings can be applied via vapor coating, sputtering, atomic layer deposition, chemical vapor deposition, or electroplating and electroless plating. Another possible coating can be ceramic coatings on the fibers. Such coatings can be made by the surface reaction of ethyoxysilanes such as tetraethoxysilane, methyltriethoxysilane, dimethyldiethoxysilane, or trimethylethoxysilane; polycarbosilane, or polysilazanes such as perhydropolysilazane or polysilizane modified polyamines.

Another possible approach for sizing utilizes inorganic salts such as metal phosphates. This approach for sizing is similar to the pretreatment process of metals, wherein acids are used to corrode the metal and thus form metal salt on the surface which delays any further attack. Typically phosphate salts of iron, calcium, magnesium, zinc and nickel, etc. are used. The sizing can be applied to phosphate glass fibers by immersion in a suitable metal-salt solution which yields inert phosphate salts that are insoluble in water. This process is self-limiting, as the reaction takes place only as long as phosphate ions are released from the glass surface. The reaction can take place in a reactive medium such as an alcohol or glycol. Mixture of salts is preferred due the formation of smaller crystal sizes. This process could also be combined with an organic pretreatment. This combination of salt/organic pretreatment could also act as an adhesion promoter. After reaction, the glass fibers can be rinsed and/or vacuum dried. Multiple iteration can be performed with the same compound or different salts. It is also possible to use only a metal phosphate, and diffuse some metal ions into the glass fiber and obtain a metal clad fiber.

Those skilled in the art will recognize still other ways to modify the properties of the composite implant in view of the present disclosure.

It should also be appreciated that reinforcing elements 15 may be formed out of one or more of the materials used to form containment bag 10 and/or one or more of the materials used to form injectable matrix material 20, appropriately processed so as to provide the functional requirements of reinforcing elements 15.

Injectable Matrix Material

The injectable matrix material 20 is preferably polymeric and is preferably biodegradable. The injectable matrix material 20 is designed to be polymerized in situ but may be pre-formed prior to the application. The matrix material is preferably a multi-component polymer system that is mixed immediately prior to introduction into the patient. Optionally, the injectable matrix material 20 may contain a biocompatible solvent, with the solvent reducing viscosity so as to allow the matrix material to be injected, and with the solvent thereafter rapidly diffusing from the composite implant so as to facilitate or provide stiffening of the composite implant 5. The solvent may also be used to alter the porosity of the injectable matrix material 20.

In a preferred embodiment of the present invention, polyurethanes are utilized as the injectable matrix material, although other suitable chemistry systems will be apparent to those skilled in the art. The polyurethanes are produced through the reaction of a difunctional or multifunctional isocyanate with a difunctional or multifunctional compound containing an active hydrogen, including water, hydroxyl materials and amines. The urethane polymer matrix may comprise at least two individual components that are mixed together to initiate the curing reaction, wherein a first component contains isocyanate functionalities and a second component contains active hydrogen functionalities capable of reacting with the isocyanate functionalities so as to form at least one from the group consisting of urethane, urea, biuret and allophonate groups during the crosslinking reaction.

The first component may be selected from the group consisting of a diisocyanate molecule, a triisocyanate molecule, a polyisocyanate molecule having at least two isocyanate groups per molecule, an isocyanate capped polyol having at least two free isocyanate groups per molecule, an isocyanate capped polyether polyol having at least two free isocyanate groups per molecule and an isocyanate capped polyester polyol having at least two free isocyanate groups per molecule. Suitable isocyanates useful in the practice of this invention include, but are not limited to, aromatic diisocyanates such as 1,2 and 1,4 toluene diisocyanate and blends, 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyldimethylmethane diisocyanate, dibenzyl diisocyanate, naphthylene diisocyanate, phenylene diisocyanate, xylylene diisocyanate, methylene diphenyl diisocyanate (MDI) and polymeric MDI having an isocyanate functionality from about 2.2 to about 2.8 isocyanate groups per molecule, 4,4'-oxybis(phenylisocyanate) or tetramethylxylylene diisocyanate; aliphatic diisocyanates such as tetramethylene diisocyanate, hexamethylene diisocyanate, dimethyl diisocyanate, lysine diisocyanate, methyl lysine diisocyanate, lysine triisocyanate, 2-methylpentane-1,5-diisocyanate, 3-methylpentane-1,5-diisocyanate or 2,2,4-trimethylhexamethylene diisocyanate; and alicyclic diisocyanates such as isophorone diisocyanate, cyclohexane diisocyanate, hydrogenated xylylene diisocyanate, hydrogenated diphenylmethane diisocyanate, hydrogenated trimethylxylylene diisocyanate, 2,4,6-trimethyl 1,3-phenylene diisocyanate.

Or the first component may be a polyol isocyanate having a weight average molecular weight from about 200 to about 10,000.

Or the first component may be a blend of diisocyanate or triisocyanate molecules with a polyol capped isocyanate having two, three or four isocyanate groups per molecule in a ratio of about 1:99 percent by weight to about 99:1 percent by weight of the total isocyanate component and has a viscosity at 25 degrees C. from about 250 cps to about 5,000 cps.

The present invention comprises the use of these same multi-functional isocyanates with multifunctional amines or multifunctional substituted amines, multifunctional ketimines, multifunctional aldimines, isocyanurates or biurets. By way of example but not limitation, such multifunctional amines may include hexamethylene diamine, isophorone diamine, and lysine. Also trifunctional isocyanates such as lysine triisocyanates. Examples of substituted amines may include N-substituted diaspartic acid derivatives. Examples of multifunctional ketimines and aldimines may be made from the multifunctional amines mentioned previously and methyl isobutyl ketone or isobutyraldehyde.

The second component may be produced by the reaction product of a diamine, triamine or tetramine component with an activated vinyl component selected from the group consisting of dialkyl maleate, dialkyl fumarate, an acrylic acid ester and vinyl ester, wherein the reaction ratio is from about one equivalent of amine functionality to about one equivalent of vinyl functionality to about four equivalents of amine functionality to about one equivalent of vinyl functionality.

Or the second component may be a blend of a polyol component and an aspartate molecule having from about 1% to about 99% polyol component and from about 99% to about 1% aspartate, wherein at least one of the polyol component and the aspartate molecule has a functionality towards isocyanate of at least 2.1 active hydrogen groups per diisocyanate molecule and a viscosity from about 250 cps to about 5000 cps at 25 degrees C.

Or the second component may be selected from the group consisting of a polyol having at least two hydroxyl groups and up to four hydroxyl groups per molecule where the hydroxyl groups are primary or secondary hydroxyls, a polyether polyol having at least two hydroxyl groups and up to four hydroxyl groups per molecule, a polyester polyol having at least two hydroxyl groups and up to four hydroxyl groups per molecule where the polyester is formed by the reaction of a diol or trio with a diacid, a polyester polyol having at least two hydroxyl groups and up to four hydroxyl groups per molecule where the polyester is formed by the reaction of hydroxyacid which is then endcapped with a diol or triol, an aspartate molecule, an amine molecule having from at least two amine groups to four amine groups per molecule where the amine groups are a primary or secondary amines, alkoxylated amines having at least two terminal amine groups per molecule, and a compound containing at least two of the following: aliphatic primary hydroxyl, aliphatic secondary hydroxyl, primary amine, secondary amine and carboxylic acid groups within the one molecule.

Or the polyester polyol is selected from a reaction mixture primarily of adipic acid with diethylene glycol, ethylene glycol or butane diol.

Or the second component can comprise a biodegradable crosslinker with hydroxyl functionality such as 3-hydroxy-N,N-bis(2-hydroxyethyl)butanamide, or a blend of polyols along with the biodegradable crosslinker.

When a non-biodegradable implant is desired, the aromatic isocyanates are generally favored. When a biodegradable implant is desired, the aliphatic isocyanates are generally favored. In an embodiment of this invention, the aliphatic isocyanates are preferred.

In a preferred embodiment of this invention, the isocyanate component is reacted with a polyol to produce a polyurethane. Suitable polyols include, but are not limited to, diols and triols of polycaprolactone, poly(caprolactone-co-lactide) and poly(caprolactone-co-lactide-co-glycolide). Suitable dihydroxy compounds which may be utilized in the practice of this invention include, but are not limited to, ethylene glycol, propylene glycol, butylene glycol, hexylene glycol and polyols including polyalkylene oxides, polyvinyl alcohols, and the like. In some embodiments, the polyol compounds can be a polyalkylene oxide such as polyethylene oxide ("PEO"), polypropylene oxide ("PPO"), block or random copolymers of polyethylene oxide (PEO) and polypropylene oxide (PPO). Higher functional polyol compounds are also useful and can include glycerin, 1,2,4-butanetriol, trimethylol propane, pentaerythritol and dipentaerythritol, 1,1,4,4-tetrakis(hydroxymethyl)cyclohexane. Also polyols such as sugars or starch. Other useful polyols can include triethanol amine and N,N,N',N'-Tetrakis (2-hydroxyethyl)ethylenediamine.

The polyol materials discussed above may be used alone or, optionally, as mixtures thereof. The foregoing materials are merely examples of useful components for producing polyurethanes and should not be viewed as a limitation of the present invention. These higher functional polyol materials will produce highly crosslinked polyurethanes with high hardness and stiffness.

In preferred embodiments, the multifunctional hydroxyl material may include at least one bioabsorbable group to alter the degradation profile of the resulting branched, functionalized compound. Bioabsorbable groups which may be combined with the multifunctional compound include, but are not limited to, groups derived from glycolide, glycolic acid, lactide, lactic acid, caprolactone, dioxanone, trimethylene carbonate, 3-hydroxypropionic acid (3HP), 4-hydroxybutyrate (4HB), 5-hydroxyvalerate (5HV), 3-hydroxyhexanoate (3HH), 6-hydroxyhexanoate (6HH), 3-hydroxyoctanoate (3HO), and combinations thereof. For example, in one embodiment, the multifunctional compound may include trimethylol propane in combination with dioxanone and glycolide. Methods for adding bioabsorbable groups to a multifunctional compound are known in the art. Where the multifunctional compound is modified to include bioabsorbable groups, the bioabsorbable groups may be present in an amount ranging from about 50 percent to about 95 percent of the combined weight of the multifunctional compound and bioabsorbable groups, typically from about 7 percent to about 90 percent of the combined weight of the multifunctional compound and bioabsorbable groups.

The multifunctional compound can have a weight (average molecular weight) ranging from about 50 to about 50000, typically from about 100 to about 30000, and preferably between about 150 to about 5000, and typically possesses a functionality ranging from about 2 to about 6.

In a preferred embodiment, the polycaprolactone diols and triols provide polyurethanes that are biodegradable.

The isocyanate is reacted with a polyol to produce a prepolymer. Methods for endcapping the polyol with an isocyanate are known to those skilled in the art. For example, a polycaprolactone diol may be combined with isophorone diisocyanate by heating to a suitable temperature ranging from about 55 degrees C. to about 80 degrees C., typically about 70 degrees C. The resulting diisocyanate-functional compound may then be stored until combined with additional polyol to form the final polyurethane product.

Reaction of the urethane prepolymer with polyol to form the final polyurethane product generally requires a catalyst to provide convenient working and cure times. Polyurethane catalysts can be classified into two broad categories, amine compounds and organometallic complexes. They can be further classified as to their specificity, balance, and relative power or efficiency. Traditional amine catalysts have been tertiary amines such as triethylenediamine (TEDA, also known as 1,4-diazabicyclo[2.2.2]octane or DABCO, an Air Products's trademark), dimethylcyclohexylamine (DMCHA), and dimethylethanolamine (DMEA). Tertiary amine catalysts are selected based on whether they drive the urethane (polyol+isocyanate, or gel) reaction, the urea (water+isocyanate, or blow) reaction, or the isocyanate trimerization reaction (e.g., using potassium acetate, to form isocyanurate ring structure). Since most tertiary amine catalysts will drive all three reactions to some extent, they are also selected based on how much they favor one reaction over another.

Another useful class of polyurethane catalysts are the organometallic compounds based on mercury, lead, tin (dibutyl tin dilaurate), bismuth (bismuth octanoate), titanium complexes, zirconium complexes, zinc complexes (imidazole complexed zinc), and iron complexes. Dibutyl tin dilaurate is a widely used catalyst in many polyurethane formulations. Stannous octoate is another catalyst that may be used.

Another useful catalyst is 1,8-diazabicyclo[5.4.0]undec-7-ene (DBU).

In the practice of this invention dibutyl tin dilaurate is a favored catalyst at concentrations below 0.5% and more preferably at concentrations below 0.2% by weight.

The urethane polymer matrix may be crosslinked.

The crosslinked urethane polymer matrix may be configured to start degrading in the body within about 1 month to about 36 months after implantation in the body.

The crosslinked urethane polymer matrix may be configured to lose at least 50% of its original mechanical strength after 6 months in the body.

The crosslinked urethane polymer matrix may be configured to lose at least 80% of its original mechanical strength after 12 months in the body.

In a preferred embodiment of this invention, the composite implant is created via the injection of a matrix material, preferably polymeric, through and around the reinforcing elements that may be a series of braided fibers, axial rods, bundled rods, bundled braided rods or other such configurations that conform to previous descriptions. The maximum compressive and flexural modulus of the composite implant is that of the theoretical compressive and flexural modulus of a composite implant formed completely out of reinforcing elements, the minimum compressive and flexural modulus of the composite implant is that of the theoretical compressive and flexural modulus of a composite implant formed completely out of injectable matrix material. The final compressive and flexural modulus of the composite material is directly related to the percent composition of fiber volume and will lie between the two values. Additionally, in one embodiment, the reinforcing elements may be braided into geometric formations which further increase or decrease the mechanical properties of the composite implant. As an example, a composite implant with all axial reinforcement elements will have highest resistance to tension and compression, while a composite implant with braided reinforcement elements with no axial reinforcement, but biased reinforcement at approximately 45° to the axis of the composite implant, would be strong in flexural modulus but not as strong in compression. As another example, woven sheets of materials used as reinforcement elements may be designed with differing weave configurations to achieve similar ends.

It should also be appreciated that injectable matrix material 20 may be formed out of one or more of the materials used to form containment bag 10 and/or one or more of the materials used to form reinforcing elements 15, appropriately processed so as to provide the functional requirements of injectable matrix material 20.

In one preferred form of the invention, the injectable matrix material comprises a polymer comprising a blend of (i) one or more reactants with a least two functional groups 20 to 95% by weight, (ii) a low molecular weight functional modifier 0.1 to 30% by weight, and (iii) a poly functional aliphatic or cycloaliphatic isocyanate crosslinker in a stoichiometric ratio with reactants from 0.8 to 1.3. The matrix polymer may, optionally, also include (iv) a catalyst. The un-crosslinked blend has a glass transition temperature of between of about 170° K to 250° K (i.e., −103.2° C. to −23.5° C.).

The first component (i.e., one or more reactants with a least two functional groups) preferably comprises (a) hydroxyl functional reaction products of a C2 to C16 aliphatic or cycloaliphatic or heterocyclic diols or triols or blends of these polyols with a saturated or unsaturated C2 to C36 aliphatic dicarboxylic or tricarboxylic acid, anhydrides or lactones and/or lactides and/or glycolides and/or carbonates or blends of these carboxylic acids, or (b) amine functional aspartic acid ester, or (c) CH-active compounds, or blends of the foregoing.

Examples of some of the typical dicarboxylic acid and polyols to prepared polyester polyols useful in the present invention are shown in U.S. Patent Application Publication No. 2013/0171397 and in U.S. Pat. Nos. 2,951,823 and 2,902,462.

The second component (i.e., a low molecular weight functional modifier) preferably comprises an aliphatic or cycloaliphatic or heterocyclic diol with C2 to C12 carbons.

The third component (i.e., a poly functional aliphatic or cycloaliphatic isocyanate crosslinker) preferably comprises an isocyanurate (trimer), iminooxadiazine dione (asymmetric trimer), biuret, allophanate or uretdione (dimer) derivative (with an average functionality of between 2.0 to 4) of an C4 to C15 aliphatic or cycloaliphatic diisocyanate or lysine diisocyanate, or a C4 to C15 aliphatic or cycloaliphatic diisocyanate or lysine diisocyanate. The crosslinked network has a crosslink density with an average molecular weight between crosslinks of between 200 to 500.

The fourth (optional) component (i.e., a catalyst) is preferably selected from the group of metals such as bismuth, potassium, aluminum, titanium, zirconium compounds or a t-amine, or organo-tin compounds.

The foregoing polymer blend is reactive at a temperature of between 5° C. and 150° C., or 10° C. to 70° C., or 10° C. to 50° C. to form a rigid polymer matrix with a Tg (glass transition temperature) between 273.2° K (0° C.) and 423° K (150° C.), more preferably between 273° K (0° C.) and 373° K (100° C.), and more preferably between 313° K (40° C.) and 343° K (70° C.), and more preferably greater than 303° K (30° C.), and is biodegradable over a maximum 5 year period and more preferably within a 3 year period.

The molar ratio of the above matrix is 0.8 to 1.3 reactant functional group to isocyanate functional group.

The crosslinked network is formed at a temperature of between 20° C. to 60° C. within a time period of less than 24 hours.

Optionally, the matrix may also include a non-reactive polyester plasticizer in the amount of 0-30% of the weight of the matrix. The plasticizer for the matrix may consist of non-reactive aliphatic polyesters as shown in U.S. Pat. No. 5,047,054 among others.

The above glass transition temperature Tg of the reactant can be obtained by measurements or also by calculation using the William Landel Ferry Equation (WLF) M. L. Williams, R. F. Landel and J. D. Ferry, J. Am. Chem. Soc. 77, 3701 (1955).

Above aspartic acid ester reactants are described in U.S. Pat. Nos. 7,754,782; 5,847,195; 5,126,170; 5,236,741; 5,243,012; 5,489,704; 5,516,873; 5,580,945; 5,597,930; 5,623,045; 5,633,389; 5,821,326; 5,852,203; 6,107,436; 6,183,870; and 6,355,829, among others.

The above CH active compounds are the malonic acid ester of above diols or triols or an acetoacetic ester of the above diols or triols.

Additions to Injectable Matrix Material

If desired, the injectable matrix material 20 may also comprise a bioactive or insoluble filler material, a therapeutic agent, and/or an agent to enhance visibility while imaging the composite implant.

Fillers.

The injectable matrix material may include a filler in the form of biocompatible, insoluble and/or osteoconductive particles or short fibers. The first or primary filler, preferably in the form of particles, may also provide porosity, bone ingrowth surfaces and enhanced permeability or pore connectivity or resistivity to water permeation. One suitable particulate filler material is tricalcium phosphate, although other suitable filler materials will be apparent to those skilled in the art such as orthophosphates, monocalcium phosphates, dicalcium phosphates, tricalcium phosphates, tetracalcium phosphates, amorphous calcium phosphates and combinations thereof. Also biodegradable/bioresorbable glasses can be utilized as a filler.

The filler particles may comprise a degradable polymer such as polylactic acid, polyglycolic acid, polycaprolactone, hydroxybutyrate, hydroxypropionic acid, hydroxyhexanoate, and co-polymers thereof. The particles may also comprise degradable polymer containing one or more inorganic fillers.

In one embodiment the inorganic filler particles have mean diameters ranging from about 1 micron to about 20 microns and lengths of 1 micron to 500 microns. The inorganic filler particles can have different shapes, including spherical, platelet-shaped, isotropic or anisotropic, fibers including nanofibers, rods, nanotubes, and nanorods.

In another embodiment the porosity and compressive properties of the matrix material may be modified by using additional fillers that may be inorganic, organic or another suitable biocompatible material. Such refinements include the addition of particles having mean diameters ranging from about 10 microns to about 500 microns or a mean diameter of less than 1 micron. In certain matrix materials the additional filler materials may be provided in one or more size distributions.

The composite implant can become porous after implantation so as to aid the resorption and bone healing process. This porosity can be generated by various mechanisms including the preferential resorption of filler, such as calcium sulfate or α-tricalcium phosphate, bioglass or of a polymeric component. Alternatively, the formulation can include a biocompatible solvent such as DMSO that is leached out of the implant post implantation. The pores are preferably 100 μm in diameter with interconnectivity to allow bone ingrowth.

The composite implant may also include an additional porogen. In one form of the invention, the porogen is sugar or a polysaccharide, such as dextran, but other biocompatible porogens will be apparent to those skilled in the art such as crystalline materials in the form of soluble salts.

In another embodiment of the present invention, the filler, either inorganic or polymeric, may be present in combined amount ranging from about 10 to about 50 wt % of the matrix composition. In certain cases it may be desirable to have the filler content over 50 wt %. If a porogen is added, it will preferably be present in an amount ranging from about 15 to about 50 wt %.

Therapeutics Agents.

The inclusion of a therapeutic agent in the injectable matrix material, or in one or more of the reinforcing elements, is contemplated in the practice of this invention. Therapeutic agents can include agents that promote bone formation, or for relief of pain. Agents may include, but are not limited to, parathyroid hormone, vitamin D, calcitonin, calcium, PO4, non-steroidal anti-inflammatory drugs (NSAIDS) such as, but not limited to, acetaminophen, salicylates (aspirin, diflunisal, salsalate), acetic acid derivatives (indomethacin, ketorolac, sulindac etodolac, diclofenac, nabumetone), propionic acid derivatives (ibuprofen, naproxen, flurbiprofen, ketoprofen, oxaprozin, fenoprofen, loxoprofen), fenamic acid derivatives (meclofenamic acid, mefenamic acid, flufenamic acid, tolfenamic acid), oxicam (enolic acid) derivatives (piroxicam, meloxicam, tenoxicam, droxicam, lornoxicam, isoxicam), arylalkanoic acid derivatives (tolmetin); selective COX-2 inhibitors (celecoxib, rofecoxib, valdecoxib, parecoxib, lumiracoxib, etoricoxib, firocoxib); steroids such as, but not limited to, corticosteroids (hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, dexamethasone, fluocortolone, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, or fluprednidene acetate); immune selective anti-inflammatory derivatives (ImSAIDs) such as, but not limited to, submandibular gland peptide T (SGp-T) and derivatives phenylalanine-glutamine-glycine (FEG) and its D-isomeric form (feG); narcotic compositions such as, but not limited to, buprenorphine, butorphanol, codeine, hydrocodone, hydromorphone, levorphail, meperidine, methadone, morphine, nalbuphine, oxycodone, oxymorphone, pentaxocine, or propoxyphene; other analgesic compositions such as, but not limited to, tramadol, or capsaicin; local anethetics (including short term acting anesthetics) such as, but not limited to, benzocaine, dibucaine, lidocaine, or prilocaine; bisphosphonates, or combinations of any of the above.

Therapeutic agents delivered locally can use a carrier vehicle to provide a protective environment, provide target delivery to cells or within cells, provide locally delivery, timed delivery, staged delivery and/or use delivery technology know in the art.

The therapeutic agents can also include bone growth activating factors, such as bone morphogenetic proteins (BMPs), FGF (fibroblast growth factor), VEGF (vascular endothelial growth factor), PDGF (platelet derived growth factor), or PGE2 (prostaglandin E2). Bone morphogenetic proteins can include BMP1, BMP2, BMP3, BMP4, BMP5, BMP6, BMP7, BMP8a, BMP8b, BMP10, or BMP15.

The therapeutic agents can also include inorganic material processed by the body as a vitamin such as Fe, Ca, P, Zn, B, Mg, K, Mn, Ce, Sr. These elements are built into a predictably solubilizing component of the composite tuned for a consistent release.

Agent to Enhance Visibility.

It is also possible for the injectable matrix material to include one or more particles or liquid agents to enhance visibility while imaging the composite implant. By way of example but not limitation, where the physician may be using fluoroscopy to view the bone being treated and the composite implant, the injectable matrix material may include bismuth oxychloride, bismuth subcarbonate, barium, barium sulfate, ethiodol, tantalum, titanium dioxide, tantalumpentoxide, tungsten, strontium carbonate, strontium halides platinum, titanium, silver, gold, palladium, iridium, osmium, copper, niobium, molybdenum, strontium, strontium salts and gallium, iodine substituted compounds/polymers, and/or alloys such as nickel-titanium, nickel-manganese-gallium, platinum-iridium, platinum-osmium to enhance the visibility of the injectable matrix material under fluoroscopy.

Features of the Composite Implant

In a preferred embodiment of the invention, the composite implant is created via the introduction of the injectable matrix material, preferably polymeric, through and around the reinforcing elements, which may comprise a plurality of braided fibers, axial rods, bundled rods, bundled braided rods or other such configurations. The matrix material and reinforcing elements may be surrounded by a barrier which may be used to regulate the rate at which water contacts the matrix material and reinforcing elements.

In one preferred form of the invention, there is provided a novel composite comprising (i) a barrier (which may be a containment bag or coating) which is water permeable and which contains hydrolyzable sites so that the barrier will break down over time when placed in an aqueous environment (e.g., water, the body, etc.); (ii) a flowable/settable matrix which is hydrolyzable so that the matrix will break down over time when contacted by an aqueous environment; and (iii) reinforcing elements which are disposed within the flowable/settable matrix and which, when they come into contact with an aqueous environment, break down and give off catalysts which modify (e.g., increase) the hydrolysis of the matrix material. Thus, in this form of the invention, the barrier provides a means for regulating the degradation of the matrix material, and the reinforcing elements provide a means for modifying (e.g., increasing) the hydrolysis of the matrix material.

The maximum compressive and flexural modulus of the composite implant is that of the theoretical compressive and flexural modulus of a composite implant formed completely out of reinforcing elements, and the minimum compressive and flexural modulus of the composite implant is that of the theoretical compressive and flexural modulus of a composite implant formed completely out of injectable matrix material.

Figure 28:
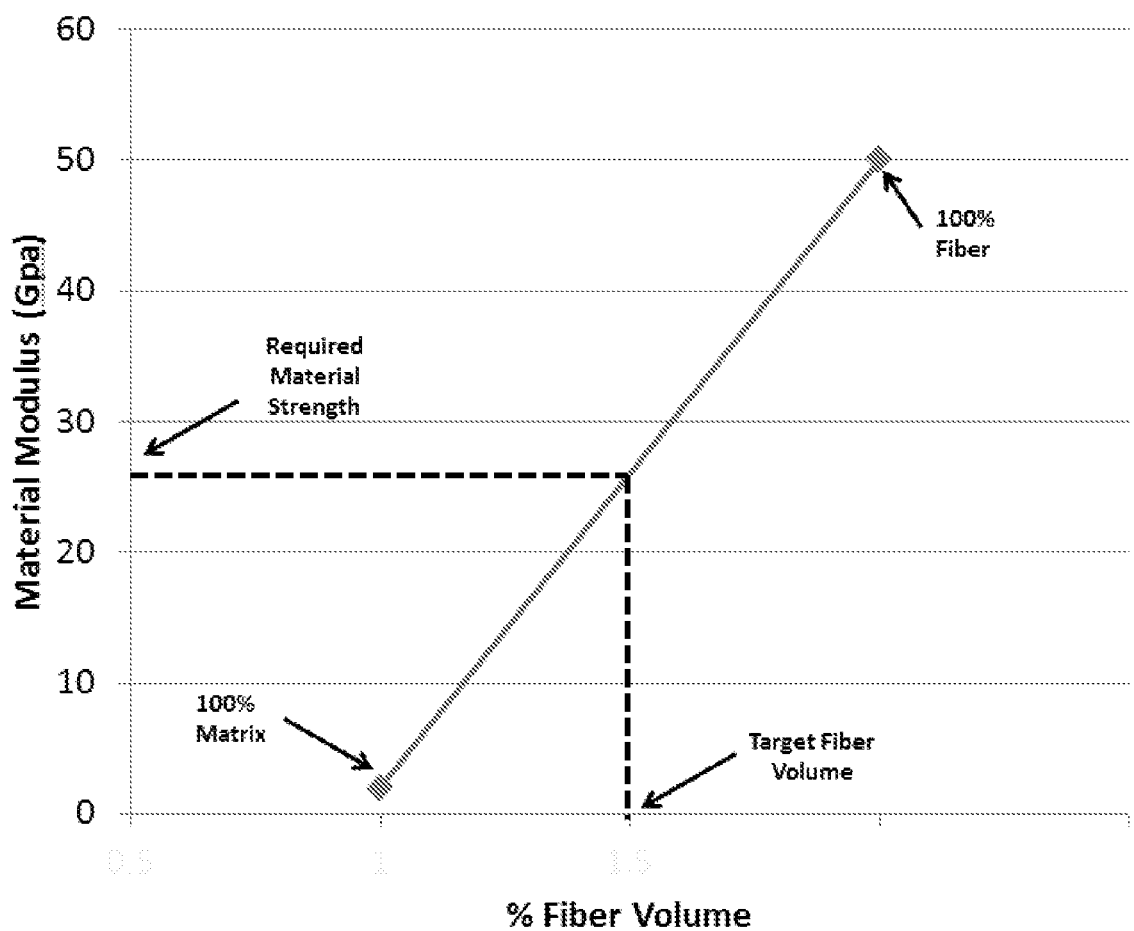
FIG. 28 is a graph showing material modulus vs. fiber volume.
Figure 29:
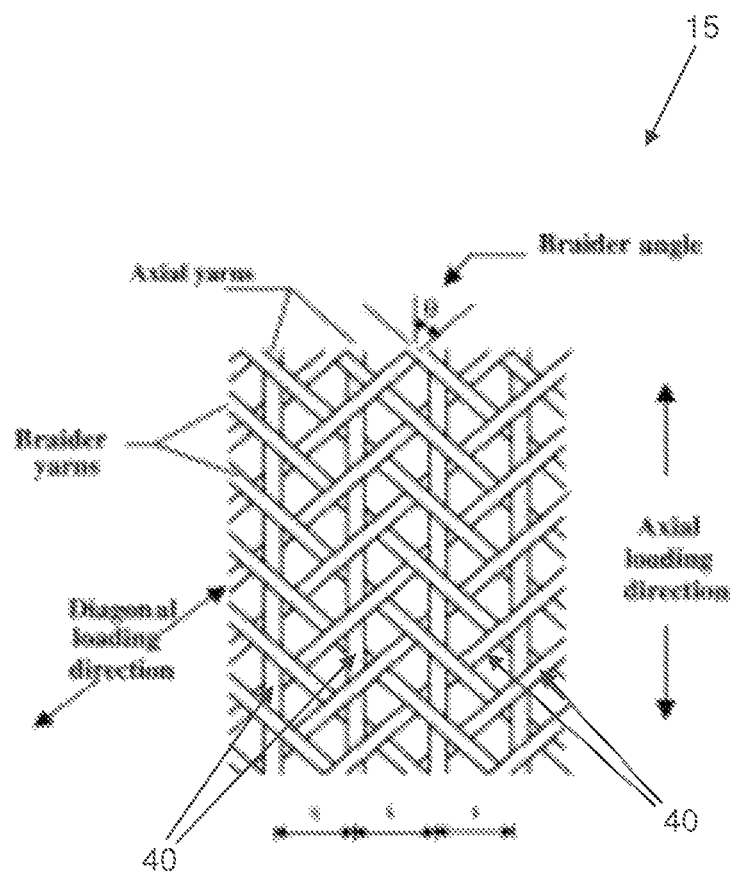
FIG. 29 shows how the reinforcing elements may be formed from fibers comprising columnar axial supports and angular cross fibers.

The final compressive and flexural modulus of the composite implant is directly related to the percent composition of fiber volume in the composite implant, i.e., a composite implant comprising a 70% fiber volume will more closely mimic the properties of the reinforcing elements than the properties of the injectable matrix material. More particularly, FIG. 28 shows a manner by which implant strength can be varied based on the ratio of constituent reinforcing elements (and the underlying "fiber" that makes up the constituent reinforcing elements). Once the required strength of the composite implant is known, a composite implant can be customized that uses an amount of distributed "fiber" reinforcing elements within the injectable matrix material. The ratio of fiber volume to matrix volume determines the ultimate strength of the composite implant, with the strength somewhere between the strength of the injectable matrix material and that of the reinforcing element(s). Additionally, the form of the fibers as they are constructed within the reinforcing elements determines where and how that strength is achieved. Fibers arranged in columnar axial supports (see FIG. 29) shift implant strength to compression and tension. Angular cross fibers (from a weave or braid) shift strength to bending and resistance to torsion. A mix of both results in a more balanced implant construct.

As an example, reinforcing elements of E-glass (45 GPa) braid was used to reinforce PLA matrix (2 GPa) in a composite implant. The mix was approximately 55% fiber volume, therefore a composite implant was created with a modulus of 20-22 GPa.

By way of further example but not limitation, in orthopedics, for a non-resorbable composite implant, a stiff composite product is chosen in the 20-80 GPa modulus range, which is appropriate in some applications using a material described hereafter in the non-resorbable reinforcement elements. If the composite implant is to be fully bio-resorbable, then the composite implant may have a 7-45 GPa modulus range as is appropriate to splint most long bone fractures. Other polymers that may or may not be biodegradable, such as biodegradable poly(2-hydroxyethyl methacrylate), can be used to create softer materials with engineered directional strengths based on the configuration of the reinforcing elements. The directions of reinforcement element fibers can create materials configured with lower moduli in the 500 MPa to 1 GPa range for craniofacial fractures and other small bone repairs as needed. In addition, it is recognized that a combination of fibers with different moduli and other properties can be used to further vary the ultimate strength of the composite implant. For instance, a glass fiber material could be combined with a polypropylene or PLLA material to produce appropriate moduli with the capability to be cut during manufacturing and resealed via heat treatment or the friction of the cutting blade. Additionally, a mix of bioresorbable fibers with non-bioresorbable fibers within a braided or woven reinforcement matrix would create an eventual pathway, after the material bioresorbs, for blood flow or other fluid transit.

Additionally, in one embodiment of the invention, the reinforcing elements may be braided into geometric formations which further increase or decrease the mechanical properties of the composite implant. By way of example but not limitation, a composite implant with "all axial" reinforcement elements will have the highest resistance to tension and compression, while a composite implant with braided reinforcement elements having "no axial" reinforcement elements, but including reinforcement elements set at approximately 45° to the axis of the composite implant, would be strong in flexural modulus but not as strong in compression. By way of further example but not limitation, woven sheets of materials used as reinforcement elements may be designed with differing weave configurations to achieve similar results.

Devices, or parts of devices, that could be created using the present invention include, but are not limited to, fabrics such as clothing and parachutes, materials used in cars (both interiors and exteriors), vascular supports (both interior and exterior). Rigid materials such as bottles, syringes, bone-supporting materials, packaging materials, catheters, and stents may also be formed using the present invention. Consumables used in other applications, such as the abrasives used in particle blasting for paint and rust removal, could also benefit from the present invention.

Preferred Method of Use

The composite implant 5 is disposed within the intramedullary canal of a bone, or within another opening in the bone, so as to function as an internal "splint", whereby to carry the stress created during patient activity. This allows a bone fracture to heal, or provides fortification and/or augmentation of bone, with minimum inconvenience to the patient. The components of the composite implant 5 are introduced sequentially into the patient, and assembled in-situ, thereby allowing the composite implant 5 to be installed using a minimally invasive approach.

In another method of use, the composite implant is pre-assembled by a manufacturer and provided to the surgeon in a sterile manner for implantation. The fracture site would be directly accessed and the composite implant placed in the intramedullary canal, with or without a containment bag. Additional injectable matrix material could be used to form-fit the composite implant to the intramedullary canal to provide significant advantage, or the composite implant can be fixed using mechanical means such as implant screw threads, press-fit in the canal, or another form of bone cement.

By way of example but not limitation, the composite implant 5 may be used in the following manner to treat a fracture in the tibia.

Figure 9:
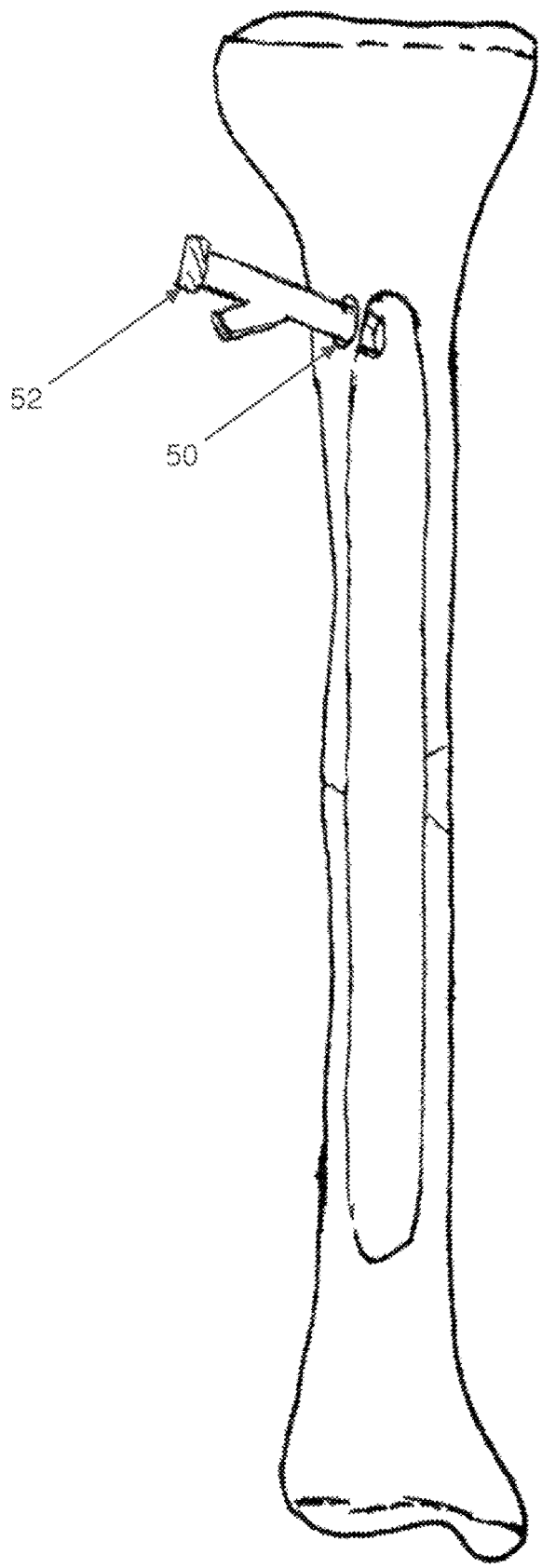
FIGS. 9-23 are schematic views showing a composite implant being assembled in situ so as to treat a bone fracture.

Looking now at FIG. 9, the first step is to create an access hole 50 into the bone that is to be treated. If desired, an access port 52 may be disposed in access hole 50 so as to facilitate delivering elements through access hole 50. When treating fractures in long bones, the hole is made into the intramedullary canal distal to, or proximal to, the fracture site. Significantly, the modular nature of the composite implant means that the composite implant can be introduced into the intramedullary canal of the bone that is to be treated through an access hole that is smaller than the final form of the composite implant. For example, in the case of where the composite implant is to fill an intramedullary canal that is 10 mm in diameter, the required access hole may be only 3 mm in diameter. As a result, the composite implant may be deployed using a minimally invasive procedure that may be carried out in an office setting or surgicenter setting rather than in a conventional operating room. Access hole 50 is preferably drilled at an acute angle to the bone which is being treated, e.g., at an angle of approximately 45 degrees, but it may be drilled at an angle anywhere between 0 degrees and 90 degrees, either proximal or distal to the fracture. This allows the components of the composite implant to be more easily introduced into the intramedullary canal.

Figure 10:
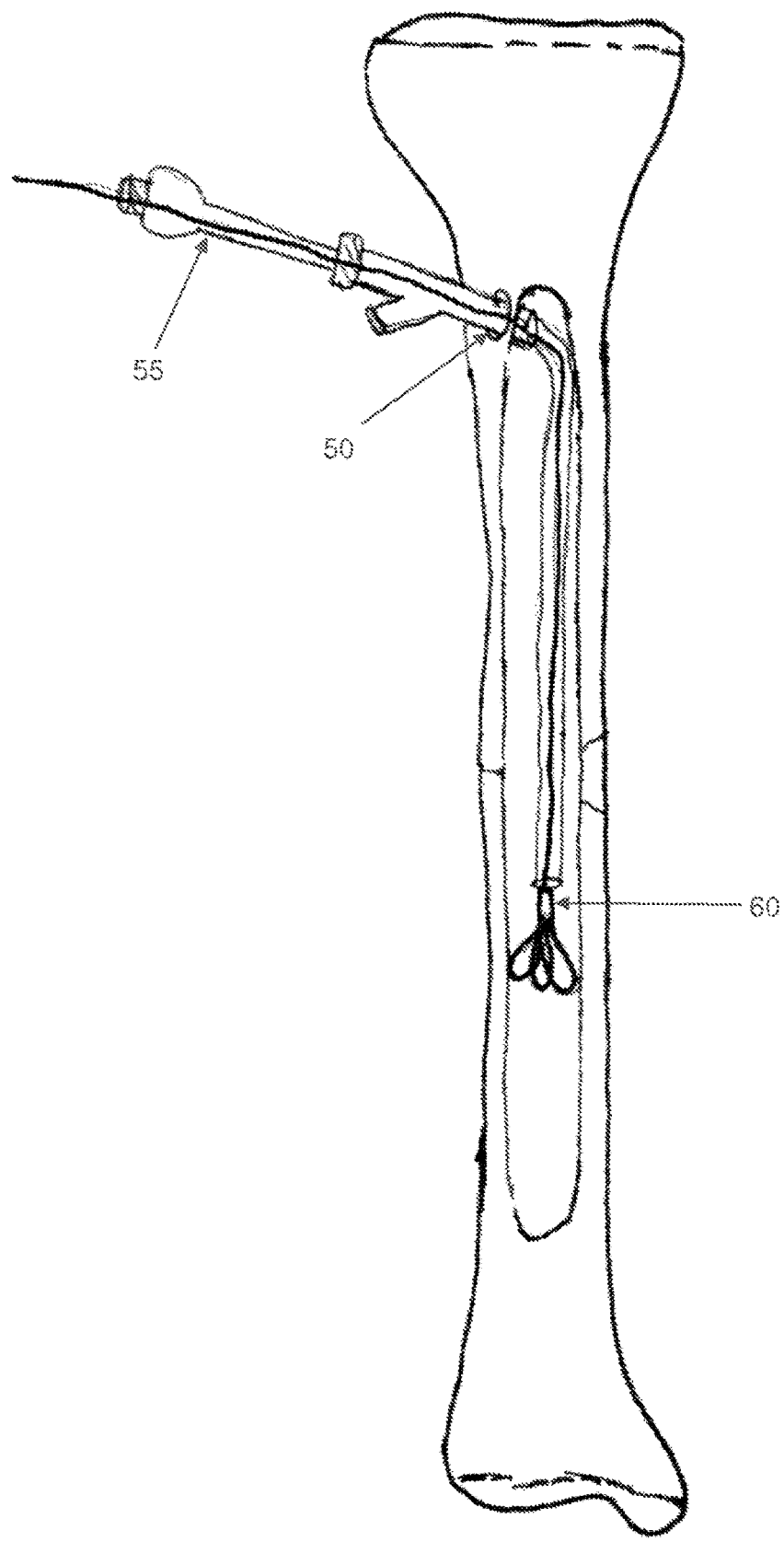
Figure 11:
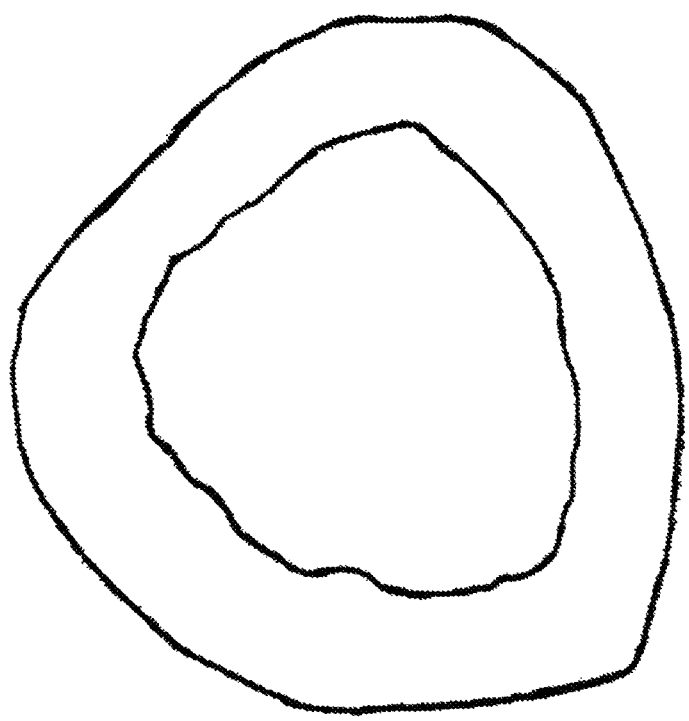

The second step is to remove or harvest the bone marrow (and/or other matter) in the intramedullary canal, and to clean the intramedullary canal, so as to provide a space for the composite implant 5. This is done through the access hole 50 previously created. In one preferred form of the invention, and looking now at FIG. 10, the device for removing or harvesting of the bone marrow from the intramedullary canal comprises a catheter 55 with provision for introducing a liquid or gas into the intramedullary canal and suction for removal of material from the intramedullary canal. The liquid or gas can be used to disrupt the content in the intramedullary canal or prepare the intramedullary canal for a composite implant. The liquid or gas can be introduced in a continuous, pulsed, or intermittent flow. A rotatable flexible rod 60, with a shaped end or attachment at the distal end (e.g., having one or more wire loops, brushes, cutting tips, etc., which may or may not be made out of a shape memory material such as Nitinol, and which may or may not be steerable), is optionally used to disrupt the bone marrow in the intramedullary canal so as to aid in the removal of the bone marrow. When harvest of the bone marrow is required, a tissue trap is utilized. FIG. 11 shows the intramedullary canal of the bone after it has been appropriately prepared.

Figure 12:
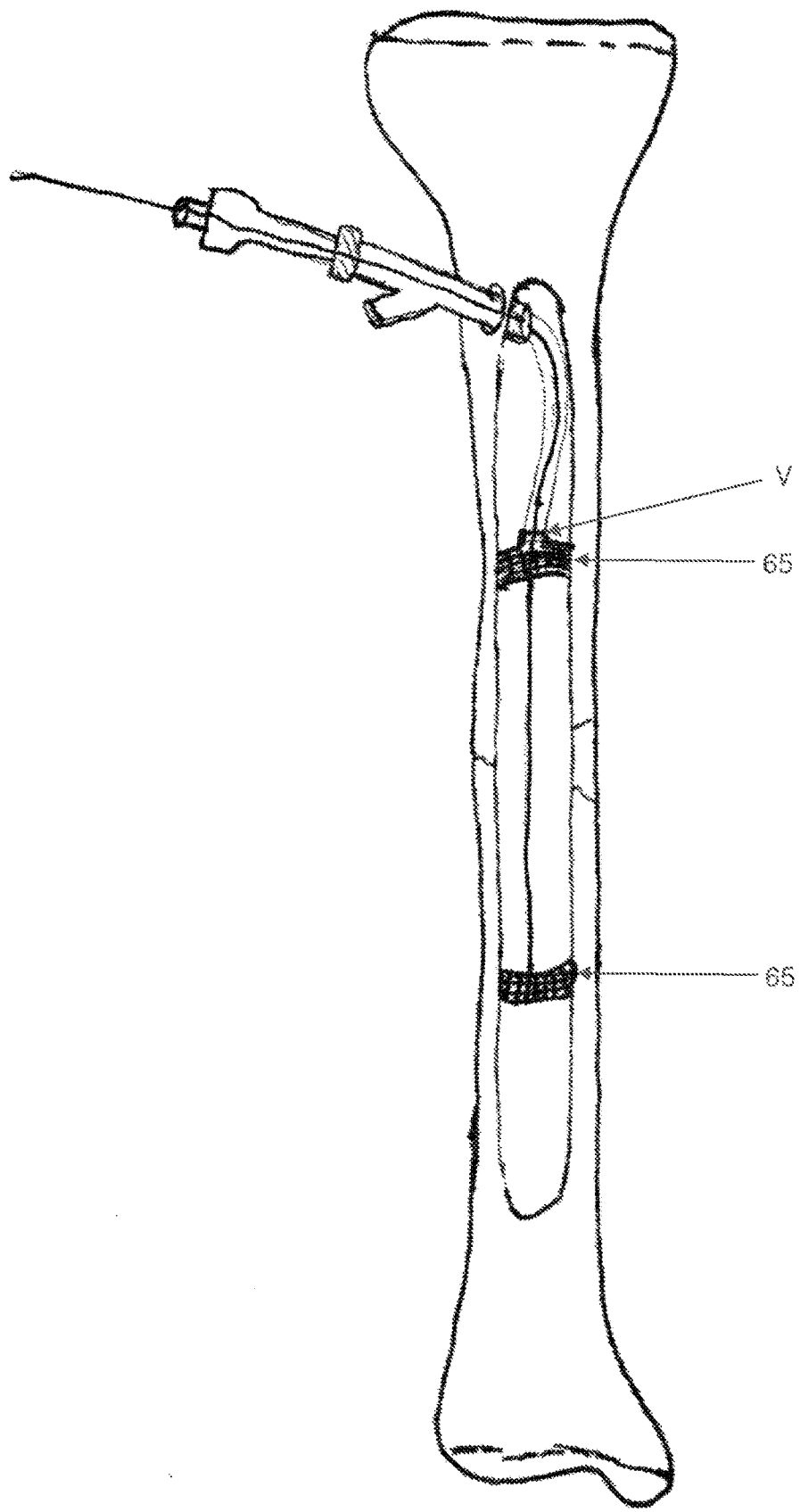
Figure 13:
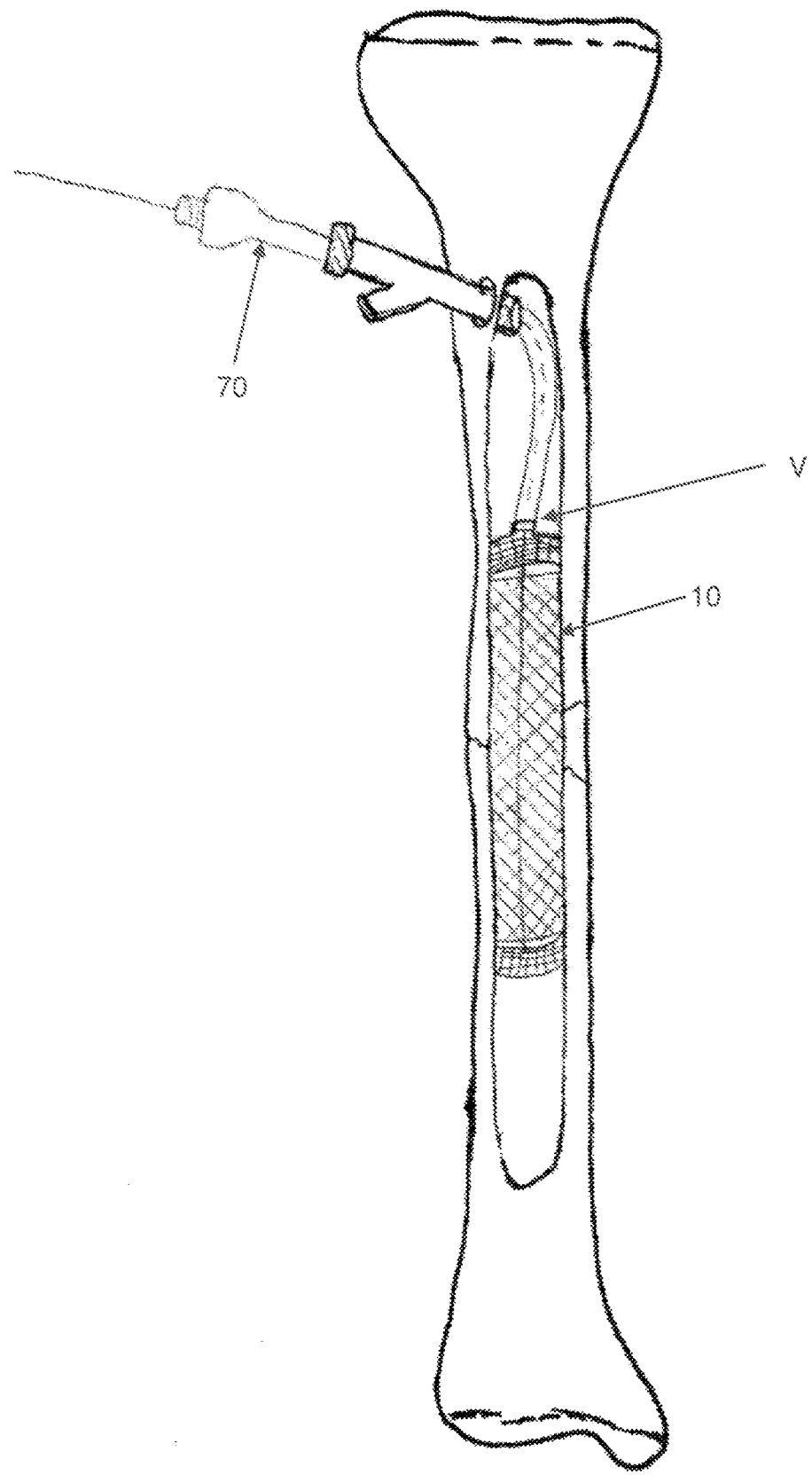

Looking next at FIG. 12, the third step, if needed, is to place a flow restrictor plug 65 in the intramedullary canal distal to, and/or proximal to, where the composite implant 5 will be placed in the intramedullary canal. Again, this is done through the access hole 50 previously created. Where two flow restrictor plugs 65 are used, the two flow restrictor plugs may be connected to one another. The flow restrictor plugs 65 may be optionally placed prior to removing or harvesting the bone marrow.

The fourth step, if needed, is to return the bone to proper alignment.

Figure 14:
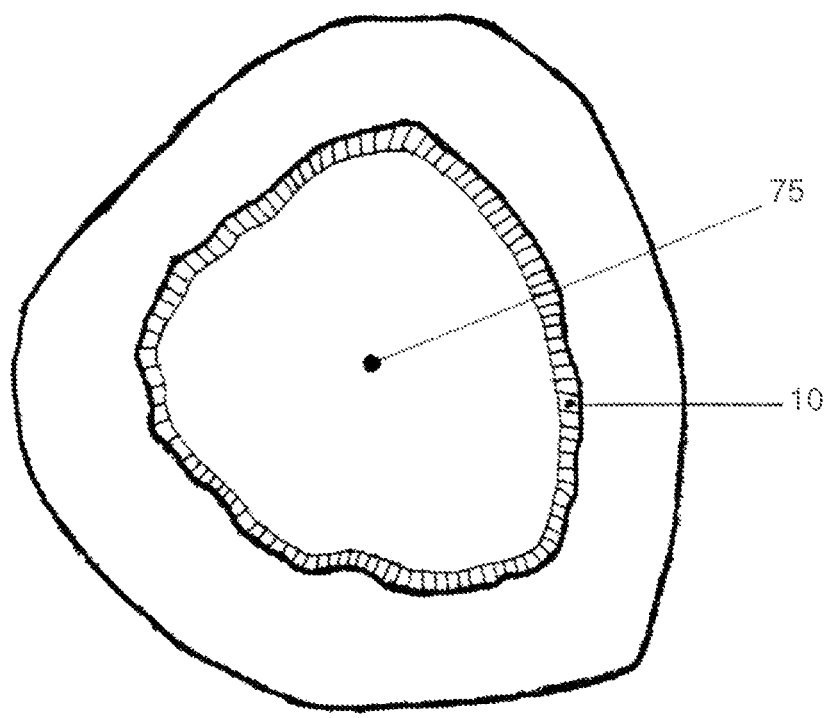

The fifth step is to introduce the containment bag 10 into the intramedullary canal via the access hole 50 previously created. In one preferred form of the invention, and looking now at FIG. 13, the containment bag 10 is introduced into the intramedullary canal through a delivery catheter 70, and is releasably attached to a catheter that is used for subsequent delivery of the remaining components of the composite implant, i.e., the one or more reinforcement elements 15 and the injectable matrix material 20. The catheter may have markers on its exterior surface so as to allow the physician to determine the position of the containment bag 10 within the bone by direct visualization of the markers on the exterior surface of the catheter. Alternatively, and/or additionally, containment bag 10 may have markers thereon so as to allow the physician to determine the position of the containment bag 10 within the bone by indirect visualization (e.g., fluoroscopy, CT, etc.). Note that the flexible (and compressible) nature of the containment bag 10 facilitates its delivery into the intramedullary canal via a minimally invasive approach (i.e., via the access hole 50 previously created). The containment bag 10 may comprise an auxiliary channel to allow monitoring and control of subsequent pressurization with the injectable matrix material. This auxiliary channel may be parallel to the delivery catheter, or inside the delivery catheter, or the auxiliary channel may be at the distal end of the containment bag. Alternatively, there may be a valve at the distal end of the containment bag, or at other strategic regions of the containment bag, that can limit pressure within the containment bag. FIG. 14 shows containment bag 10 disposed within the intramedullary canal of the bone.

Figure 15:
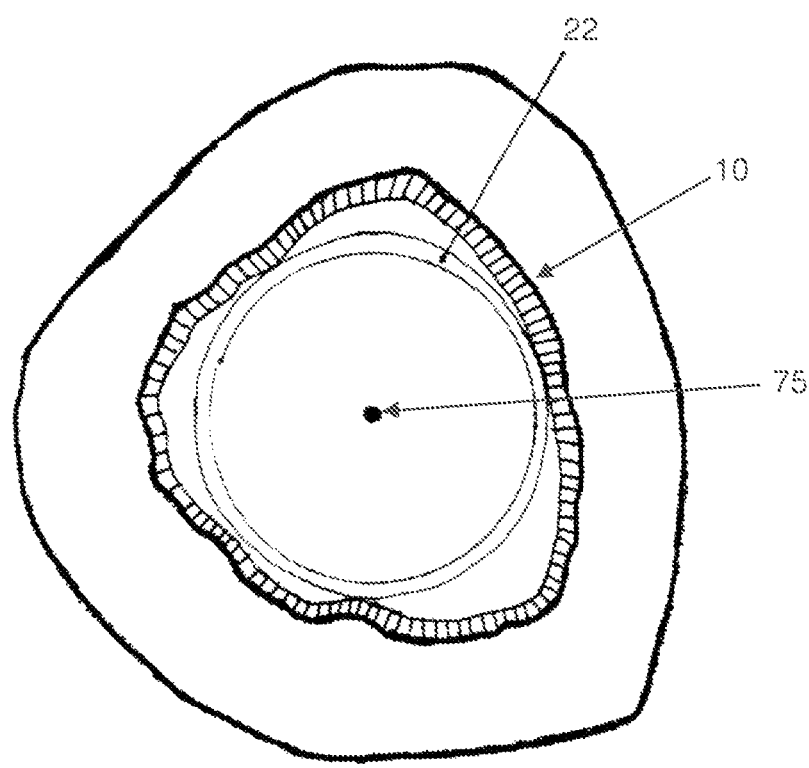
Figure 16:
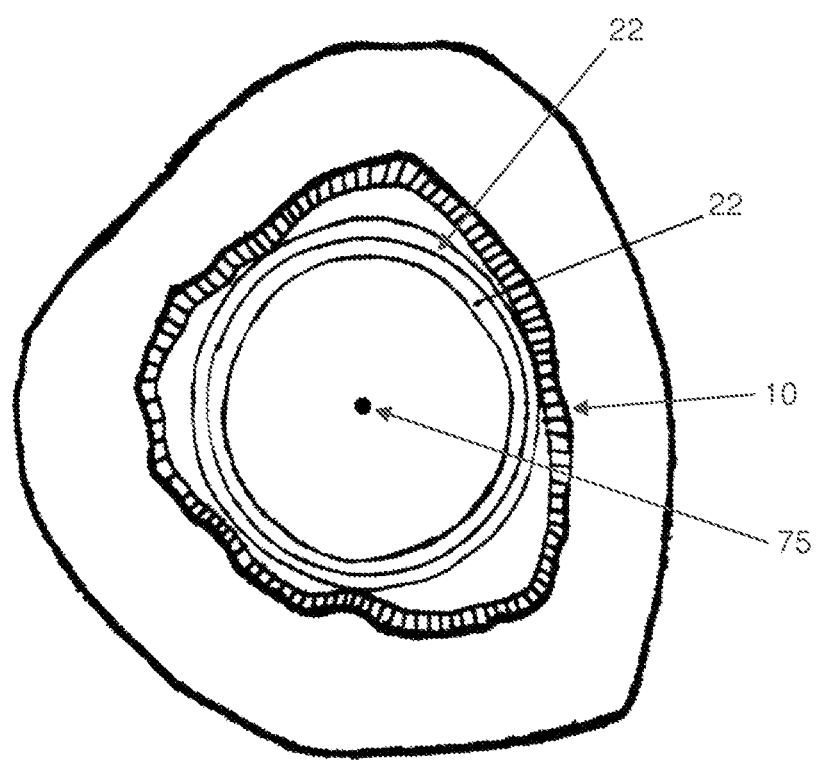
Figure 17:
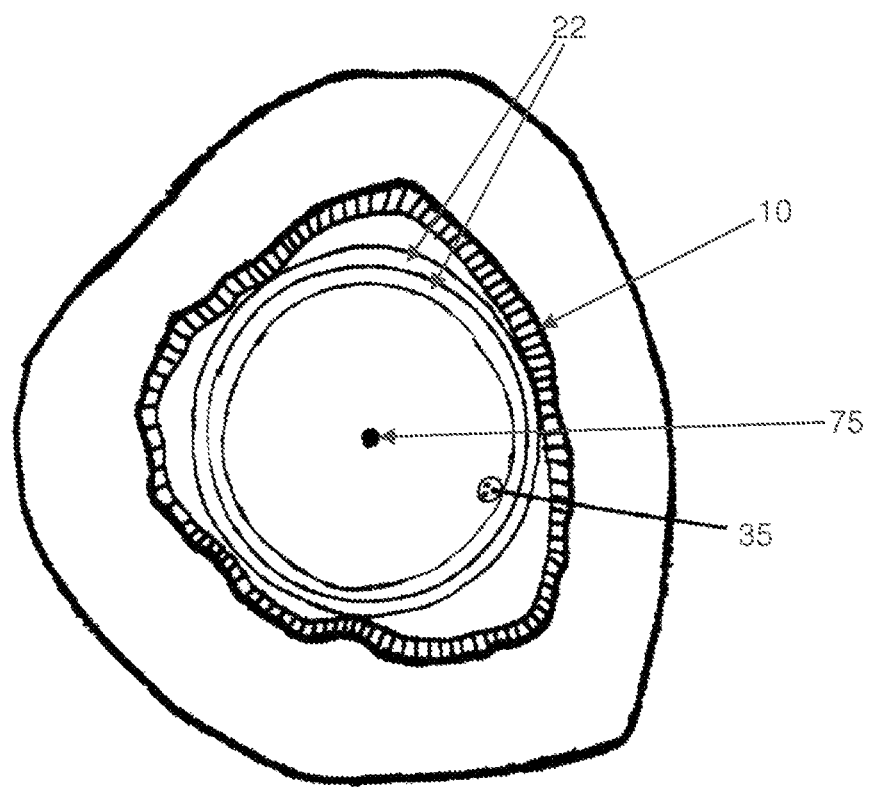
Figure 18:
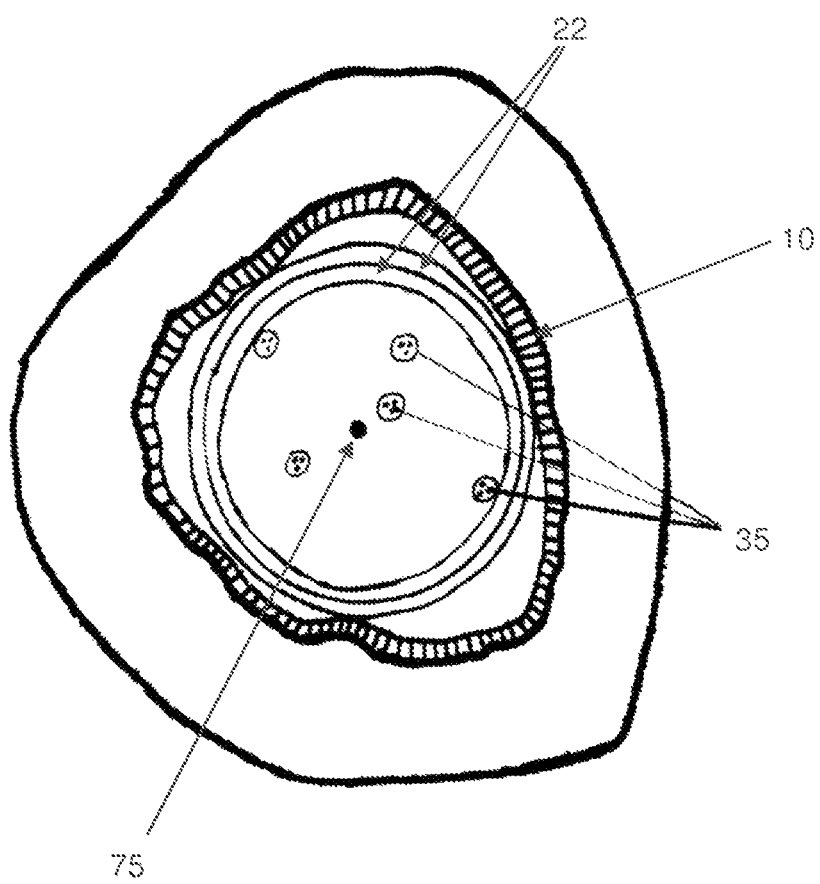
Figure 19:
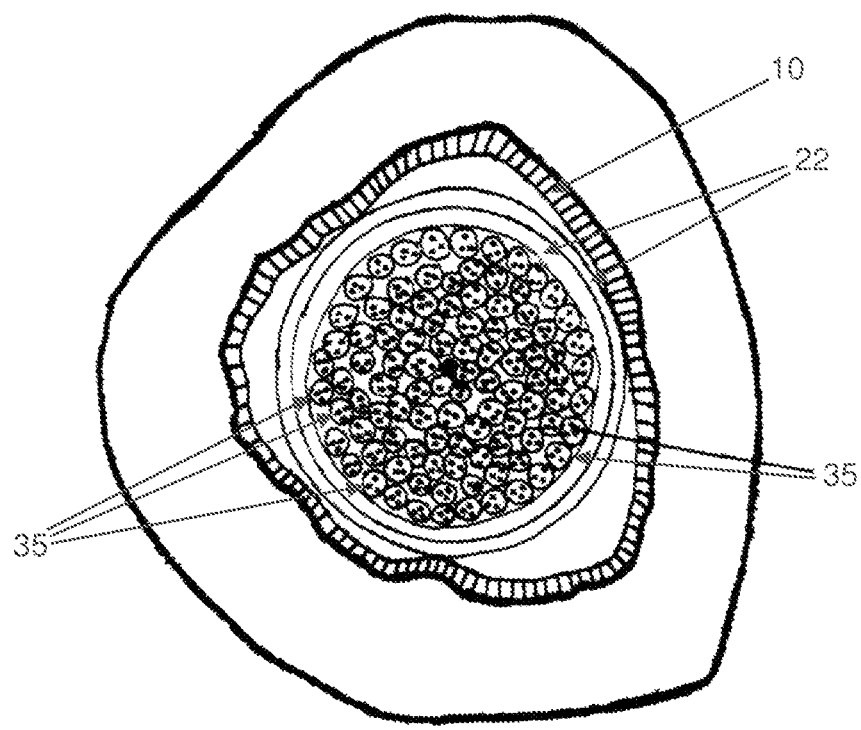
Figure 20:
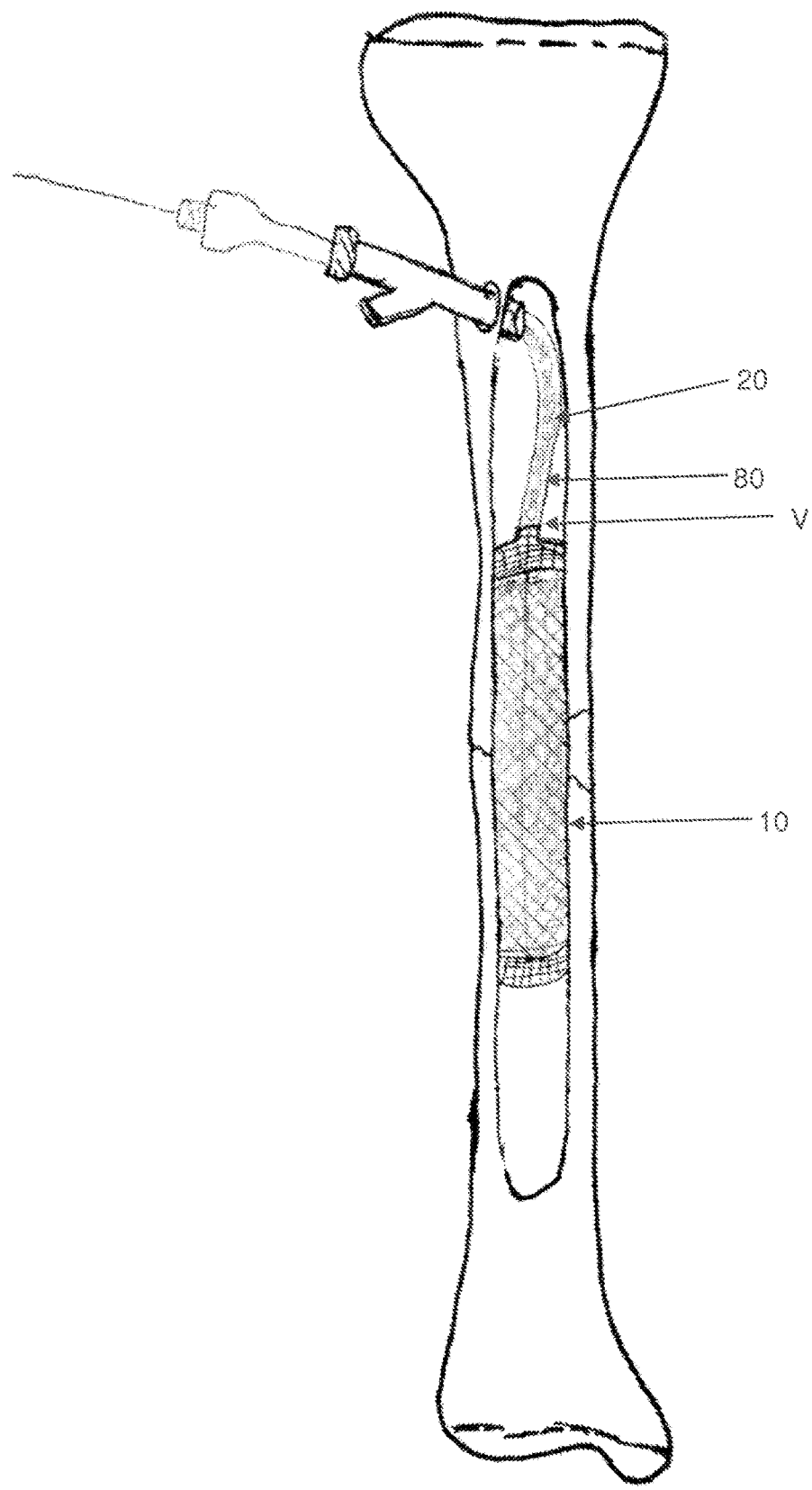

The sixth step is to sequentially introduce the one or more reinforcing elements 15 into the containment bag 10. This is done through the access hole 50 previously created. Note that the flexible nature of the reinforcing elements 15 facilitates their delivery into the containment bag 10 via the access hole 50 previously created. The one or more reinforcing structures 15 are preferably introduced into the containment bag sequentially so as to build up a reinforcing mass. In one preferred form of the invention, and looking now at FIGS. 15 and 16, a plurality of flexible reinforcing sheets 22 (in the form of concentric reinforcing tubes) are sequentially inserted into the containment bag 10, with one flexible reinforcing concentric tube 22 being nested inside another, and a plurality of flexible reinforcing rods 35 are sequentially inserted within the innermost flexible concentric reinforcing tube 22 (FIGS. 17-19). In one preferred form of the invention, the flexible reinforcing sheets 22 (which are preferably in the form of concentric tubes such as is shown in FIGS. 3 and 4 or rolled sheets such as is shown in FIGS. 5 and 6) are delivered to the interior of the containment bag by pushing them out of a delivery tube or, alternatively, by carrying them into the containment bag while held within a delivery tube and then retracting the delivery tube, whereby to expose the flexible reinforcing sheets and allow them to expand. Preferably the size and number of flexible concentric reinforcing tubes 22 and reinforcing rods 35 are selected so as to meet the individual needs of a particular patient. The number of flexible concentric reinforcing tubes 22 utilized in the composite implant, and/or their lengths and/or cross-sectional dimensions, and/or the number of reinforcing rods 35 used, and/or their lengths and/or cross-sectional dimensions, may be selected according to the individual needs of a particular patient. Preferably the number, length, and cross-sectional dimensions of the reinforcing tubes, and the number, length, and cross-sectional dimensions of the reinforcing rods, are selected so as to provide a composite implant having variable stiffness along its length, e.g., a composite implant having a stiffer central region (e.g., 20 GPa) and less stiff distal and proximal ends (e.g., 3 GPa), whereby to prevent stress risers from being created at the ends of the composite implant. To this end, the reinforcing tubes, and the reinforcing rods, are preferably provided in a variety of sizes for appropriate selection by the physician; alternatively, the reinforcing tubes and/or reinforcing rods may be sized at the time of use by the physician. If desired, a guidewire 75 may be provided to facilitate introduction of the one or more reinforcing elements into the containment bag. This guidewire 75 is preferably attached to the distal end of the containment bag 10 using an adhesive or other non-permanent attachment means. After the one or more reinforcement elements 15 have been placed in the containment bag, the guidewire 75 can be detached from the containment bag 10 by pulling or twisting the guidewire. Alternatively, the guidewire 75 may be absorbable, in which case it may be left in the patient at the conclusion of the procedure.

Figure 21:
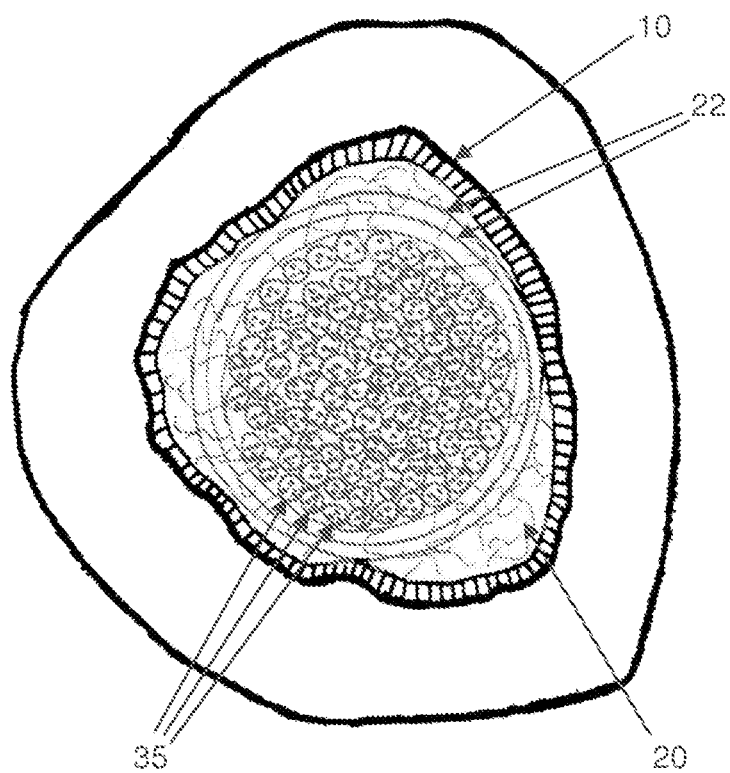

The seventh step is to introduce the injectable matrix material 20 into the containment bag. Again this is done through the access hole 50 previously created. In a preferred form of the invention the injectable matrix material is formed from two or more components that are mixed immediately prior to injection into the patient. This may occur through use of a static mixer fed by multiple syringes. Alternatively the components may be mixed in a remote container and then loaded into a syringe that is connected to the injection tube. In one preferred form of the invention, and looking now at FIGS. 20 and 21, an injection tube 80 is used to deliver the injectable matrix material 20 into the containment bag 10 under pressure, where it flows over and through the one or more reinforcement structures 15 contained within the containment bag 10. In one embodiment, the injection tube is first positioned in the distalmost section of the containment bag, then withdrawn during the injection process for a retro-grade fill. The injection tube 80 is withdrawn after the matrix material is injected into the containment bag. The injection tube is, preferably, also capable of transmitting an energy wave into the injectable matrix material in cases where pulsatile flow or the application of vibrational forces is required to aid injecting the matrix material into the containment bag. Vacuum may be used to facilitate wetting out of the reinforcement structures by removal of trapped air from the composite through a secondary access pathway within the balloon catheter.

The eighth step is for the injectable matrix material to solidify so that the matrix material 20, the one or more reinforcing elements 15 and the containment bag 10 become a single solidified structure 5 (FIGS. 22 and 23) capable of providing support across the fracture line while the bone fracture heals. If desired, an expandable device (e.g., a balloon) may be used to provide a radial force to aid in the creation of a single integrated structure. Alternately, the expandable device may be a biodegradable form or feature of the injection catheter. More particularly, the expandable device (e.g., balloon) may be used to enhance the penetration of the injectable matrix material into and between one or more reinforcing elements, the containment bag and the bone, and to enhance the interfacial bond between the injectable matrix material and the one or more reinforcing elements, between the injectable matrix material and the containment bag, and between the injectable matrix material and the bone. In the preferred embodiments of the invention this solidification occurs through a chemical reaction that proceeds at a rate that allows sufficient time for injection before the viscosity increases to a point where injection and flow into and around the reinforcements is no longer possible. Generally this time is less than five to ten minutes. Most of the solidification (15-75% of full hardness) occurs within ten to sixty minutes, although with most chemistries there will be a continuation in strength build-up over a period of up to five days. In the preferred chemistries the exothermic nature of the reaction is limited to minimize temperature increase in the matrix material to less than 10 degrees C. whereby the temperature at the bone interface is limited to <40° C.

Figure 22:
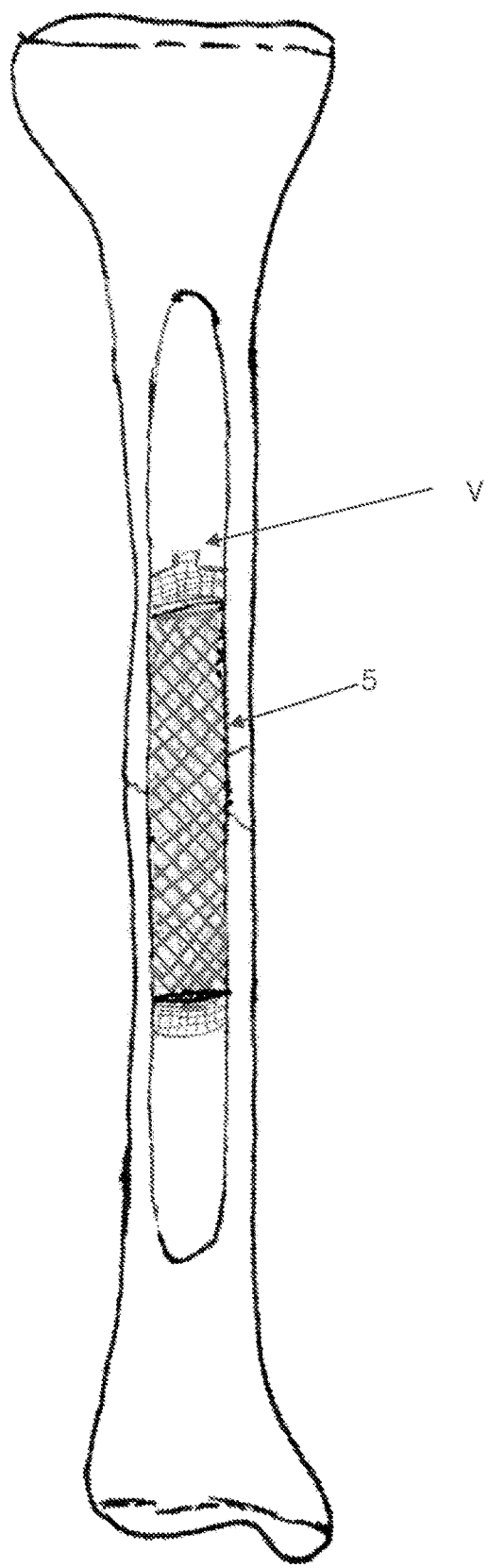
Figure 23:
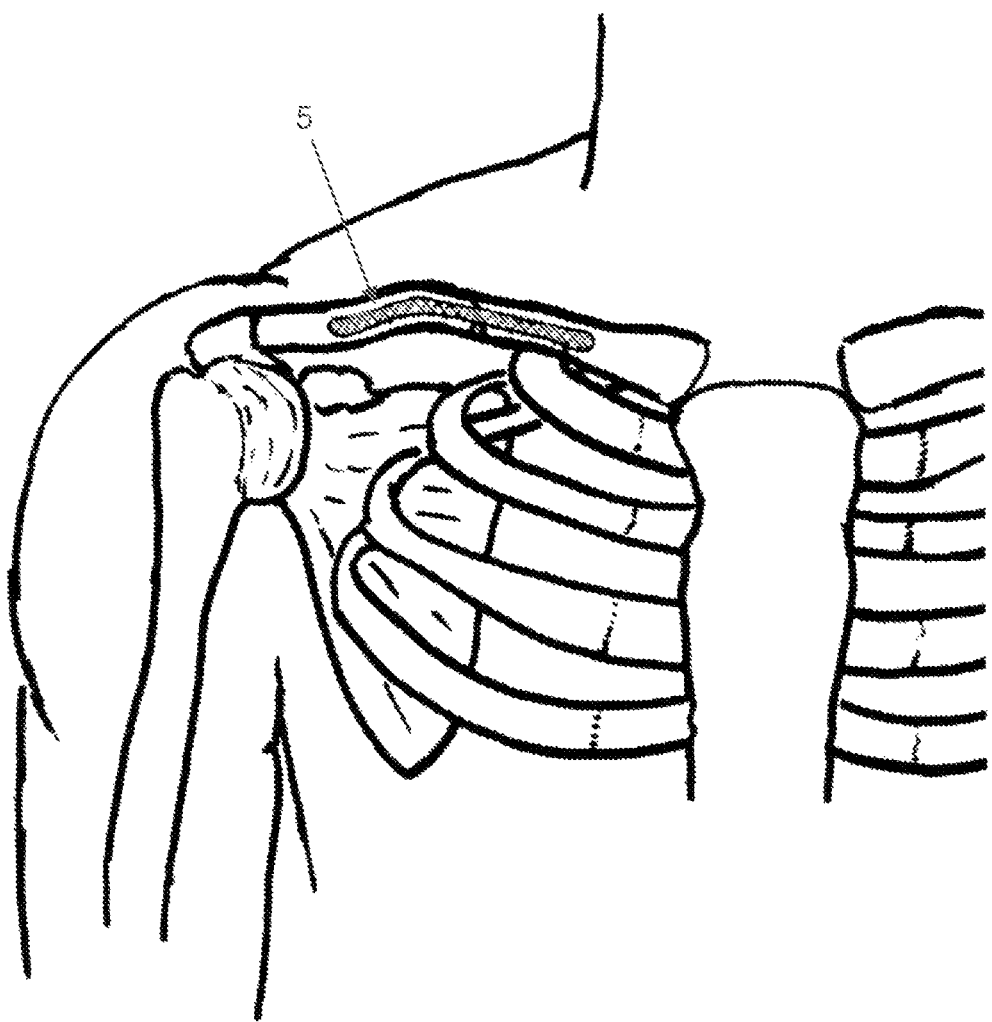

Note how, in FIGS. 22 and 23, the composite implant can contour as needed to the geometry of the intramedullary canal of the bone, i.e., in FIG. 22 the composite implant has a substantially linear shape to match the substantially linear shape of the intramedullary canal of the tibia, whereas in FIG. 23 the composite implant has a contoured shape to match the contour of the clavicle.

The ninth step is to close the wound.

Thus it will be seen that the present invention comprises the provision and use of a novel composite implant for treating bone fractures (and/or for fortifying and augmenting a bone). The composite implant is disposed within the intramedullary canal of the bone (or within another opening in the bone) so as to function as a "splint", whereby to carry the stress created during patient activity. This approach allows the bone fracture to heal (or provides fortification and/or augmentation of a bone) with minimum inconvenience to the patient. The composite implant comprises a plurality of components that are introduced sequentially into the patient, and assembled in situ, thereby allowing the composite implant to be installed using a minimally invasive approach. Significantly, the properties of the composite implant can be custom tailored for different treatment situations, e.g., the composite implant can have different lengths and/or cross-sectional dimensions, the composite implant can have different compressive and/or tensile strengths, etc., all according to the individual needs of a particular patient.

Additional Constructions

It should be appreciated that, if desired, containment bag 10 may be omitted. In this case, the one or more reinforcing elements 15 and injectable matrix material 20 are deployed directly into the intramedullary canal (or other opening) in the bone that is being treated, without an intervening containment bag 10.

Furthermore, it should be appreciated that, if desired, the reinforcement rods can be placed in a deflated balloon (i.e., the containment bag) prior to its insertion into the body, which will eliminate the need for the surgeon/physician to separately place the reinforcement rods in the containment bag in a separate step. The reinforcement rods can include individual braids or fibers, and/or pre-cured pins and rods (where matrix material is combined with the braids or fibers and then pre-cured).

Figure 24:
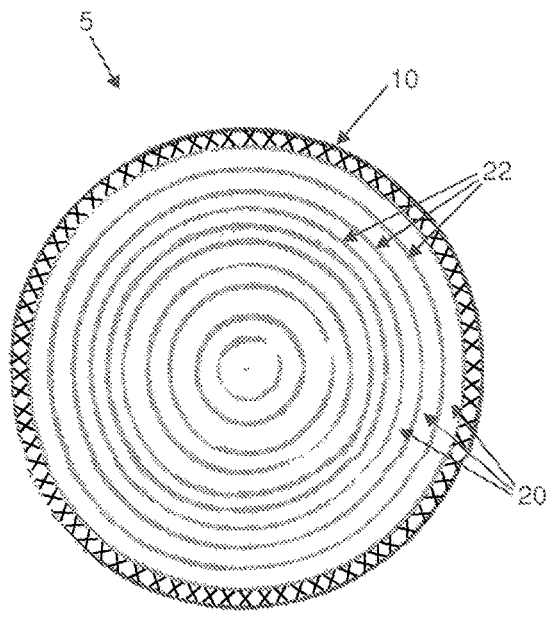
FIGS. 24-26 show alternative forms of the composite implant of the present invention.
Figure 25:
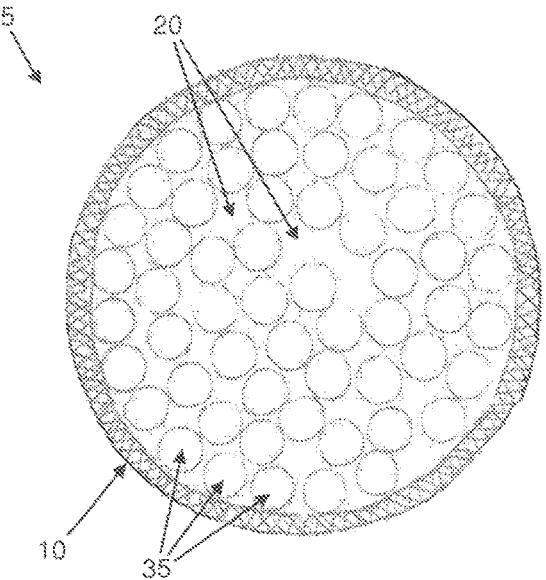
Figure 26:
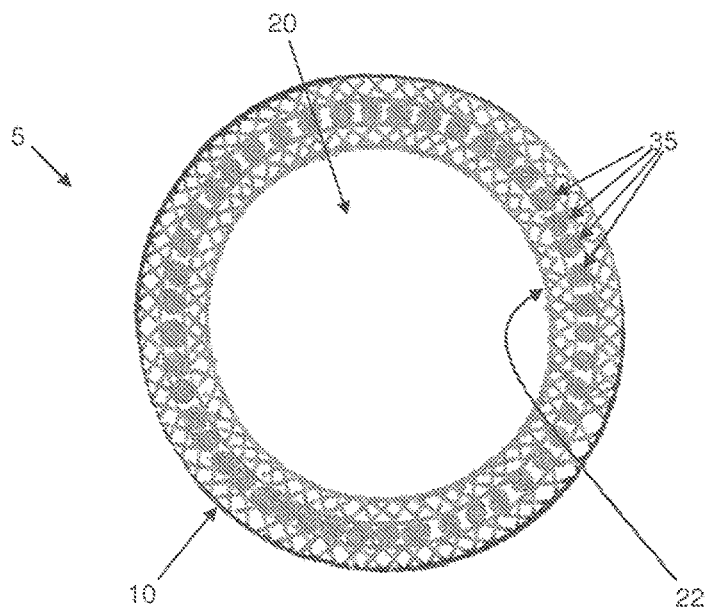

Furthermore, it should be appreciated that, if desired, composite implant 5 may be formed out of flexible reinforcing sheets 22 without any flexible reinforcing rods 35 (FIG. 24); with flexible reinforcing rods 35 and without any flexible reinforcing sheets 22 (FIG. 25); and with a laminated construction comprising both flexible reinforcing sheets 22 and flexible reinforcing rods 35 (FIG. 26).

Figure 27:
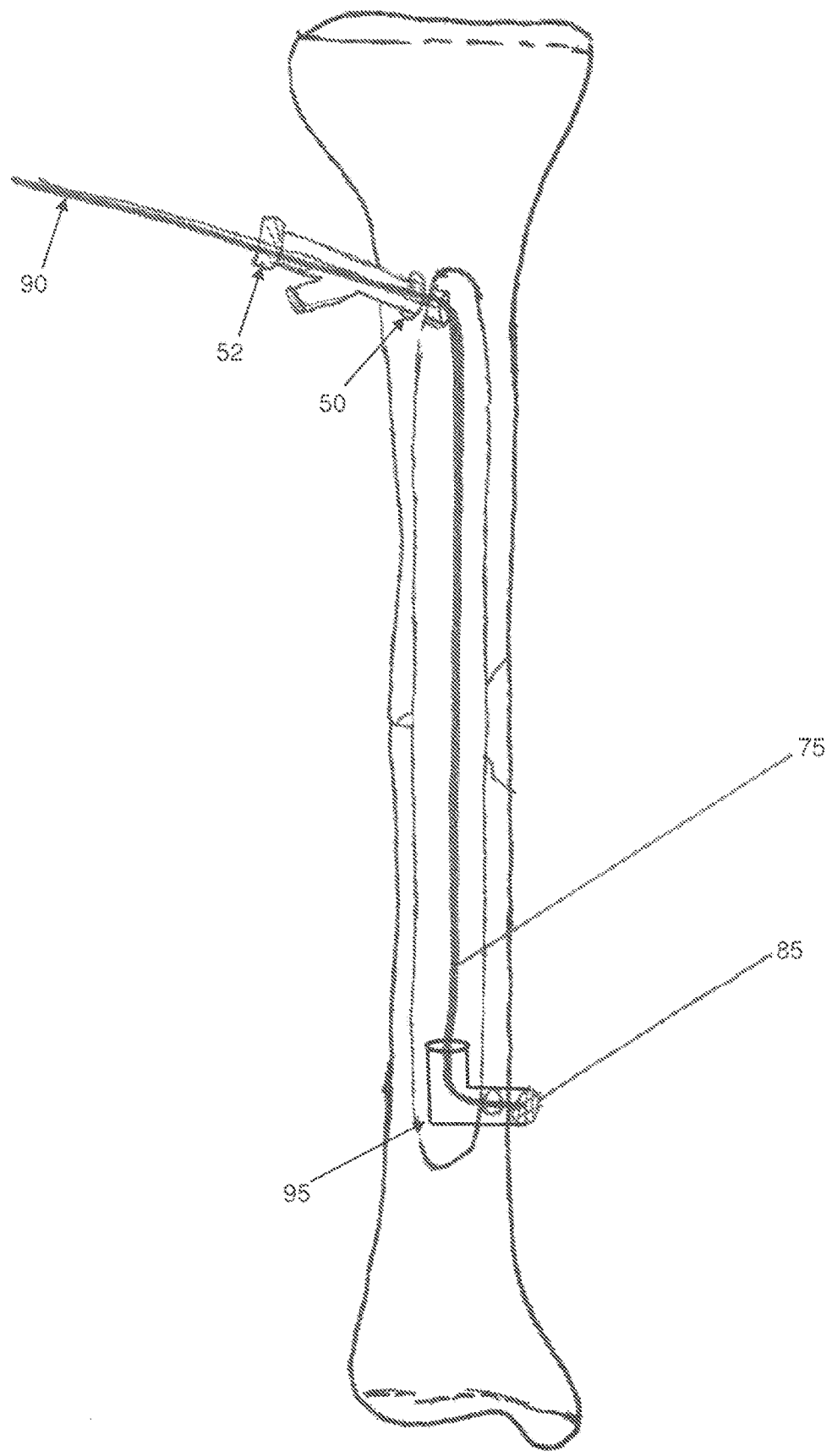
FIG. 27 shows how the guidewire used to deliver the composite implant may also be used to reduce a fracture and/or to help stabilize the fracture.

In addition, FIG. 27 shows how guidewire 75 may be used to reduce a fracture prior to delivery of the composite implant. More particularly, in this form of the invention, guidewire 75 has an enlargement 85 formed at one end, with enlargement 85 being disposed exterior to the bone being treated, and with the opposite end 90 of guidewire 75 emerging from port 52. As a result of this configuration, by applying tension to end 90 of guidewire 75, the fracture can be reduced and the tensioned guidewire 75 can help support the bone. In one preferred form of the invention, a fixture 95 may be positioned within the intramedullary canal of the bone, adjacent to enlargement 85, so as to direct guidewire 75 along the longitudinal channel of the bone and thereby facilitate fracture reduction and delivery of the composite.

It should also be appreciated that the modularity of the present invention and its method of use may be distributed throughout the manufacturing and/or treatment sequence, and are modifiable per anatomic use and surgical routine. As such, a pre-cured composite implant may be used in situations where in situ curing is not desirable, or where in situ curing would unnecessarily complicate the operative procedure, or where a minimally invasive approach is irrelevant due to recent trauma to the anatomy, including soft tissue. In this case, a bag 10 may be omitted in preference of a coating or pre-applied casing to achieve properties such as added resistivity to solvent (water), biological-implant surface compatibility, or implant surface mechanical properties.

As an example, for small bone procedures such as the treatment for a hammertoe condition, an open surgical procedure is currently the preferred technique, and a minimally invasive approach into small bones is not highly advantageous. Metal support rods are commonly used to support the revision. Polymer intramedullar support rods are typically not strong enough to survive insertion intact. A pre-cured, small diameter composite implant pin, formed with the components described herein, will have the required strength for intact insertion and maintain enough support strength through the healing process. Additionally, a preferred embodiment is bioresorbable and may include a bioresorbable surface coating as previously described.

In addition, a composite implant pin, formed in accordance with the present invention, may be implanted into the supporting halves of the bone and fixed in place using injectable matrix material as a gap-filling adhesive (bulk filler), with the specific design of the composite implant pin preferably meeting the material properties of the surrounding bone, i.e., the modulus, porosity, etc. of the surrounding bone. The use of an injectable matrix material as a gap-filling adhesive (bulk filler), with matched modulus to the bone, will eliminate stress risers and allow natural healing-inducing strains to be applied to the bone.

In a similar manner, a pre-cured composite implant formed in accordance with the present invention may be used to pin fractured segments of bone together, e.g., such as may be required with tibial fractures. More particularly, the fractured segments are re-aligned, and at least one continuous bone tunnel (e.g., the intramedullary canal) is established between fractured segments to accept insertion of the pre-cured composite implant, with or without injectable matrix material being used as bone glue. The modularity of the invention and method is maintained when used in a non-minimally invasive manner. When open surgery is required or desired, such as with traumatic injuries or patient-specific circumstances (e.g., osteoporosis, osteogenesis imperfecta), the containment bag and reinforcing elements can be assembled outside of the body and introduced into the continuous bone tunnel (e.g., the intramedullary canal) before or after injection of the injectable matrix material, then the bones are re-approximated prior to the set-up (i.e., hardening) of the injectable matrix material. This method could include the situation where a large composite implant, constituting a sub-segment (or a series of small composite implants constituting a series of sub-segments) was pre-cured and supplied by the manufacturer as with the small bone indication above and fit to the continuous bone tunnel (e.g., the intramedullary canal) with or without a containment bag, using a gap-filling injectable matrix material (preferably having bone-like material properties) to secure the composite implant in place.

Mechanical shapes and fasteners can be formed around a core composite implant so as to form screw threads on the composite implant. The mechanical shapes and fasteners formed on the core composite implant are preferably composed of injectable matrix material having material properties similar to bone. Formation of mechanical shapes and fasteners having material properties similar to bone will reduce post-implantation thread wear and allow for natural healing due to similar strains between the native bone and composite implant. Other forms of mechanical shapes and fasteners can include bent pins, clips with semi-elastic properties, bone anchors (e.g., toggling bone anchors which catch on internal bone structure, etc.), and/or other mechanical fasteners required for anatomical (e.g., soft tissue) repairs.

It will be recognized that various methods of manufacturing may provide further benefits to the composite implant. A pultrusion technique wherein a resin is applied over a rolled reinforcement element sheet or a braided or woven core of reinforcement element would give the ability to create long pins that may or may not be bioresorbable with a much higher modulus than that of current molded pure or blended polymer fixation elements.

In a preferred embodiment of the present invention, the geometry of the reinforcing elements are non-circular space-filling designs. A specific and preferred shape is a reinforcing element in the form of a rod having a triangular cross-section. Multiple reinforcement elements having this shape may be combined to form a single, larger pre-formed rod in order to increase the fiber density inside a composite implant built up from many stacked rods having a triangular cross-section. Rods having a triangular cross-section are advantageous in that any impact force applied on a single rod component will be spread across a plane of contact, instead of the impact force being concentrated on a point contact such as the case with a rod having a circular cross-section. Furthermore, the modularity of a "triangular rod" allows for stacked configurations of squares, trapezoids and other useful configurations to be produced, all with very high fiber contents. Pre-formed composite implants can be created in a flat-rod configuration, using multiple aligned (and appropriately configured) triangular components.

Composite Implant Utilizing A Thermoplastic Polymer Injectable Matrix Material

In one form of the invention, the composite implant comprises a thermoplastic polymer implant comprising a thermoplastic polymer matrix and a high modulus fiber component having a tensile modulus from about 8 GPa to about 400 GPa.

The fiber content of the thermoplastic polymer implant may be from about 5 volume percent to about 75 volume percent.

Or the fiber content of the thermoplastic polymer implant may be from about 25 volume percent to about 50 volume percent.

The fiber component may be selected from the group consisting of E glass, bio glass, soluble glass, resorbable glass, carbon fiber, polyaramid fiber, PET fiber, polylactic acid homopolymer or copolymer fiber, polycaprolactone fiber, ceramic fiber, polyhydroxyalkanoate homopolymer or copolymer fiber, PEEK fiber or combinations thereof.

And the fiber component may comprise at least one from the group consisting of a plurality of single filaments, woven filaments, braided filaments and composite mesh containing at least one compositional fibers.

In one form of the invention, the fiber component comprises a high modulus fiber having a modulus greater than 10 GPa compressive strength and a low modulus thermoplastic fiber having a modulus less than 8 GPa compressive strength, and the low modulus thermoplastic fiber is pre-melted so as to provide a position-retaining structure for the high modulus fibers.

The fiber component may have a length-to-width aspect ratio of at least 20:1.

In one form of the invention, the high modulus fiber component comprises a matrix, and the thermoplastic polymer matrix is combined with the fiber matrix via a solution-casting process.

The thermoplastic polymer matrix may be applied from a solvent solution to a fiber construct through multiple application steps, wherein the solvent is removed after each step so as to allow for full wetting of the fiber surfaces and removal of any voids from trapped solvent components.

The high modulus fiber component may comprise a matrix, and the thermoplastic polymer matrix may be combined with the fiber matrix via a melt coating process.

The melt coating process may be a pultrusion of a T bar fiber extrusion process.

The thermoplastic polymer matrix is selected from the following biodegradable or bioabsorbable materials: polylactic acid homopolymer or copolymer, polycaprolactone, ceramic, polyglycolide (PGA), glycolide copolymers, glycolide/lactide copolymers (PGA/PLA), and polylactic acid cocaprolactone block copolymer or random copolymer, polyglycolic acid copolylactic acid block or random copolymer, glycolide/trimethylene carbonate copolymers (PGA/TMC), stereoisomers and copolymers of polylactide, poly-L-lactide (PLLA), poly-D-lactide (PDLA), poly-DL-lactide (PDLLA), L-lactide, DL-lactide copolymers, L-lactide, D-lactide copolymers, lactide tetramethylene glycolide copolymers, lactide/trimethylene carbonate copolymers, lactide/delta-valerolactone copolymers, lactide/epsilon-caprolactone copolymers, polydepsipeptide (glycine-DL-lactide copolymer), polylactide/ethylene oxide copolymers, asymmetrically 3,6-substituted poly-1,4-dioxane-2,4-diones, polyhydroxyalkanoate (PHA) homopolymer or copolymer, poly(3-hydroxybutyrate-co-3-hydroxyvalerate) (PHBV), poly-β hydroxybutyrate (PHB), 3-polyhydroxybutyrate-co-4-polyhydroxybutyrate copolymer, 3-polyhydroxybutyrate-co-5-polyhydroxy valerate, 3-polyhydroxybutyrate-co-6-polyhydroxyhexanoate, poly-3-hydroxybutyrate-co-4-hydroxybutyrate, poly-4-hydroxybutyrate (P4HB), PHB/beta-hydroxyvalerate copolymers (PHB/PHV), poly-beta.-hydroxypropionate (PHP), poly-beta-dioxanone (PDS), poly(butylene succinate) (PBS), polybutylene succinate adipate (PBSA), polyhydroxyhexanoate (PHH), polyhydroxyoctanoate (PHO), poly-DELTA-valerolactone, poly-DELTA-caprolactone, methyl methacrylate-N-vinyl pyrrolidone copolymers, polyester amides, oxalic acid polyesters, polydihydropyrans, polypeptides from alpha-amino acids, poly-beta-maleic acid (PMLA), poly-beta-alkanoic acids, polyethylene oxide (PEO), silk, collagen, derivatized hyaluronic acid resorbable or soluble glasses, resorbable ceramic, resorbable metal and chitin polymers.

The thermoplastic polymer implant be constructed so that it starts to degrade in the body within about 1 month to about 24 months after implantation in the body.

Or the thermoplastic polymer implant may be constructed so that it loses at least 50% of its original mechanical strength after 3 months in the body.

Or the thermoplastic polymer implant may be constructed so that it loses at least 50% of its original mechanical strength after 6 months in the body.

Or the thermoplastic polymer implant may be constructed so that it loses at least 80% of its original mechanical strength after 12 months in the body.

The thermoplastic polymer implant may be constructed so that about 1% to about 25% of the thermoplastic polymer matrix is replaced by a crosslinking polymer component so as to provide improved adhesive strength between the thermoplastic polymer matrix and the high modulus fiber component.

In one form of the invention, the high modulus fiber component comprises a matrix, and the thermoplastic polymer matrix is applied to the fiber matrix in the form of a fine powder and then heat fused to consolidate the subsequent molten thermoplastic polymer matrix around the high modulus fiber component.

And in one form of the invention the high modulus fiber component comprises a matrix, and the thermoplastic polymer matrix is applied to the fiber matrix via electrospinning of the thermoplastic polymer and then heat fused to consolidate the subsequent molten thermoplastic polymer matrix around the high modulus fiber component.

And in one form of the invention, the high modulus fiber component comprises a matrix, and the thermoplastic polymer matrix is applied to the fiber matrix via electrospinning of the thermoplastic polymer matrix and the resultant voids filled with a composition which polymerizes into a high molecular weight polymer.

The thermoplastic polymer matrix may comprise vinyl monomers which are cured using free radical initiators, UV radiation, gamma ray irradiation, or infrared radiation.

The thermoplastic polymer matrix may be cured through a condensation or addition reaction or specialized reactions related to these and known to those skilled in the art.

The thermoplastic polymer matrix may be cured through a urethane or epoxide resin process.

The high modulus fiber component may be coated with the thermoplastic polymer matrix and they are then bonded together with a crosslinking resin so as to produce the final thermoplastic polymer implant geometry.

The crosslinking resin may comprise a urethane or urea composition.

The high modulus fiber component may comprise a braided rod having a triangular cross-section.

The high modulus fiber component may comprise a braided rod having a circular cross-section.

In one form of the invention, the thermoplastic polymer implant is formed prior to implantation.

The thermoplastic polymer implant may comprise a rod having a substantially circular cross-section.

The thermoplastic polymer implant may comprise a rod having a substantially triangular cross-section.

The rod may be cannulated.

In one form of the invention, the cannulation is created by forming the thermoplastic polymer implant over a mandrel and then removing the mandrel after the thermoplastic polymer implant is cured.

In one form of the invention, the thermoplastic polymer implant comprises at least two high modulus fiber components each comprising a braided rod having a triangular cross-section, and the at least two high modulus fiber components combine to form larger structures.

The thermoplastic polymer implant may be formed into a shape selected from the group consisting of a screw, a rod, a pin, a nail and a bone anchor.

In one form of the invention, there is provided a method for treating a bone, the method comprising: selecting at least one reinforcing element to be combined with an injectable matrix material so as to together form a composite implant capable of supporting the bone, wherein the at least one reinforcing element comprises a high modulus fiber component having a tensile modulus of about 8 GPa to about 400 GPa; positioning the at least one reinforcing element in a cavity in the bone; flowing the injectable matrix material into the cavity in the bone so that the injectable matrix material interfaces with the at least one reinforcing element; and transforming the injectable matrix material from a flowable state to a non-flowable state so as to establish a static structure for the composite implant, such that the composite implant supports the adjacent bone.

The cavity in the bone may comprise the intramedullary canal.

The intramedullary canal may be accessed through a hole having a diameter smaller than the diameter of the intramedullary canal.

The hole may extend at an acute angle to the intramedullary canal.

The at least one reinforcing element may be flexible, and the at least one reinforcing element may be flexed in order to pass through the hole and into the intramedullary canal.

The at least one reinforcing element may be flexible both radially and longitudinally.

The at least one reinforcing element may comprise a plurality of reinforcing elements, wherein each of the reinforcing elements is individually capable of being passed through the hole, and further wherein the plurality of reinforcing elements collectively form a structure too large to be passed through the hole.

The at least one reinforcing element may comprise at least one from the group consisting of a flexible reinforcing sheet, a flexible reinforcing rod, and particulates.

The at least one reinforcing element may comprise a flexible reinforcing sheet in the form of a tube.

The at least one reinforcing element may comprise at least two flexible reinforcing sheets arranged concentrically.

The at least one reinforcing element may comprise a flexible reinforcing sheet in the form of a rolled sheet.

The at least one reinforcing element may comprise a flexible reinforcing sheet having an arcuate cross-section.

The at least one reinforcing element may comprise a flexible reinforcing sheet having a planar cross-section.

The at least one reinforcing element may comprise a flexible reinforcing sheet comprising filaments formed into a textile.

The at least one reinforcing element may comprise a flexible reinforcing sheet comprising filaments connected by a film.

The at least one reinforcing element may comprise a flexible reinforcing rod comprising filaments held together.

The at least one reinforcing element may comprise a flexible reinforcing rod and the filaments are held together by an outer sheath.

The outer sheath may comprise filaments formed into a textile.

The at least one reinforcing element may comprise a flexible reinforcing rod and the filaments are held together by a compacted connecting structure of a textile or film.

The connecting structure may be compacted by at least one of winding and compressing.

The at least one reinforcing element may comprise a flexible reinforcing rod and the filaments may be held together by a binder.

The at least one reinforcing element may comprise particulates.

The at least one reinforcing element may comprise at least one flexible reinforcing sheet and at least one flexible reinforcing rod.

The at least one flexible reinforcing sheet and the at least one flexible reinforcing rod may be selected so as to form the composite implant with a desired stiffness.

The composite implant may have a stiffer central region and less stiff distal and proximal ends.

The injectable matrix material may comprise a polymer.

The composite implant may further comprise a containment bag, and the at least one reinforcing element may be positioned within the containment bag after the containment bag has been positioned within the cavity in the bone.

In another form of the invention, there is provided a method for treating a bone, the method comprising: selecting at least one high modulus fiber component having a tensile modulus from about 8 GPa to about 400 GPa, wherein the at least one high modulus fiber component comprises a rod having a cross-section selected from the group consisting of round and circular; flowing an injectable matrix material into the cavity in the bone so that the injectable matrix material interfaces with the at least one high modulus fiber component so as to form a composite implant, wherein the injectable matrix material comprises a thermoplastic polymer matrix; and transforming the injectable matrix material from a flowable state to a non-flowable state so as to establish a static structure for the composite implant, such that the composite implant supports the adjacent bone.

The composite implant may comprise a containment bag, and the at least one high modulus fiber component may be positioned within the containment bag after the containment bag has been positioned within the cavity in the bone.

In another form of the invention, there is provided a method for treating a bone, the method comprising: selecting at least one high modulus fiber component having a tensile modulus from about 8 GPa to about 400 GPa, wherein the high modulus fiber component comprises a plurality of fibers, and further wherein the high modulus fiber component is pre-loaded with an injectable matrix material just prior to implantation so as to together form a composite implant, wherein the injectable matrix material comprises a thermoplastic polymer matrix; positioning the composite implant in a cavity in the bone; flowing additional injectable matrix material into the high modulus fiber component so that the injectable matrix material exudes from the surfaces of the high modulus fiber component and interfaces with the surrounding bone cavity; and transforming the injectable matrix material from a flowable state to a non-flowable state so as to establish a static structure for the composite implant, such that the composite implant supports the adjacent bone and or approximated soft tissue.

Composite Implant Utilizing a Urethane Polymer Injectable Matrix Material

In one form of the invention, the composite implant comprises a polymer implant comprising a high modulus fiber reinforcing component and a urethane polymer matrix.

The high modulus fiber reinforcing component may be present in an amount from about 10 volume percent to about 75 volume percent of the polymer implant and wherein the modulus of the high modulus fiber reinforcing component is from about 6 GPa to about 90 GPa.

The high modulus fiber reinforcing component may be selected from the group consisting of E glass, carbon fiber, bio glass, soluble glass, resorbable glass, ceramic fiber, and polylactic acid homopolymer and copolymer fibers The high modulus fiber reinforcing component may be disposed in the polymer implant in a uniaxial direction along the major axis of the polymer implant.

The high modulus fiber reinforcing component may comprise a woven or braided construct.

The orientation of the woven or braided construct of the high modulus fiber reinforcing component may be held in position by a lower modulus fiber construct, wherein the lower modulus fiber construct comprises up to 10% by weight of the total high modulus fiber reinforcing component and with the lower modulus fiber construct having a melting point between about 40 degrees C. and about 200 degrees C., such that the high modulus fiber reinforcing component is made more rigid for application into the polymer implant before curing of the urethane polymer matrix.

The high modulus fiber reinforcing component may have a length-to-width aspect ratio of at least 20:1.

The urethane injectable matrix material may be formed as described above in the section entitled "Injectable Matrix Material".

The urethane polymer matrix may comprise at least two individual components that are mixed together to initiate the curing reaction, wherein a first component contains isocyanate functionalities and a second component contains active hydrogen functionalities capable of reacting with the isocyanate functionalities so as to form at least one from the group consisting of urethane, urea, biuret and allophonate groups during the crosslinking reaction.

The first component may be selected from the group consisting of a diisocyanate molecule, a triisocyanate molecule, a polyisocyanate molecule having at least two isocyanate groups per molecule, an isocyanate capped polyol having at least two free isocyanate groups per molecule, an isocyanate capped polyether polyol having at least two free isocyanate groups per molecule and an isocyanate capped polyester polyol having at least two free isocyanate groups per molecule.

Or the first component may be selected from the group consisting of isophorone diisocyanate, hexamethylene diisocyanate, lysine diisocyanate, methyl lysine diisocyanate, lysine triisocyanate, toluene diisocyanate 1,2 and 1,4 and blends, methylene diphenyl diisocyanate (MDI) and polymeric MDI having an isocyanate functionality from about 2.2 to about 2.8 isocyanate groups per molecule.

Or the first component may be a polyol isocyanate having a weight average molecular weight from about 200 to about 10,000.

Or the first component may be a blend of diisocyanate or triisocyanate molecules with a polyol capped isocyanate having two, three or four isocyanate groups per molecule in a ratio of about 1:99 percent by weight to about 99:1 percent by weight of the total isocyanate component and has a viscosity at 25 degrees C. from about 250 cps to about 5,000 cps.

The second component may be selected from the group consisting of a polyol having at least two hydroxyl groups and up to four hydroxyl groups per molecule where the hydroxyl groups are primary or secondary hydroxyls, a polyether polyol having at least two hydroxyl groups and up to four hydroxyl groups per molecule, a polyester polyol having at least two hydroxyl groups and up to four hydroxyl groups per molecule where the polyester is formed by the reaction of a diol or triol with a diacid, a polyester polyol having at least two hydroxyl groups and up to four hydroxyl groups per molecule where the polyester is formed by the reaction of hydroxyacid which is then endcapped with a diol or triol, an aspartate molecule, an amine molecule having from at least two amine groups to four amine groups per molecule where the amine groups are a primary or secondary amines, alkoxylated amines having at least two terminal amine groups per molecule, and a compound containing at least two of the following: aliphatic primary hydroxyl, aliphatic secondary hydroxyl, primary amine, secondary amine and carboxylic acid groups within the one molecule.

Or the polyester polyol is selected from a reaction mixture primarily of adipic acid or other diacids with diethylene glycol, ethylene glycol or butane diol.

The second component may be produced by the reaction product of a diamine, triamine or tetramine component with an activated vinyl component selected from the group consisting of dialkyl maleate, dialkyl fumarate, an acrylic acid ester and vinyl ester, wherein the reaction ratio is from about one equivalent of amine functionality to about one equivalent of vinyl functionality to about four equivalents of amine functionality to about one equivalent of vinyl functionality.

The second component may be a blend of a polyol component and an aspartate molecule having from about 1% to about 99% polyol component and from about 99% to about 1% aspartate, wherein at least one of the polyol component and the aspartate molecule has a functionality towards isocyanate of at least 2.1 active hydrogen groups per diisocyanate molecule and a viscosity from about 250 cps to about 5000 cps at 25 degrees C.

The urethane polymer matrix may be crosslinked.

The crosslinked urethane polymer matrix may be configured to start degrading in the body within about 1 month to about 24 months after implantation in the body.

The crosslinked urethane polymer matrix may be configured to lose at least 50% of its original mechanical strength after 6 months in the body.

The crosslinked urethane polymer matrix may be configured to lose at least 80% of its original mechanical strength after 12 months in the body.

The polymer implant may be prepared prior to implantation.

The polymer implant may be prepared in situ.

The high modulus fiber reinforcing component may be braided and may comprise a rod having a triangular cross-section.

The polymer implant may be prepared prior to implantation.

The high modulus fiber reinforcing component may be braided and may comprise a rod having a circular cross-section.

The rod may be cannulated.

Cannulation may be created by forming the polymer implant over a mandrel and then removing the mandrel after the implant is cured.

The polymer implant may comprise at least two high modulus fiber reinforcing components each comprising a braided rod having a triangular cross-section, and further wherein the at least two high modulus fiber reinforcing components combine to form larger structures.

The polymer implant may be formed into a shape selected from the group consisting of a screw, a rod, a pin, a nail and a bone anchor.

In one form of the invention, there is provided a method for treating a bone, the method comprising: selecting at least one high modulus fiber reinforcing component to be combined with a urethane polymer matrix so as to together form a polymer implant capable of supporting the bone; positioning the at least one high modulus fiber reinforcing component in a cavity in the bone; flowing the urethane polymer matrix into the cavity in the bone so that the urethane polymer matrix interfaces with the at least one high modulus fiber reinforcing component; and transforming the urethane polymer matrix from a flowable state to a non-flowable state so as to establish a static structure for the polymer implant, such that the polymer implant supports the adjacent bone.

The cavity in the bone may comprise the intramedullary canal.

The intramedullary canal may be accessed through a hole having a diameter smaller than the diameter of the intramedullary canal.

The hole may extend at an acute angle to the intramedullary canal.

The at least one high modulus fiber reinforcing component may be flexible, and the at least one high modulus fiber reinforcing component must be flexed in order to pass through the hole and into the intramedullary canal.

The at least one high modulus fiber reinforcing component may be flexible both radially and longitudinally.

The at least one high modulus fiber reinforcing component may comprise a plurality of reinforcing elements, wherein each of the reinforcing elements is individually capable of being passed through the hole, and further wherein the plurality of reinforcing elements collectively form a structure too large to be passed through the hole.

The at least one high modulus fiber reinforcing component may comprise at least one from the group consisting of a flexible reinforcing sheet, a flexible reinforcing rod, and particulates.

The at least one high modulus fiber reinforcing component may comprise a flexible reinforcing sheet in the form of a tube.

The at least one high modulus fiber reinforcing component may comprise at least two flexible reinforcing sheets arranged concentrically.

The at least one high modulus fiber reinforcing component may comprise a flexible reinforcing sheet in the form of a rolled sheet.

The at least one high modulus fiber reinforcing component may comprise a flexible reinforcing sheet having an arcuate cross-section.

The at least one high modulus fiber reinforcing component may comprise a flexible reinforcing sheet having a planar cross-section.

The at least one high modulus fiber reinforcing component may comprise a flexible reinforcing sheet comprising filaments formed into a textile.

The at least one high modulus fiber reinforcing component may comprise a flexible reinforcing sheet comprising filaments connected by a film.

The at least one high modulus fiber reinforcing component may comprise a flexible reinforcing rod comprising filaments held together.

The at least one high modulus fiber reinforcing component may comprise a flexible reinforcing rod and the filaments are held together by an outer sheath.

The outer sheath may comprise filaments formed into a textile.

The at least one high modulus fiber reinforcing component may comprise a flexible reinforcing rod and the filaments are held together by a compacted connecting structure of a textile or film.

The connecting structure may be compacted by at least one of winding and compressing.

The at least one high modulus fiber reinforcing component may comprise a flexible reinforcing rod and the filaments are held together by a binder.

The at least one high modulus fiber reinforcing component may comprise particulates.

The at least one high modulus fiber reinforcing component may comprise at least one flexible reinforcing sheet and at least one flexible reinforcing rod.

The at least one flexible reinforcing sheet and the at least one flexible reinforcing rod may be selected so as to form the polymer implant with a desired stiffness.

The polymer implant may have a stiffer central region and less stiff distal and proximal ends.

The polymer implant further may comprise a containment bag, and the at least one high modulus fiber reinforcing component may be positioned within the containment bag after the containment bag has been positioned within the cavity in the bone.

In one form of the invention, there is provided a method for treating a bone, the method comprising: selecting at least one pre-formed polymer implant created from at least one high modulus fiber reinforcing component combined with a urethane polymer matrix so as to together form a polymer implant capable of supporting the bone; positioning the at least one pre-formed polymer implant in a cavity in the bone; flowing a urethane polymer matrix into the cavity in the bone so that the urethane polymer matrix interfaces with the at least one pre-formed polymer implant; and transforming the urethane polymer matrix from a flowable state to a non-flowable state so as to establish a static structure for the polymer implant, such that the polymer implant supports the adjacent bone.

The polymer implant may further comprise a containment bag, and the at least one high modulus fiber reinforcing component may be positioned within the containment bag after the containment bag has been positioned within the cavity in the bone.

In one form of the invention, there is provided a method for treating a bone, the method comprising: selecting at least one high modulus fiber reinforcing component which is pre-loaded with a urethane polymer matrix just prior to implantation so as to together form a polymer implant capable of supporting the bone once fully cured; positioning at least one high modulus fiber reinforcing component in a cavity in the bone; flowing additional urethane polymer matrix into the at least one high modulus fiber reinforcing component so that the urethane polymer matrix exudes from the surfaces of the at least one high modulus fiber reinforcing component and interfaces with the surrounding bone cavity; and transforming the urethane polymer matrix from a flowable state to a non-flowable state so as to establish a static structure for the polymer implant, such that the polymer implant supports the adjacent bone and or approximated soft tissue.

Composite Implant Utilizing a Resin Injectable Matrix Material

In one form of the invention, the composite implant comprises a high modulus fiber reinforcing component and resin injectable matrix material.

The high modulus fiber reinforcing component may be of the sort disclosed above.

The resin injectable matrix material may be an acrylic resin composition comprising a mixture of prepolymerized acrylic resins or styrene acrylic resins having molecular weights from about 200 to 20,000 daltons and acrylic monomers selected from at least one of the following: methacrylic acid, methyl methacrylate, ethyl methacrylate, butyl methacrylate, acrylic acid, methyl acrylate, ethyl acrylate, butyl acrylate ethylene glycol diacrylate, ethylene glycol dimethacrylate, trimethylol propane triacrylate and trimethylol propane triamethacrylate, and an organic peroxide free radical initiator, with the mixture having an initial viscosity from about 200 cps to about 5000 cps at 20-25 degrees C. The acrylic resin composition described above may also have additional additives such as inorganic fillers, stabilizers to prevent cure of the acrylic monomers during storage and activators to accelerate the free radical cure of the acrylic system.

The resin matrix may also be a polyurethane having terminal isocyanate functionality and a viscosity from about 800 cps to about 10,000 cps at the temperature when the urethane resin matrix is applied to the high modulus fibers and a viscosity of at least 50,000 cps at 20-25 degrees C. In a non-in situ embodiment, the resin matrix may have a terminal isocyanate functionality and be applied to the high modulus fiber at a temperature from about 100 degrees C. to about 200 degrees C., the high modulus fiber having been surface coated with a sizer or primer that provides additional adhesion between the urethane resin matrix and the high modulus fiber and can optionally act as a secondary catalyst for further molecular weight increase of the urethane resin matrix and adhesion to the high modulus fiber.

In one form of the present invention, the composite implant comprises a resin matrix and a high modulus fiber reinforcing component, wherein the compressive modulus ratio between the cured resin injectable matrix material and the high fiber reinforcing component is from about 1:3 to about 1:20, and the flexural modulus ratio between the cured resin injectable matrix material and the high fiber reinforcing component is about 1:3 to about 1:10. The resin injectable matrix material may be applied to the high modulus fiber component of the composite implant in a continuous process, with the resin injectable matrix material having a viscosity (at application temperature) of from about 2 Pas to about 2000 Pas, with fiber content of from about 5 volume percent to about 75 volume percent. The high fiber reinforcing component may be selected from at least one of the following materials: E-glass, bio glass, soluble glass, resorbable glass, carbon fiber, polyaramid fiber, PET fiber, ceramic fiber, PEEK fiber, fibers formed from homopolymers or copolymers of one or more monomers selected from D lactic acid, L lactic acid dilactides of D and L isomers, glycolic acid, and/or combinations thereof.

In another embodiment of the present invention, the composite implant comprises a high fiber reinforcing component which comprises a series of single filaments, woven filaments or a composite mesh containing one or more different compositional fibers. The high modulus fiber reinforcing component may comprise a very high modulus fiber (e.g., a fiber having a modulus greater than about 80 GPa compressive strength) and a low modulus thermoplastic fiber (e.g., a fiber having a modulus less than 8 GPa), where the thermoplastic fiber is pre-melted so as to provide a retaining structure for the rigid fibers.

In another embodiment of the composite implant, the resin injectable matrix material is an acrylic resin composition comprising a mixture of prepolymerized acrylic resins (or styrene acrylic resins) having molecular weights from about 200 to 20,000 daltons, and acrylic monomers selected from at least one of the following: methacrylic acid, methyl methacrylate, ethyl methacrylate, butyl methacrylate, acrylic acid, methyl acrylate, ethyl acrylate, butyl acrylate ethylene glycol diacrylate, ethylene glycol dimethacrylate, trimethylol propane triacrylate and trimethylol propane tri-amethacrylate, and an organic peroxide free radical initiator, with the mixture having an initial viscosity from about 200 cps to about 5000 cps at 20-25 degrees C. The acrylic resin composition described above may also comprise additional additives, e.g., inorganic fillers, stabilizers to prevent cure of the acrylic monomers during storage, and/or activators to accelerate the free radical cure of the acrylic system. The high modulus fiber reinforcing component may have a surface which is coated with a sizing agent, or a primer, which provides additional adhesion between the acrylic resin matrix and the high modulus fiber reinforcing component, and which can optionally act as a secondary catalyst for the polymerization of the acrylic monomers. In addition, the high modulus fiber reinforcing component may be surface coated with an amino functional material selected from at least one of the following materials: amino silanes, lysine, polyamines, amino acids and polyamino acids.

In another embodiment of the present invention, the resin injectable matrix material comprises a polyurethane having terminal isocyanate functionality and a viscosity from about 800 cps to about 10,000 cps (at the temperature when the urethane resin matrix is applied to the high modulus fiber reinforcing component) and a viscosity of at least 50,000 cps at 20-25 degrees C. The resin injectable matrix material may also comprise a polyurethane having terminal isocyanate functionality, which is applied to the high modulus fiber at a temperature from about 100 degrees C. to about 200 degrees C. The high modulus fiber reinforcing component may be surface coated (e.g., with a sizer or primer) that provides additional adhesion between the urethane resin injectable matrix material and the high modulus fiber reinforcing component, and which can optionally act as a secondary catalyst for further molecular weight increase of the urethane resin injectable matrix material and can facilitate adhesion to the high modulus fiber. The high modulus fiber reinforcing component may also be surface coated with an amino functional material selected from at least one of the following materials: amino silanes, lysine, polyamines, amino acids, and polyamino acids.

In another embodiment of the present invention, the resin injectable matrix material is a polyurethane, and the composite implant may also contain residual isocyanate groups in the composite structure such that they can be stored in a dry inert atmosphere without further crosslinking reactions, and then, when applied in the body (i.e., where moisture is present), will further cure until no residual isocyanate groups are present. This composite implant may also comprise up to about 4% by weight of polymer-bound isocyanate groups in the structure and/or the composite implant may provide a foamed surface structure in the body during final cure so as to accommodate the special difference between the polymer implant and the cavity constructed to accommodate the polymer implant, thus providing improved strength and stiffness to the repaired bone area.

Bioresorbable and Biodegradable Composite Materials

In another form of the invention, there is provided a composition of matter that results in high modulus composite materials that are capable of biodegrading or bioabsorbing due to ambient (e.g., bodily or environmental) conditions. The utility of the materials range from the aforementioned medical implants to other medical devices (e.g., syringes) to a wide variety of non-medical applications, e.g., packaging materials (such as packages, packaging, disposable pallets, etc.), landscaping films, trash bags, etc.

More particularly, the removal and handling of waste products is a common issue faced by local and federal municipalities within many countries. Land fill availability, accessibility, and restrictions have created the need for complex re-cycling programs at increased expense to taxpayers and governments.

The rapid technological innovations in polymer processing and forming for structural development has led to increases in long-life waste materials, taking decades to millennia to degrade, therefore requiring very extensive re-cycling programs or potentially polluting reduction means such as through burning or solvent reactions. In addition, and frequently, the usable life spans of the polymer structures are low due to limitations in the material properties. Non-degradable polymers are very quickly manufactured through processes such as injection molding, extrusion, pultrusion, heat pressing, etc., however, the final material may not be strong enough for some applications. The polymers can be strengthened through the addition of high modulus fiber particles, however, the resulting increase in stiffness is usually offset by making the material brittle. Full composites are designed to provide the targeted strength profiles for very long life or high strength materials that polymers alone do not provide, however, they are commonly associated with the difficulty in waste management previously described.

Current degradable polymers are effective but are limited in applications due to strength limitations. The addition of soluble high modulus particulate serves to stiffen the material but adds a brittleness as described above.

Thus it will be seen that a new approach is needed for reducing the burden of waste management on society at large.

The present invention provides a new approach for creating high strength mechanical structures for materials with defined useful life-cycles that will biodegrade or bioabsorb due to the normal environment envisioned at end of life.

The present invention also provides a new approach for using such material degradation to provide utility or delivery of a local alteration of environmental conditions.

More particularly, the present invention comprises the provision and use of a novel composite comprising a biodegradable or bioabsorbable flowable polymer (i.e., the injectable matrix material, sometimes referred to simply as "the matrix") and a high modulus reinforcing element to create useful structures. The composite is created from at least one reinforcing element, embedded within a matrix. The final composite structure can be either anisotropic or isotropic, depending on the requirements of the final construct. The final composite is susceptible to complete or partial degradation or dissolution due to ambient (e.g., bodily or environmental) conditions including, but not limited to, immersion in water, saline (physiologic, oceanographic, etc.), the presence of naturally-occurring or intentionally-added enzymes or chemicals, etc. Preferably, the materials are designed for their working environment. As an example, structural storage of food goods, once depleted, may be designed to rapidly degrade in high salt content water such as the ocean, allowing ocean-going vessels to reduce waste without adversely affecting the environment.

Furthermore, the present invention is capable of degrading into sub-components engineered such that the local area (e.g., the body or the environment) is beneficially affected. The duration, intensity, and sequence of the release of remnants of the degradation process can be designed to produce pH shifts in a local area (e.g., the body or the environment) or to release other compounds into the local area (e.g., the body or the environment). For example, during the degradation of a composite structure, there may be a rapid release of remnants for a burst of either acidic or basic pH shift, followed at a later period of time by the release of buffering solutions to re-alter the local area (e.g., the body or the environment). As a more specific example, a bio-degradable textile may be produced that is highly flexible but tensile-reinforced. The textile, in the form of a fabric, may be designed for coverage over garden materials as initial protective barriers that degrade over a time period of weeks into either basic or acidic materials beneficial to the plant material below the protective barrier. High tensile strength allows the composite material to be spread over large areas by industrial mechanisms without fear of tearing the protective material.

The matrix material is preferably polymeric and preferably bioabsorbable and/or biodegradable. The matrix material may be an organic polymer that can be formed via a polymerization process and/or the matrix material may also comprise a bioactive filler material and/or a degradation or deposition agent.

The reinforcement material is preferably a bio-degradable, water-soluble, bio-absorbable or carbon-neutral material with a modulus engineered for higher tensile or compressive properties than the surrounding matrix material. The reinforcing elements can be particulate, nano-sized, or fiberous in nature, preferably with an aspect ratio of from about 1:5 to >1:100.

The reinforcing elements can be coated with another material that provides, but is not limited to, one of more of the following features: enhanced bonding to the matrix material; increase in reinforcement dimensions; modulation of hydro-diffusion access to the reinforcement material, etc.

Optionally, the matrix material may contain a biocompatible solvent, with the solvent reducing viscosity so as to allow the matrix material to flow easily, and with the solvent thereafter diffusing from the composite so as to facilitate or provide stiffening and/or to impart or alter the porosity of the matrix material.

Thus it will be seen that the present invention comprises a new approach for creating high strength composite structures with defined useful life-cycles that will biodegrade or bioabsorb due to the normal environment envisioned at the end of life.

The present invention also provides a new approach for using this composite degradation to provide utility, including the delivery of a local alteration of the host area (e.g., the body or the environment).

One preferred embodiment is the use of a thermoplastic matrix-based composite with disparate reinforcing elements, the mix of which provides increased material strength and advantages in chemical interactions such that degradation time and the effects on the local area (e.g., body or environment) are controlled.

In another preferred embodiment, a thermosetting matrix material is combined with disparate reinforcing elements, the mix of which provides increased material strength and advantages in chemical interactions such that degradation time and the effects on the local area (e.g., body or environment) are controlled.

The present invention provides a new approach for creating high strength composite structures with defined useful life-cycles that will biodegrade or bioabsorb due to the normal environment envisioned at end of life.

The present invention also provides a new approach for using such material degradation to provide utility or the delivery of a local alteration of the host area (e.g., the body or environment) conditions.

Composite Material.

The present invention comprises the provision and use of a novel composite comprising a biodegradable or bioabsorbable flowable polymer (i.e., the matrix) and biodegradable or bioabsorbable high modulus reinforcing elements to create useful composite structures. In one preferred form of the present invention, the composite comprises a thermoset (i.e., the matrix) with high modulus, high bioglass content (i.e., the reinforcing elements). The composite is preferably configured for liquid injection and subsequent setting, although it may also be preformed. In one preferred form of the invention, the matrix comprises polyurethane due to its promotion of high strength and biodegradability. The composite comprises at least one reinforcing element, embedded within a matrix. The final composite material can be either anisotropic or isotropic, depending on the requirements of the final construct. The final composite is susceptible to complete or partial degradation or dissolution due to the host area (body or environmental) conditions including, but not limited to, immersion in water, saline (physiologic, oceanographic, etc.), the presence of naturally-occurring or intentionally-added enzymes or chemicals. Preferably, the composite is designed for its work environment. As an example, structural storage of food goods, once depleted, may be designed to rapidly degrade in high salt content water such as the ocean, allowing ocean going vessels to reduce waste without adversely affecting the environment.

Options of final practical use may include pre-cured objects requiring significant but sub-metal structural strength. The invention lends itself to modular assembly with a thermoplastic or thermoset such as a polyurethane thermoset adhesive. The present invention also lends itself to substantially any application wherein the embedded reinforcing elements have their access to water restricted prior to the desired point of elimination, at which time water access to the bioabsorbable fiber releases ions as agents that change the pH and assist catalytic hydrolysis of the polyurethane and the subsequent biodegradation according to established test methods like ASTM D6400, D7081, etc.

In a preferred form, bioabsorbable glass (i.e., the reinforcing elements) is present from about 5 Vol % to about 65 Vol % of the composite. Since this is a biodegradable process, ordinary glass and other ceramic/metal fibers (including carbon fiber, carbon fibrils and carbon nanoparticles), which are not considered to be organic carbon, are not included in the organic carbon biodegradation process. Therefore, the reinforcing elements can also include inorganic particles that may or may not act as further agents for degradation such as, but not limited to, fibers and particles of wollastonite, talcs, clays, metal silicates, etc.

In the present invention, a set of bio-degradable ingredients are used to produce materials with higher moduli than a bio-degradable polymer alone, even when reinforced with fiber particles. The composite is formed from the basic building blocks of the matrix and reinforcing elements, wherein the reinforcing elements may be formed using textile engineering techniques and primarily continuous, bio-degradable, bio-resorbable or bio-neutral fibers.

Multiples of these fibers (i.e., the reinforcing elements), preferable with aspect ratios of at least 20:1 (length to width), are preferably used to form structures capable of being completely immersed and bonded with a thermoset-, thermoplastic- or acrylic-based bio-degradable, bio-resorbable or bio-neutral matrix material to form a desired shape once the matrix material has been transformed from a flowable to non-flowable state.

The required strength of the composite can be customized and distributed by using an appropriate amount of distributed "fiber" reinforcing elements within the homogeneous matrix. The ratio of fiber volume:matrix volume proportionately determines the ultimate strength of the structure. Additionally, the form of the fibers as they are constructed within the reinforcing elements determines where and how that strength is achieved. Fibers arranged in columnar axial supports shift implant strength to compression, tension, and bending. Angular cross-fibers (termed bias, often seen in weaving or braids) shift strength to torsional resistance and hoop strength, thereby reducing the risk of catastrophic failures.

Matrix Material.

The matrix material is preferably polymeric and bioabsorbable and/or biodegradable in response to regional (bodily or environmental) stimuli such as, but not limited to, water, saline, and naturally or artificially-introduced enzymes. The matrix material may be a synthetic polymer or an organic polymer that can be formed via a polymerization process flowable under thermoplastic processes, a polymer requiring thermosetting processes or acrylic materials. The matrix may also comprise a bioactive filler material and/or a degradation or deposition agent.

In one preferred embodiment, the matrix is a thermoplastic solution where the introduction of bioabsorbable glass and bioglass (i.e., the reinforcing elements) assists the ambient hydrolytic breakdown of biodegradable polymers which are currently only broken down at elevated temperatures. Thus, the use of such reinforcing elements to accelerate the hydrolytic breakdown of the matrix material is particularly advantageous where effective hydrolysis must take place at bodily temperatures or temperatures acceptable to the local environment. Polymers specifically sensitive to this inventive approach include, but not limited to, are polylactic acid homo and copolymers, polycaprolactone, polybutylene succinate homo and copolymers, polybutylene succinate co adipate, polyethylene glycol terephthalate co adipate, poly butylene glycol adipate co terephthalate, etc. Typically, catalytic levels or sub 10% levels of bioabsorbable glass is used in these applications in powder, chopped fiber or continuous fiber form.

The thermoplastic composite system may also include 0.1% to 20% of an inorganic material that, when immersed in an aqueous environment at temperatures of about 5 degrees C. to about 40 degrees C., and having a pH from 5.5 to 8, will result in the aqueous micro-environment of the composite component to change by at least 0.5 pH, and preferably about 1.5 to 3 pH, thus accelerating the hydrolytic breakdown of the matrix (e.g., polyester or polyester polyurethane) components so that the molecular weight is reduced by a factor of 4 to 20 in the defined timescale, making the residual low molecular weight fragments extremely brittle in nature and susceptible to microbial attack.

The matrix material may also be a multi-component polymer system that is mixed immediately prior to final structural formation. Optionally, the matrix material may contain a biocompatible solvent, with the solvent reducing viscosity so as to allow the matrix material to flow easier, and with the solvent thereafter rapidly diffusing so as to facilitate or provide stiffening or curing of the composite structure. The solvent may also be used to alter the porosity of the matrix material.

In one preferred embodiment of the present invention, polyurethanes are used as the matrix material, although other suitable chemistry systems will be apparent to those skilled in the art. The polyurethanes are produced through the reaction of difunctional, or multifunctional, or polyfunctional, isocyanate molecules having at least two reactive functional groups per molecule, with a difunctional or multifunctional compound containing two or more active hydrogen (including water) groups capable of reacting with an isocyanate group, such active hydrogen groups may include primary and secondary aliphatic hydroxyl materials and amines, primary, secondary and aromatic amine, aliphatic and aromatic thiols, urethane and urea groups.

Suitable isocyanates useful in the practice of this invention include, but are not limited to, aromatic diisocyanates such as 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyldimethylmethane diisocyanate, dibenzyl diisocyanate, naphthylene diisocyanate, phenylene diisocyanate, xylylene diisocyanate, 4,4'-oxybis(phenylisocyanate) or tetramethylxylylene diisocyanate; aliphatic diisocyanates such as tetramethylene diisocyanate, hexamethylene diisocyanate, dimethyl diisocyanate, lysine diisocyanate, lysine triisocyanate, methyl lysine diisocyanate, 2-methylpentane-1,5-diisocyanate, 3-methylpentane-1,5-diisocyanate or 2,2,4-trimethylhexamethylene diisocyanate; and alicyclic diisocyanates such as isophorone diisocyanate, 4, 4' methylene bis(cyclohexyl isocyanate) (HMDI) cyclohexane diisocyanate, hydrogenated xylylene diisocyanate, hydrogenated diphenylmethane diisocyanate, hydrogenated trimethylxylylene diisocyanate, 2,4,6-trimethyl 1,3-phenylene diisocyanate.

The present invention comprises the use of these same multi-functional isocyanates with multifunctional amines or multifunctional substituted amines, multifunctional ketimines, multifunctional aldimines, isocyanurates or biurets. By way of example but not limitation, such multi-functional amines may include hexamethylene diamine, isophorone diamine, and lysine. Examples of substituted amines may include N-substituted diaspartic acid derivatives. Examples of multifunctional ketimines and aldimines may be made from the multifunctional amines mentioned previously and methyl isobutyl ketone or isobutyraldehyde.

When a biodegradable implant is desired, the aliphatic isocyanates are generally favored. In one embodiment of the present invention, the aliphatic isocyanates are preferred.

In a preferred embodiment of the present invention, the isocyanate component is reacted with a polyol to produce a polyurethane. Suitable polyols include, but not limited to, polycaprolactone diol and polycaprolactone triol. Suitable dihydroxy compounds which may be utilized in the practice of this invention include, but are not limited to, ethylene glycol, propylene glycol, butylene glycol, hexylene glycol and polyols including polyalkylene oxides, polyvinyl alcohols, and the like. In some embodiments, the polyol compounds can be a polyalkylene oxide such as polyethylene oxide ("PEO"), polypropylene oxide ("PPO"), block or random copolymers of polyethylene oxide (PEO) and polypropylene oxide (PPO). Higher functional polyol compounds are also useful and can include glycerin, 1,2,4-butanetriol, trimethylol propane, pentaerythritol and dipentaerythritol, 1,1,4,4-tetrakis(hydroxymethyl)cyclohexane. Other useful polyolsactive hydrogen containing molecules can include ethanolamine, diethanolamine, triethanol amine and N,N,N',N'-Tetrakis(2-hydroxyethyl)ethylenediamine), ethylene diamine, diethylene triamine, triethylene tetramine, tetraethylene pentamine, aspartate reaction products of a vinyl ester with a diamine, triamine or tetramine such as diethyl maleate, diethyl fumarate, acrylate and methacrylate esters with a diamine or triamine molecule.

The polyol materials discussed above may be used alone or, optionally, as mixtures thereof. The foregoing materials are merely examples of useful components for producing polyurethanes and should not be viewed as a limitation of the present invention. These higher functional polyol materials will produce highly cross-linked polyurethanes with high hardness and stiffness.

In preferred embodiments, the multifunctional hydroxyl material may include at least one bioabsorbable group to alter the degradation profile of the resulting branched, functionalized compound. Bioabsorbable groups which may be combined with the multifunctional compound include, but are not limited to, groups derived from glycolide, glycolic acid, lactide, lactic acid, caprolactone, dioxanone, trimethylene carbonate, and combinations thereof. For example, in one embodiment, the multifunctional compound may include trimethylol propane in combination with dioxanone and glycolide. Methods for adding bioabsorbable groups to a multifunctional compound are known in the art. Where the multifunctional compound is modified to include bioabsorbable groups, the bioabsorbable groups may be present in an amount ranging from about 50 percent to about 95 percent of the combined weight of the multifunctional compound and bioabsorbable groups, typically from about 7 percent to about 90 percent of the combined weight of the multifunctional compound and bioabsorbable groups. The multifunctional compound can have a weight (average molecular weight, all listed in kilodaltons) ranging from about 500 to about 50,000, typically from about 1,000 to about 3,000, and typically possesses active hydrogen functionality ranging from at least 2 to about 6, preferably from 2 to about 4.

In one preferred embodiment of the present invention, the polycaprolactone diols and, triols and tetrols provide branching sites for polyurethanes that are biodegradable.

The isocyanate is reacted with a polyol to produce a prepolymer. Methods for endcapping the polyol with an isocyanate are known to those skilled in the art. For example, a polycaprolactone diol may be combined with isophorone diisocyanate by heating to a suitable temperature ranging from about 55 degrees C. to about 80 degrees C., typically about 70 degrees C. The resulting diisocyanate-functional compound may then be stored until combined with additional polyol to form the final polyurethane product.

Reaction of the urethane prepolymer with polyol to form the final polyurethane product generally requires a catalyst to provide convenient working and cure times. Polyurethane catalysts can be classified into two broad categories, amine compounds and organometallic complexes. They can be further classified as to their specificity, balance, and relative power or efficiency. Traditional amine catalysts have been tertiary amines such as triethylenediamine (TEDA, also known as 1,4-diazabicyclo[2.2.2]octane or DABCO (a trademark of Air Products), dimethylcyclohexylamine (DM-CHA), and dimethylethanolamine (DMEA). Tertiary amine catalysts are selected based on whether they drive the urethane (polyol+isocyanate, or gel) reaction, the urea (water+isocyanate, or blow) reaction, or the isocyanate trimerization reaction (e.g., using potassium acetate, to form isocyanurate ring structure). Since most tertiary amine catalysts will drive all three reactions to some extent, they are also selected based on how much they favor one reaction over another.

Another useful class of polyurethane catalysts are the organometallic compounds based on mercury, lead, tin ((for example dibutyl tin dilaurate), bismuth ((for example bismuth octanoate), titanium complexes and zinc. Dibutyl tin dilaurate and stannous octoate are widely used catalysts in many polyurethane formulations. Other catalysts include tertian amines such as triethylene diamide. Mixtures of organometal catalysts and blends of Tertian amines can be used to obtain the preferred gelling profile. Applicable catalyst concentrations preferably range from 0.01% to 4% based on polyol content.

Reinforcing Elements.

The reinforcing elements preferably comprise a biodegradable, water-soluble, bio-absorbable or carbon-neutral material with a modulus engineered for higher tensile or compressive properties than the surrounding matrix. The reinforcing elements may also be a mix of different materials with varying strength and degradation profiles as required for the final structure or its end of life degradation environment. Additionally the reinforcement materials may be chosen from structural members constructed using textile processing means, randomly oriented fibers, chopped fibers, or nano-size or greater particulates.

Where the reinforcement elements comprise a textile, its reinforcing properties and degradation profile may be modified by changing the materials, orientation, length, shape, volume, twist, and angle of the fibers and filaments within the textile of the reinforcing elements. The fibers and filaments in a textile are preferably continuous with a high aspect ratio (length:width) preferably greater than 20:1. With the present invention, a preferred generic configuration is one with high axial fiber counts in relative balance with the biasing fiber counts and bias fiber angle. The preferred axial fiber:bias fiber ratio is between 10:90 and 90:10, depending on the desired properties. The bias fiber angle is important for additional support as tensors splitting into additional axial support and torsional and burst resistivity; they are usually set at an acute angle to intersecting fibers and filaments, but the angle may vary between 0 degrees and 90 degrees or random. In addition, the bias fibers may be used to add hydrostatic pressure to draw flowable matrix into the center of non-planar reinforcing elements and to aid in the final cross-sectional shape without altering the overall cross-sectional footprint. It will be readily understood by an individual skilled in the art that further changes to the geometry of a textile engineered reinforcement element can modify the physical capabilities of the final product including braiding the reinforcing element over a removable mandrel to produce a cannulated final reinforcing element or weaving reinforcing planes for the use with low modulus, high ductility matrices for flexible sealing fabrics. Additional design changes include, but are not limited to, changing the orientation of one or more of the reinforcing elements, and/or by changing the volume of one or more of the reinforcing elements. In addition, a textile-based reinforcing element may have the fiber volume and/or direction and/or weave and/or braid altered along its length in order to create the variable stiffness, wettability or other physical properties desired for the composite structure.

In one preferred form of the invention, the one or more reinforcing elements comprise from about 5% to 75% (by volume) of the composite implant, typically at least 20% (by volume) of the composite implant.

Examples of suitable biodegradable or bioabsorbable filaments, fibers, and particulates used to form the aforementioned reinforcing elements include, but are not limited to, polyglycolic acid (PGA), glycolide copolymers, glycolide/lactide copolymers (PGA/PLA), glycolide/trimethylene carbonate copolymers (PGA/TMC), stereoisomers and copolymers of polylactide, poly-L-lactide (PLLA), poly-D-lactide (PDLA), poly-DL-lactide (PDLLA), L-lactide, DLIDF-lactide copolymers, L-lactide, D-lactide copolymers, lactide tetramethylene glycolide copolymers, lactide/trimethylene carbonate copolymers, lactide/δ-valerolactone copolymers, lactide/ε-caprolactone copolymers, polydepsipeptide (glycine-DL-lactide copolymer), polylactide/ethylene oxide copolymers, asymmetrically 3,6-substituted poly-1,4-dioxane-2,4-diones, polyhydroxyalkanaote homopolymers, copolymers, terpolymers such as poly 3 hydroxybutyrate co 3 hydroxyvalerate poly 3 hydroxybutyrate co 4 hydroxybutyrate, polylactic acid co caprolactone, polylactic acid co glycolic acid co caprolactone block and randon copolymers poly-beta-dioxanone (PDS), poly-DELTA-valerolactone, poly-δ-caprolactone, methyl methacrylate-N-vinyl pyrrolidone copolymers, polyester amides, oxalic acid polyesters, polydihydropyrans, polypeptides from alpha-amino acids, poly-beta-maleic acid (PMLA), poly-β-alkanoic acids, polyethylene oxide (PEO), silk, collagen, derivatized hyaluronic acid, resorbable or soluble glasses, resorbable ceramic, resorbable metal and chitin polymers.

By way of further example but not limitation, suitable bio-neutral materials include natural polyesters and silks, polyvinyl alcohol, glass, ceramic, metal, and carbon fiber.

In addition, the reinforcing elements may be constructed of a variety of different fibers with different properties. For example, a thermoplastic fiber may be interwoven within portions of a higher modulus material in order to facilitate handling during cutting operations with a hot knife or, through the use of a heat gun, to reduce filament damage during storage.

Coatings for the Reinforcing Elements.

The reinforcing elements may be coated (also called sized) with an appropriate material that provides, but is not limited to, one of more of the following features: enhanced bonding to the matrix material; increase in reinforcement dimensions; modulation of hydro-diffusion access to the reinforcement material.

Compatibility among the specific components that comprise a composite structure is essential in order to ensure optimal interfacial bonding, mechanical properties, physical properties, and degradation rates. Compounds known as coupling agents, compatibilizers, or sizings, which may be incorporated into the components of the composite, serve to enhance the chemical bonding between the specific components of the composite implant. In a preferred embodiment, the interfacial bond strength between the reinforcing elements and the matrix material can be enhanced through the addition of a variety of compatibilizers, e.g., calcium phosphate, hydroxyapatite, calcium apatite, fused-silica, aluminum oxide, apatitewollastonite glass, bioglass, compounds of calcium salt, phosphorus, sodium salt and silicates, maleic anhydride, diisocyanatediisocyanates, epoxides, silanesilanes, and cellulose esters. These agents may be incorporated into, and/or applied to, the components of the composite through a number of methods, e.g., plasma deposition, chemical vapor deposition, dip coating, melt-blending, spin or spray-on. A specific example is the application of an alkyl, alkoxy silane and organo titanate coupling agent to glass fiber reinforcement in order to increase its interfacial bonding strength with the injectable matrix material.

In one preferred form of the invention, the composite is capable of degrading into sub-components engineered such that the host area (e.g., the body or the local environment) is beneficially affected. The duration, intensity, and sequence of the release of remnants of the degradation process can be designed to produce pH shifts in a local environment or to release other compounds into the local environment. For example, during the degradation of a material structure, there may be a rapid release of remnants for a burst of either acidic or basic pH shift, followed at a later period of time by the release of buffering solutions to re-alter that environment. As a more specific example, a bio-degradable textile may be produced that is highly flexible but tensile-reinforced for strength. The textile, in the form of a fabric, may be designed for coverage over garden materials as initial protective barriers that degrade (over a time period of weeks) into either basic or acidic materials beneficial to the plant located below the protective barrier. High tensile strength allows the composite to be spread over large areas by industrial mechanisms without fear of tearing.

Additions to Matrix.

If desired, both the matrix material and the reinforcing elements may also comprise a bioactive filler material.

Fillers.

The matrix material may include a filler in the form of biocompatible particles. The first or primary filler, preferably in the form of particles, may also provide porosity and enhanced permeability or pore connectivity. One suitable particulate filler material is tricalcium phosphate, although other suitable filler materials will be apparent to those skilled in the art such as orthophosphates, monocalcium phosphates, dicalcium phosphates, tricalcium phosphates, and combinations thereof. Also biodegradable glasses can be utilized as a filler.

The filler particles may comprise a degradable polymer such as polylactic acid, polyglycolic acid, polycaprolactone and co-polymers thereof. The particles may also comprise degradable polymer containing one or more inorganic fillers.

In one embodiment the inorganic filler particles have mean diameters ranging from about 1 micron to about 20 microns.

In another embodiment the porosity and compressive properties of the matrix material may be modified by using additional fillers that may be inorganic, organic or another suitable bio-neutral or biodegradable material. Such refinements include the addition of particles having mean diameters ranging from about 10 nm to about 50 microns or more, preferably from about 1 micron to 20 microns. In certain matrix materials the additional filler materials may be provided in one or more size distributions.

The composite implant can become porous after implantation so as to aid the resorption process. This porosity can be generated by various mechanisms including the preferential resorption of filler, such as calcium sulfate or α-tricalcium phosphate, bioglass or of a polymeric component. Alternatively, the formulation can include a biocompatible solvent such as DMSO that is leached out of the implant post implantation. The pores are preferably 100 μm in diameter with interconnectivity to allow bone ingrowth.

The composite implant may also include an additional porogen. In one form of the invention, the porogen is sugar or a polysaccharide, such as dextran, but other biocompatible porogens will be apparent to those skilled in the art such as crystalline materials in the form of soluble salts.

The porogen may also be in the form of a quickly dissolving fiber within the reinforcing element. The fiber may dissolve rapidly, within days for example, to create a channel for fluid transfer along the intramedullar canal, increase surface area for more rapid bio-dissolution of the remaining implant, or free up other fillers for timed migration to the local environment.

In another embodiment of the present invention, the filler, either inorganic or polymeric, may be present in combined amount ranging from about 10 to about 50 wt % of the matrix composition. In certain cases it may be desirable to have the filler content over 50 wt %. If a porogen is added, it will preferably be present in an amount ranging from about 15 to about 50 wt %.

Thus it will be seen that the present invention comprises a new approach for creating high strength mechanical structures for materials with defined useful life-cycles that will biodegrade or bioabsorb due to the normal environment envisioned at end of life.

The present invention also provides a new approach for using such material degradation to provide utility or delivery of a local alteration of the host area (e.g., bodily or environmental) conditions.

Controlling Degradation Rate of Biomedical and Non-Biomedical Devices

It is known that there are materials that can degrade, i.e., reduce their molecular weight, mass, and/or strength, until the material disintegrates into constituent particles or into material with a low enough molecular weight such that enzymes can digest the remnants. It is also known that materials can degrade at different rates under different environmental conditions such as temperature, moisture level, and/or pH. However, heretofore, a method has not existed for to control the onset and rate of degradation under non-ideal material conditions. As an example, current biodegradable materials are not stiff enough for most load-bearing applications contemplated herein. The addition of a soluble glass, such as soluble glasses that are made primarily with phosphate, will stiffen the material, increasing the number of applications for which the material is suited. However, phosphate glasses are hygroscopic and, therefore, will begin to lose mass from the outside in, losing intimal contact with the surrounding matrix and thus diminishing the benefits of the composite implant. The application of the layering techniques disclosed herein allow for tailoring and controlling the internal environment in relationship to the external environment so as to increase the shelf life and working life of the composite in order to make the product practical.

The fibers may be sized with a resorbable metal layer, such as magnesium, silver, nickel, titanium, and metal alloys such as magnesium calcium alloys. Such coatings can be applied via vapor coating, sputtering, atomic layer deposition, chemical vapor deposition, or electroplating and electroless plating. Other possible coatings can include ceramic coatings on the fibers. Such coatings can be made by the surface reaction of ethyoxysilanes such as tetraethoxysilane, methyltriethoxysilane, dimethyldiethoxysilane, or trimethylethoxysilane; polycarbosilane, or polysilazanes such as perhydropolysilazane- or polysilizane-modified polyamines.

Another possible approach for sizing utilizes inorganic salts such as metal phosphates. This approach for sizing is similar to the pretreatment process of metals, wherein acids are used to corrode the metal and thus form metal salt on the surface which delays any further degradation. Typically phosphate salts of iron, calcium, magnesium, zinc, nickel, etc. are used. The sizing can be applied to phosphate glass fibers by immersion in a suitable metal-salt solution which yield inert phosphate salts that are insoluble in water. This process is self-limiting, as the reaction takes place only as long as phosphate ions are released from the glass surface. The reaction can take place in a reactive medium such as an alcohol or glycol. A mixture of salts is preferred due the formation of smaller crystal size. This process could also be combined with an organic pretreatment. This combination of salt/organic pretreatment could also act as an adhesion promoter. After reaction, the glass fibers can be rinsed and/or vacuum dried. Multiple iterations can be performed with the same compound or different salts. It is also possible to use only a metal phosphate, and diffuse some metal ions into the glass fiber and obtain a metal clad fiber.

The reinforcement fibers can be cleaned or surface oxidized using various means described in the literature including plasma treatment, corona treatment, ozone treatment, and acidic/basic treatment. Such treatments can also be used to introduce specific chemical moieties, such as hydroxyl groups, on the surface of the fibers which can react or provide improved adhesion with the polymer matrix.

The composite implant can also include fillers that act as self-buffering or degradation-controlling agents. Suitable inorganic bases can be added, such as salts and oxides of alkaline metals, including basic mono-, di-, and tri-phosphates, calcium oxide, calcium hydroxide, magnesium oxide, magnesium hydroxide, calcium phosphate, beta tricalcium phosphate, hydroxyapatite, potassium stearate and sodium stearate. Particles of metals such as magnesium, iron, titanium, and zinc or metal alloys, such as magnesium base alloys, can also be added. Other possible fillers include water-reactive particles, such as calcium oxide or cobalt chloride. Organic bases, such as polyamines, bispidines, and proton sponges, are examples of self-buffering agents. The self-buffering or degradation controlling agents can be encapsulated in a micro- or nano-capsule, and are released under certain physiological conditions.

To control the diffusion rates into and out of the composite implant, the composite implant may be coated with a resorbable metal layer, such as magnesium, silver, nickel, titanium, and metal alloys such as magnesium calcium alloys. Such coatings can be applied via vapor coating, sputtering, atomic layer deposition, chemical vapor deposition, or electroplating and electroless plating. Such metal layers provide reduced diffusion, but can also react with water to provide basic/alkaline products that can act as buffering and degradation control agents for the polymer matrix and/or glass fibers.

Another possible approach could be ceramic coatings on the composite implant. Such coatings can be made by the surface reaction of ethyoxysilanes such as tetraethoxysilane, methyltriethoxysilane, dimethyldiethoxysilane, or trimethylethoxysilane; polycarbosilane, or polysilazanes such as perhydropolysilazane- or polysilizane-modified polyamines.

Additional Constructions.

As an example, high modulus polymer pellets can be produced in high volumes that are used in particulate blasting work to remove oils, rust, paint, etc. This can be especially important for offshore use where the transport of waste material back to shore is of particular environmental importance. The biodegradable particulate may simply be deposited into the ocean to naturally degrade. It is conceivable that the degradation process could yield pH or other shifts in local environment that provides a beneficial environment for petroleum-consuming bacterial or enzymes as well.

See Examples 41-60, 75, 79-83.

EXAMPLES

Example 1

Preparation of 50/50 prepolymer: 10.60 g polycaprolactone diol (0.02 mol), 6.00 g polycaprolactone triol (0.02 mol), both previously vacuum dried and 23.31 mL isophorone diisocyanate (0.10 mol) were stirred continuously while heating slowly to 70° C., and then stirred at 70° C. for 2 hours. The heat and stirring was stopped and the reaction was allowed to sit at room temperature overnight. Yield ~40 g clear highly viscous material.

Example 2

Preparation of 60/40 prepolymer: 15.90 g polycaprolactone diol (0.03 mol), 6.00 g polycaprolactone triol (0.02 mol), both previously vacuum dried and 27.97 mL isophorone diisocyanate (0.13 mol) were stirred continuously while heating slowly to 70° C., and then stirred at 70° C. for 2 hours. The heat and stirring was stopped and the reaction was allowed to sit at room temperature overnight. Yield ~50 g clear viscous material.

Example 3

Preparation of hexamethylenediamine aspartic acid ester: 11.62 g hexamethylenediamine (0.10 mol) and 38.86 g tert-butanol was combined, and 34.46 g diethyl maleate (0.20 mol) was added slowly. Reaction was $N_2$ blanketed and heated to 70° C. with stirring for 30 minutes. Reaction was allowed to sit at room temperature for 120 hours before removing tert-butanol via rotary evaporation at 70° C. and 215-195 mbar. Yield ~45 mL clear slightly viscous liquid.

Example 4

Preparation of isophorone diamine aspartic acid ester: 17.04 g isophorone diamine (0.10 mol) and 38.75 g tert-butanol was combined, and 34.43 g diethyl maleate (0.20 mol) was added slowly. Reaction was $N_2$ blanketed and heated to 35° C. with stirring for 15 minutes. Reaction was allowed to sit at room temperature for 120 hours before removing tert-butanol via rotary evaporation at 70° C. and 215-195 mbar. Yield ~45 mL clear slightly viscous liquid.

Example 5

Preparation of diethylenetriamine aspartic acid ester: 10.33 g diethylenetriamine (0.10 mol) and 38.74 g tert-butanol was combined, and 34.36 g diethyl maleate (0.20 mol) was added slowly. Reaction was $N_2$ blanketed and heated to 35° C. with stirring for 10 minutes. Reaction was allowed to sit at room temperature for 120 hours before removing tert-butanol via rotary evaporation at 70° C. and 215-195 mbar. Yield ~35 mL pale yellow slightly viscous liquid.

Example 6

Preparation of Polypropylene braid: A Steeger horizontal braider was used with 0.008" OD polypropylene monofilament. Braids were run with 24 sheath yarns, and the samples that were run with axials had 12 axials, all made of the same 0.008" OD PP. Samples were run over 5 mm and 10 mm diameter mandrels.

Example 7

Preparation of Polylactic acid (PLA) braid: A Steeger horizontal braider was used with 120d PLLA multifilament. Braids were run with 48 ends, and the samples that were run with axials had 24 axials, all made of the same 120d PLLA. Samples were run over 5, 7 and 10 mm diameter mandrels.

Example 8

Preparation of 1.5 mm diameter PLA braid: 1.5 mm braids were constructed around a core constructed of 90 ends of 75d PLLA, twisted at approximately 2 TPI. The outer sheath was constructed of 24 ends of 120d PLLA. A Steeger 48 end horizontal braider was used.

Example 9

Preparation of 1.5 mm diameter PLA braid with axial fibers: 1.5 mm braids were constructed around a core constructed of 90 ends of 75d PLLA, twisted at approximately 2 TPI. The outer sheath was constructed of 24 ends of 120d PLLA, and 12 axial ends of 120d PLLA. A Steeger 48 end horizontal braider was used.

Example 10

Preparation of Polyurethane: 2.60 grams of the prepolymer of Example 1 was mixed with 0.30 grams of polycaprolactone triol and 0.10 grams of glycerol at 0.13% w/w dibutyltin dilaurate. The mixture was transferred into a 3 ml syringe and placed in an oven at 37° C. to cure overnight. The sample was removed from the syringe and cut using a diamond saw to make a compression test piece. Compression testing showed that the material had a compressive stiffness of 1.1 GPa and a yield strength of 56 MPa.

Example 11

Preparation of Polyurethane: 2.60 grams of the prepolymer of Example 1 was mixed with 1.00 grams of tricalcium phosphate and 0.30 grams of polycaprolactone triol and 0.10 grams of glycerol at 0.13% w/w dibutyltin dilaurate. The mixture was transferred into a 3 ml syringe and placed in an oven at 37° C. to cure overnight. The sample was removed from the syringe and cut using a diamond saw to make a compression test piece. Compression testing showed that the material had a compressive stiffness of 1.3 GPa and a yield strength of 63 MPa.

Example 12

Preparation of Polyurethane: 2.60 grams of the prepolymer of Example 1 was mixed with 2.48 grams of tricalcium phosphate and 0.35 grams of polycaprolactone triol and 0.10 grams of glycerol 0.13% w/w dibutyltin dilaurate. The mixture was transferred into a 3 ml syringe and placed in an oven at 37° C. to cure overnight. The sample was removed from the syringe and cut using a diamond saw to make a compression test piece. Compression testing showed that the material had a compressive stiffness of 1.8 GPa and a yield strength of 71 MPa.

Example 13

Preparation of Polyurethane: 4.05 grams of the prepolymer of Example 2 was mixed with 0.50 grams of polycaprolactone triol and 0.15 grams of glycerol 0.13% w/w dibutyltin dilaurate. The mixture was transferred into a 3 ml syringe and placed in an oven at 37° C. to cure overnight. The sample was removed from the syringe and cut using a diamond saw to make a compression test piece. Compression testing showed that the material had a compressive stiffness of 1.1 GPa and a yield strength of 53 MPa.

Example 14

Preparation of Polyurethane: 4.05 grams of the prepolymer of Example 2 was mixed with 2.01 grams of tricalcium phosphate and 0.50 grams of polycaprolactone triol and 0.15 grams of glycerol 0.13% w/w dibutyltin dilaurate. The mixture was transferred into a 3 ml syringe and placed in an oven at 37° C. to cure overnight. The sample was removed from the syringe and cut using a diamond saw to make a compression test piece. Compression testing showed that the material had a compressive stiffness of 1.5 GPa and a yield strength of 69 MPa.

Example 17

Preparation of Polyurethane: 5.26 grams of the prepolymer of Example 1 was mixed with 3.81 grams of the aspartic acid ester from Example 5. The mixture was transferred to a 3 ml syringe and placed in an oven at 37° C. to cure overnight. The sample was removed from the syringe and cut using a diamond saw to make a compression test piece. Compression testing showed that the material had a compressive stiffness of 0.6 GPa and a yield strength of 29 MPa.

Example 18

Preparation of Polyurethane: 2.05 grams of the prepolymer of Example 2 was mixed with 2.17 grams of the aspartic acid ester from Example 3. The mixture was transferred to a 3 ml syringe and placed in an oven at 37° C. to cure overnight.

Example 19

Preparation of Polyurethane: 2.03 grams of the prepolymer of Example 2 was mixed with 2.43 grams of the aspartic acid ester from Example 4. The mixture was transferred to a 3 ml syringe and placed in an oven at 37° C. to cure overnight.

Example 20

Preparation of Polyurethane: 8.10 grams of the prepolymer of Example 2 was mixed with 5.70 grams of the aspartic acid ester from Example 5. The mixture was transferred to a 3 ml syringe and placed in an oven at 37° C. to cure overnight. The sample was removed from the syringe and cut using a diamond saw to make a compression test piece. Compression testing showed that the material had a compressive stiffness of 0.7 GPa and a yield strength of 20 MPa.

Example 21

Preparation of high MW DL-lactide: 5.15 grams of DL-lactide monomer was added to 0.31 grams ethylene glycol and 0.0016 grams Tin(II) 2-ethylhexanoate. Mixture heated to 120° C. for 24 hours. Clear, viscous fluid.

Example 22

Preparation of middle MW DL-lactide: 7.19 grams of DL-lactide monomer was added to 1.56 grams ethylene glycol and 0.0029 grams Tin(II) 2-ethylhexanoate. Mixture heated to 120° C. for 24 hours. Clear, slightly viscous fluid.

Example 23

Preparation of low MW DL-lactide: 7.21 grams of DL-lactide monomer was added to 3.10 grams ethylene glycol and 0.0030 grams Tin(II) 2-ethylhexanoate. Mixture heated to 120° C. for 24 hours. Clear fluid, very low viscosity.

Example 24

Preparation of Polyurethane: 2.05 grams of prepolymer from Example 2 was mixed with 0.59 grams DL-lactide from Example 21 and 0.0031 grams dibutyltin dilaurate. The mixture was transferred to a 3 ml syringe and placed in an oven at 37° C. to cure overnight.

Example 25

Preparation of Polyurethane: 2.02 grams of prepolymer from Example 2 was mixed with 0.57 grams DL-lactide from Example 22 and 0.0032 grams dibutyltin dilaurate. The mixture was transferred to a 3 ml syringe and placed in an oven at 37° C. to cure overnight.

Example 26

Preparation of Polyurethane: 2.05 grams of prepolymer from Example 2 was mixed with 0.57 grams DL-lactide from Example 23 and 0.0024 grams dibutyltin dilaurate. The mixture was transferred to a 3 ml syringe and placed in an oven at 37° C. to cure overnight.

Example 27

Preparation of Polyurethane with braid reinforcement: One 10 mm ID polypropylene braid with triaxials was filled with polyurethane from Example 13. Sample was cured at 37° C. in a cylindrical mold overnight. The sample was removed from the syringe and cut using a diamond saw to make a compression test piece. Compression testing showed that the material had a compressive stiffness of 1.3 GPa and a yield strength of 69 MPa.

Example 28

Preparation of Polyurethane with braid reinforcement: Two 10 mm ID polypropylene braids with triaxials were stacked one inside the other and filled with polyurethane from Example 13. Sample was cured at 37° C. in a cylindrical mold overnight. The sample was removed from the syringe and cut using a diamond saw to make a compression test piece. Compression testing showed that the material had a compressive stiffness of 1.0 GPa and a yield strength of 44 MPa.

Example 29

Preparation of Polyurethane with braid reinforcement: Four 10 mm ID polypropylene braids with triaxials were stacked one inside the other and filled with polyurethane from Example 13. Sample was cured at 37° C. in a cylindrical mold overnight. The sample was removed from the syringe and cut using a diamond saw to make a compression test piece. Compression testing showed that the material had a compressive stiffness of 1.3 GPa and a yield strength of 69 MPa.

Example 30

Preparation of Polyurethane with braid reinforcement: Four 10 mm ID polypropylene braids with triaxials were stacked one inside the other, and three 5 mm ID polypropylene braids with triaxials were stacked in the same way. The smaller ID braids were placed inside the four 10 mm ID braids and filled with polyurethane from Example 13. Sample was cured at 37° C. in a cylindrical mold overnight. The sample was removed from the syringe and cut using a diamond saw to make a compression test piece. Compression testing showed that the material had a compressive stiffness of 1.2 GPa and a yield strength of 63 MPa.

Example 31

Preparation of Polyurethane with braid reinforcement: One 10 mm ID polypropylene braid with triaxials was filled with polyurethane from Example 14. Sample was cured at 37° C. in a cylindrical mold overnight. The sample was removed from the syringe and cut using a diamond saw to make a compression test piece. Compression testing showed that the material had a compressive stiffness of 1.0 GPa and a yield strength of 53 MPa.

Example 32

Preparation of Polyurethane with braid reinforcement: Two 10 mm ID polypropylene braids with triaxials were stacked one inside the other and filled with polyurethane from Example 14. Sample was cured at 37° C. in a cylindrical mold overnight. The sample was removed from the syringe and cut using a diamond saw to make a compression test piece. Compression testing showed that the material had a compressive stiffness of 1.7 GPa and a yield strength of 75 MPa.

Example 33

Preparation of Polyurethane with braid reinforcement: Four 10 mm ID polypropylene braids with triaxials were stacked one inside the other and filled with polyurethane from Example 14. Sample was cured at 37° C. in a cylindrical mold overnight. The sample was removed from the syringe and cut using a diamond saw to make a compression test piece. Compression testing showed that the material had a compressive stiffness of 2.0 GPa and a yield strength of 66 MPa.

Example 34

Preparation of Polyurethane with braid reinforcement: Four 10 mm ID polypropylene braids with triaxials were stacked one inside the other, and three 5 mm ID polypropylene braids with triaxials were stacked in the same way. The smaller ID braids were placed inside the four 10 mm ID braids and filled with polyurethane from Example 14. Sample was cured at 37° C. in a cylindrical mold overnight. The sample was removed from the syringe and cut using a diamond saw to make a compression test piece. Compression testing showed that the material had a compressive stiffness of 1.7 GPa and a yield strength of 70 MPa.

Example 35

Preparation of Polyurethane with braid reinforcement: One 1.5 mm ID PLA braid with axials was loaded into a 2 mm ID tube and filled with polyurethane from Example 13 that had been degassed with no DBDL. Sample was cured at 70° C. for two days. The sample was removed from the tubing for three point bending test.

Example 36

Preparation of Polyurethane with braid reinforcement: One 1.5 mm ID PLA braid without axials was loaded into a 2 mm ID tube and filled with polyurethane from Example 13 that had been degassed with no DBDL. Sample was cured at 70° C. for two days. The sample was removed from the tubing for three point bending test.

Example 37

Preparation of Polyurethane with braid reinforcement: One 5 mm ID PLA braid without axials was loaded into a 5 mm ID tube and filled with polyurethane from Example 13 that had been degassed with no DBDL. Sample was cured at 70° C. for two days. The sample was removed from the tubing for three point bending test. Three point bend testing showed that the material had a stiffness of 1.2 Gpa and a yield strength of 39 Mpa.

Example 38

Preparation of Polyurethane with braid reinforcement: One 10 mm ID PLA braid without axials was filled with polyurethane from Example 13 that had been degassed with no DBDL. Sample was cured at 70° C. in a cylindrical mold for two days. The sample was removed from the syringe and cut using a diamond saw to make a compression test piece. Compression testing showed that the material had a compressive stiffness of 0.8 GPa and a yield strength of 39 MPa.

Example 39

Preparation of Polyurethane with braid reinforcement: One 7 mm ID PLA braid without axials was placed inside of a 10 mm ID PLA braid without axials and filled with polyurethane from Example 13 that had been degassed with no DBDL. Sample was cured at 70° C. in a cylindrical mold for two days. The sample was removed from the syringe and cut using a diamond saw to make a compression test piece. Compression testing showed that the material had a compressive stiffness of 0.5 GPa and a yield strength of 27 MPa.

Example 40

Preparation of Polyurethane with braid reinforcement: One 5 mm ID PLA braid without axials was placed inside of a 7 mm ID PLA braid without axials and both braids were placed inside of a 10 mm ID PLA braid without axials, and the entire stack was filled with polyurethane from Example 13 that had been degassed with no DBDL. Sample was cured at 70° C. in a cylindrical mold for two days. The sample was removed from the syringe and cut using a diamond saw to make a compression test piece. Compression testing showed that the material had a compressive stiffness of 0.8 GPa and a yield strength of 39 MPa.

Examples 41-50 Glass Braid Composites

Preparation of 60/40 prepolymer: 15.90 g polycaprolactone diol (0.03 mol), 6.00 g polycaprolactone triol (0.02 mol), both previously vacuum dried and 27.97 ml isophorone diisocyanate (0.13 mol) were stirred continuously while heating slowly to 70° C., and then stirred at 70° C. for 2 hours. The heat and stirring was stopped and the reaction was allowed to sit at room temperature overnight yielding ~50 g of clear viscous material.

Textile engineered braided glass fibers were prepared having 3 axial fiber bundles bound by bias fiber bundles in a glass content ratio of approximately 1:1; the bias bundles were orientated at +/−45 degrees to the axial bundles; the resulting textile having a predominantly triangular cross-section. A single braid approximately 1.9-2 mm in diameter and about 80 mm in length was placed in a PTFE tube and a selection of polyurethane formulations in the table below were injected down the tube using both injection pressure and vacuum suction to produce substantially void free constructions with approximately 50% eglass by volume. The constructions were cured at 70 degrees C. in a tight fitting stainless steel tube and cut from the PTFE tube. The cured composite pins were removed and subjected to mechanical testing. During the same operation PTFE tubes without braid reinforcements were likewise prepared so comparisons in mechanical properties of the unfilled and glass reinforced structures could be made.

Examples 41-50 use commercially available polyester polyols from King Industries (Kflex series), Perstorp (Capa) and Invista (Terin), all are known to hydrolytically breakdown over a period of time under ambient aqueous environments. The isocyanate prepolymer was the same as described in Example 2 with the polycaprolactone diol and triol being sourced from Perstorp. The polyols were pre-combined and allowed to stand to remove an air entrainment. The prepolymer described above was combined with the prepolymer blend at the ratios shown in the table which were calculated from hydroxyl value and isocyanate value contributions to provide stoichiometric cure. The mixture was degassed before injecting into the tubes to avoid air entrainment. The samples were cured at 70 degrees C. for 48 hours and then conditioned under ambient conditions before being tested for flexural strength.

| Examples | 41 | 42 | 43 | 44 | 45 | 46 | 47 | 48 | 49 | 50 |
|---|---|---|---|---|---|---|---|---|---|---|
| Polyol | | | | | | | | | | |
| Kflex 366 | 60 | | | | 60 | | | | | |
| Kflex 307 | | 60 | | | | 60 | | | | |
| Kflex XM 337 | | | 60 | | | | 60 | | | |
| Kflex 148 | | | | | | | | | 60 | 60 |
| Terin 168G | | | | 60 | | | | 60 | | |
| Capa 4101 | 30 | 30 | 30 | 30 | | | | | 30 | |
| Capa 4800 | | | | | 30 | 30 | 30 | 30 | | 30 |
| Glycerol + 10% DBTL | 10 | 10 | 10 | 10 | 10 | 10 | 10 | 10 | 10 | 10 |
| Total | 100 | 100 | 100 | 100 | 100 | 100 | 100 | 100 | 100 | 100 |
| Isocyanate prepolymer | 256 | 210 | 243 | 221 | 220 | 173 | 211 | 184 | 245 | 208 |
| Gel time (min) rt | 13 | 18 | 11 | 17 | 19 | 10 | 8 | 18 | 20 | 27 |
| Cured Resin Flex Modulus (GPa)/Failure Mode | 1.4 ductile | 0.8 ductile | 1.9 ductile | 0.7 ductile | 2.0 ductile | 1.6 ductile | 2.3 ductile | 1.6 ductile | 1.5 ductile | 2.2 ductile |
| Cured Composite Flex Modulus (GPa)/Failure mode | 15.6 ductile | 12.9 slip | 20.3 break | 16.2 slip | 18.1 slip | 16.4 ductile | 16.6 break | 11.7 ductile | 17.3 ductile | 14.8 Ductile |

The data in the table above shows the effect of the polyol type and composition on cure time and flexural modulus of the cured resin and the ability to tailor performance. Similarly the incorporation of the glass reinforcement showed substantial increases in flexural modulus by 10 to 15 fold in most cases still maintaining a ductile failure mode. This increase is substantially higher than the change in properties seen in prior examples with polypropylene and PLA fiber reinforcements.

Examples 51-60

Using the same procedure as described in Examples 41-50 a series of cured polyurethane compositions were tested for mechanical strength against glass filled composites using the E glass braid structure also described in Examples 41-50.

| Examples | 51 | 52 | 53 | 54 | 55 | 56 | 57 | 58 | 59 | 60 |
|---|---|---|---|---|---|---|---|---|---|---|
| Polyol | | | | | | | | | | |
| Capa 2504 | 45 | 35 | 30 | 35 | 30 | 45 | 35 | 30 | 35 | 30 |
| EG/Dilactide (1:2 Molar Ratio) | 45 | 35 | 30 | 35 | 30 | | | | | |
| EG/Dilactide (1:4 Molar Ratio) | | | | | | 45 | 35 | 30 | 35 | 30 |
| Capa 4101 | 0 | 20 | 30 | | | 0 | 20 | 30 | | |
| Capa 4800 | | | | 20 | 30 | | | | 20 | 30 |
| Glycerol + 10% DBTL | 10 | 10 | 10 | 10 | 10 | 10 | 10 | 10 | 10 | 10 |
| Total | 100 | 100 | 100 | 100 | 100 | 100 | 100 | 100 | 100 | 100 |
| Isocyanate prepolymer | 230 | 233 | 234 | 209 | 196 | 205 | 213 | 217 | 189 | 180 |
| Gel time (min) rt | 81 | 96 | 124 | 124 | 88 | 32 | 34 | 22 | 34 | 22 |
| Cured Resin Flex Modulus (Gpa)/ Failure Mode | 2.9 ductile | 2.4 ductile | 1.3 ductile | 1.6 ductile | 1.3 ductile | 2.6 ductile | 2.3 ductile | 2.6 ductile | 2.5 ductile | 1.5 ductile |
| Cured Composite Flex Modulus (GPa)/ Failure mode | 23.6 ductile | 17.3 slip | 18.0 break | 14.9 slip | 16.7 slip | 15.5 ductile | 13.4 break | 15.8 ductile | 8.2 ductile | 2.8 Ductile |

Examples 51-60 show the effect of a different type of polyester polyol, in this case made from the reaction of ethylene glycol and DL dilactide using the method below:

Preparation of high MW DL-lactide: 5.15 grams of DL-lactide monomer was added to 0.31 grams ethylene glycol and 0.0016 grams stannous 2-ethylhexanoate and heated to 120° C. for 24 hours producing a clear viscous fluid.

Preparation of DL-lactide diol: 7.19 grams of DL-lactide monomer was added to 1.56 grams ethylene glycol and 0.0029 grams stannous 2-ethylhexanoate. Mixture heated to 120° C. for 24 hours producing a clear slightly viscous fluid.

Preparation of low DL-lactide diol: 7.21 grams of DL-lactide monomer was added to 3.10 grams ethylene glycol and 0.0030 grams stannous 2-ethylhexanoate. Mixture heated to 120° C. for 24 hours producing a clear low viscosity fluid.

By selecting the type of dilactide polyol and also the amount, the flexural modulus of the cured resin may be changed from 1.3 GPa to 2.9 GPa which is very significant.

In addition, as with Examples 41-50, the flexural modulus of the glass filled composites may be change from 2.8 GPa to 23.6 GPa thus demonstrating the ability to tailor the physical properties of the implant material.

Example 61

A Polyurethane was prepared: 4.05 grams of the prepolymer of Examples 41-50 was mixed with 2.01 grams of tricalcium phosphate and 0.50 grams of polycaprolactone triol and 0.15 grams of glycerol 0.13% w/w dibutyltin dilaurate. 3 mm proximal entry holes and 3 mm mid-shaft lesions were created in 5 New Zealand White rabbits. A braided construct was compressed into a sheath and delivered through a catheter with an inner diameter of approximately 0.080 inch. The braided construct was inserted though the proximal entry and positioned across the mid-shaft lesion. The 60/40 matrix mixture from above was injected within and around the construct using a catheter with a distal portal. There was significant foaming due to the contact of the matrix with the water in the blood that obscured the procedure. The matrix cured in situ and formed an internal composite splint, however in some instances the matrix expanded and/or flowed into the fracture gap. After 6 weeks, lesions demonstrated healing except where the matrix had entered the fracture gap. In all cases, no abnormal bony reactions or infections occurred. This demonstrates that a modular splint can be constructed through a minimally invasive entry and will not interfere with normal bone healing using an engineered matrix reinforcement filled in series with a matrix material. It also highlights the requirement for a containment system to maintain the fracture gap as well as contain the curing of the polymer and direct expansion of the matrix.

Example 62

Soluble phosphate glass fibers were incorporated into a composite structure similar to those from Examples 41-50 by placing a bundle of sized strands approximately 1.9-2 mm in diameter and about 80 mm in length in a PTFE tube and injecting the degassed mixture of pre-polymers from Example 51 down the tube using both injection pressure and vacuum suction over many hours to produce predominantly void free composites which were cured at 70° C. The PTFE tube was cut and the cured pins removed and subjected to mechanical testing. A flexural modulus of 37 GPa was produced from the pins with further analysis demonstrating a 71% fiber volume in the sample. This demonstrates that the use of a bioresorbable glass as the reinforcements from this invention produces results similar to the aforementioned e-glass samples and that the invention can produce composites with greater than bone-like physical properties. It also demonstrated the long length of time required to fill and wet-out non-textile engineered uniaxial directed bundles with high fiber volume.

Example 63

Figure 30:
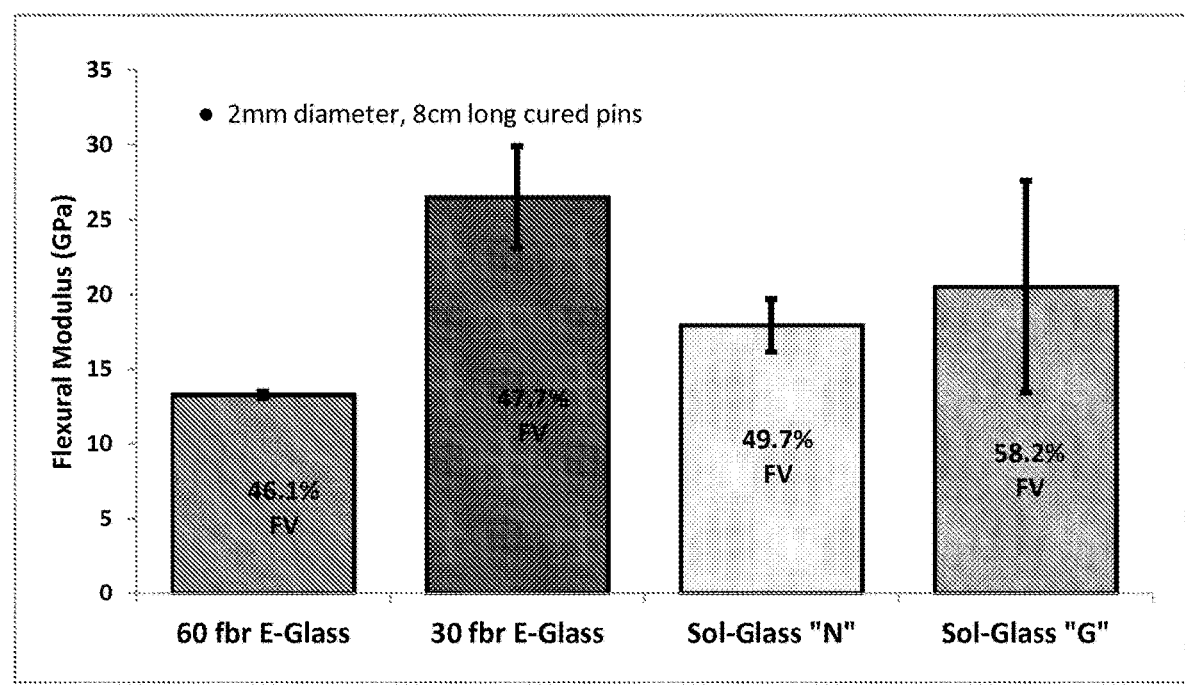
FIG. 30 shows the flexural modulus of various composite implants.

Glass fibers were procured from AGY (60 fbr glass above) and PPG (30 fbr glass above). Each glass fiber had different fiber diameters. These were compared to two types of Bio-soluble glasses axially orientated within a composite using the same polyurethane matrix from Example 51 using the same methods as described in Example 62. A comparison of flexural modulus is shown in FIG. 30 and demonstrates that the smaller "60 fiber" glass (when adjusted for fiber volume) is a good surrogate for bio-soluble glass fibers and therefore justifies the use in Examples 41-60 and those that follow.

Example 64

Glass fibers were procured from AGY (60 fbr glass above) and PPG (30 fbr glass above) and used as axial reinforcing elements in composite 2 mm pins using the same polyurethane matrix and method of construction described in Example 63. The fibers differed in two manners, the diameter of one fiber was twice that to the other (filament diameters were the same for both) however the fiber volume was kept consistent, and there was a coating difference between the two (proprietary to each e-glass manufacturer). A comparison of flexural modulus is shown in FIG. 30 with a marked difference in modulus between the two composite rods. The results demonstrate that the axial strength may be dramatically increased by through the use of an appropriate fiber coating used to compatibalize the matrix to the reinforcing elements.

Example 65

Figure 31:
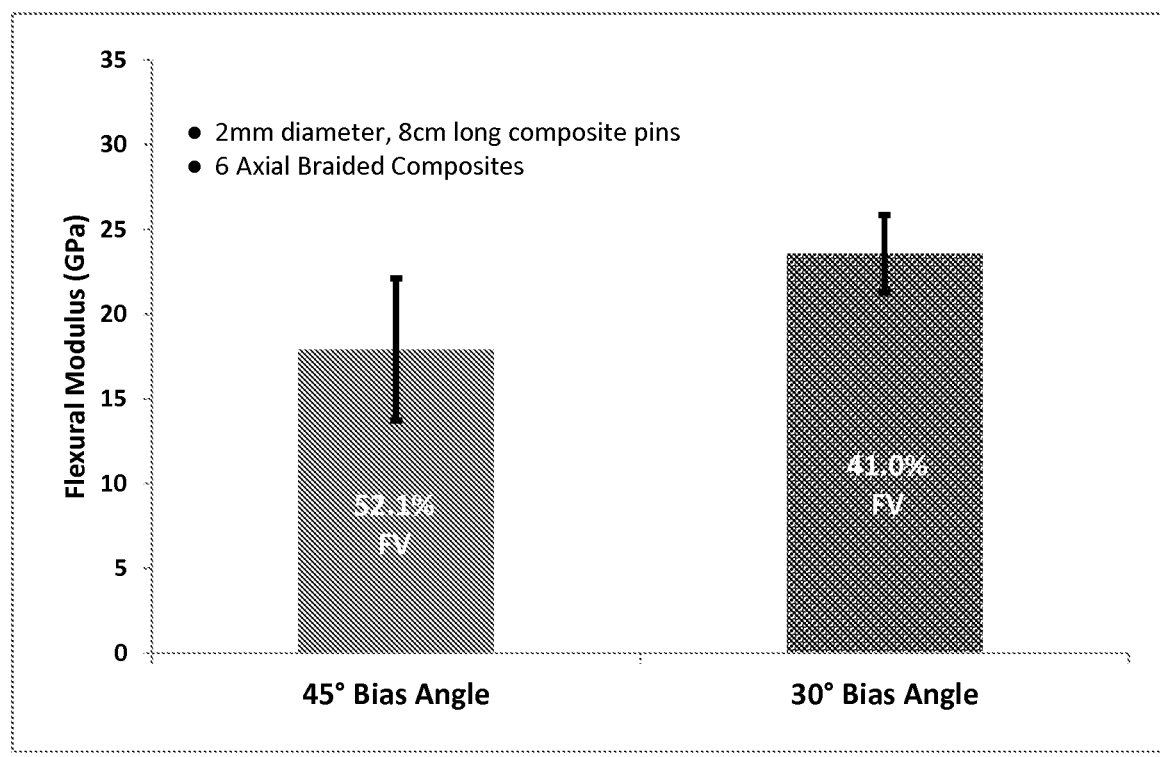
FIG. 31 shows the flexural modulus of other composite implants.

Textile E glass braids were prepared having 6 axial fiber bundles (predominantly circular cross-section) bound by bias fiber bundles in a glass content ratio of approximately 1:1 axial to bias fiber volume; in one sample the bias bundles were orientated at +/−45° to the axial bundles, in the other sample the bias bundles were orientated at +/−30° to the axial bundles. 2 mm composite pins were built using the same polyurethane matrix and method of construction described in Example 63. The flexural modulus of each are compared in FIG. 31 demonstrating that the axial contribution to structure in this invention can be increased significantly by changing the bias angle within the braided reinforcing elements.

Example 66

Figure 32:
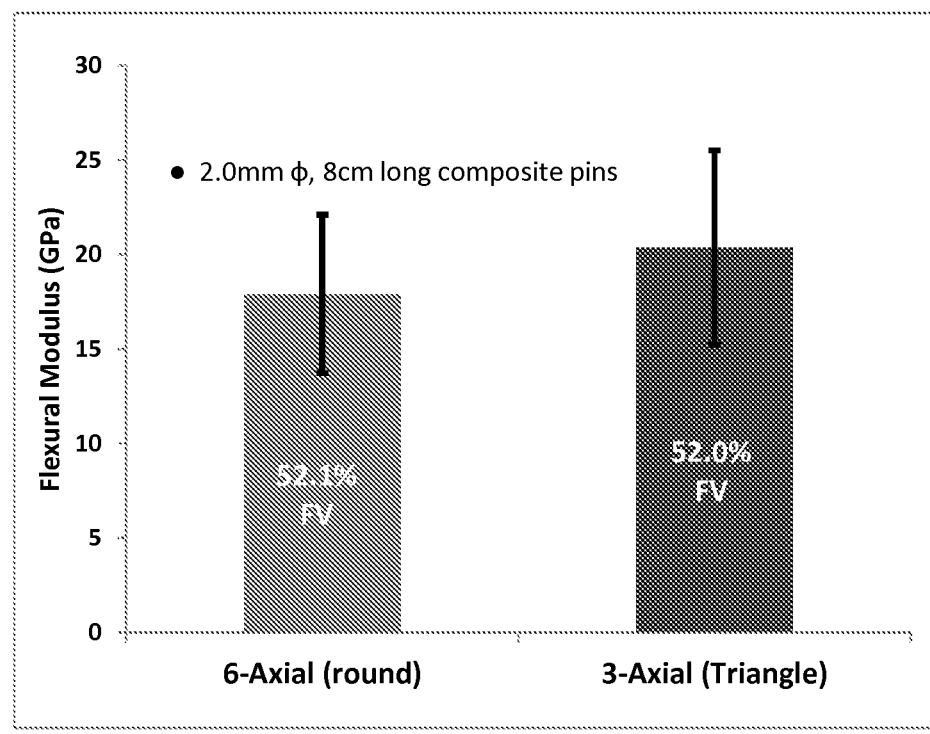
FIG. 32 shows the flexural modulus of still other composite implants.

Textile glass braids were prepared having either 6 axial fiber bundles (predominantly circular cross-section) or 3 axial fiber bundles (predominantly circular cross-section) bound by bias fiber bundles orientated at +/−45° to the axial bundles in a glass content ratio of approximately 1:1 axial to bias fiber volume and designed to contain the same volume of fiber per unit length. 2 mm composite pins were built using the same polyurethane matrix and method of construction described in Example 63. The flexural modulus of each were compared in FIG. 32, demonstrating no significant difference. Thus, the shape of a single reinforcing element will not alter its ability to reinforce a matrix.

Example 67

Figure 33:
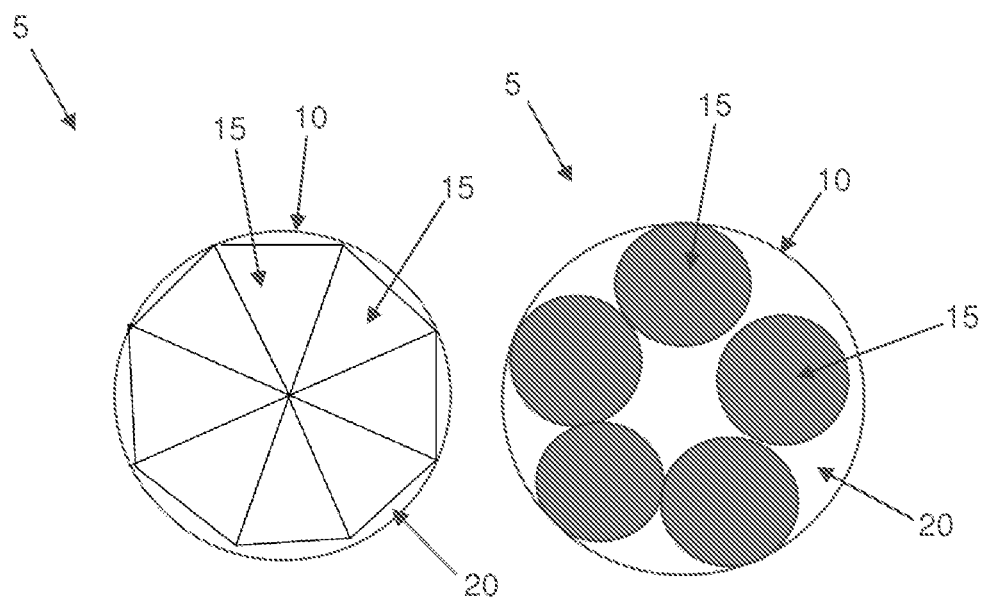
FIG. 33 shows various composite implant configurations.

Textile glass braids were prepared having 6 axial fiber bundles bound by bias fiber bundles in a glass content ratio of approximately 1:1; the bias bundles were orientated at +/−45 degrees to the axial bundles; the resulting textile having a predominantly circular cross-section. The fiber by weight per unit length braid was designed to be approximately the same as the predominantly triangular cross-section E glass braids from Examples 41-50. Multiple sections of this braid and that from Examples 41-50 were fit into a PTFE tube with an inner diameter of approximately 7.5 mm. While making three samples using each braid type, 12 of the predominantly triangular cross-section braids could fit parallel in the PTFE tube (final FV 49.4%) while only 11 of the predominantly circular cross-section braids could fit (FV 47.0%). This confirms the importance of shape to reinforcement element nesting and therefore final implant fiber volume. The concept of nesting and fit is demonstrated in FIG. 33.

Example 68

Figure 34:
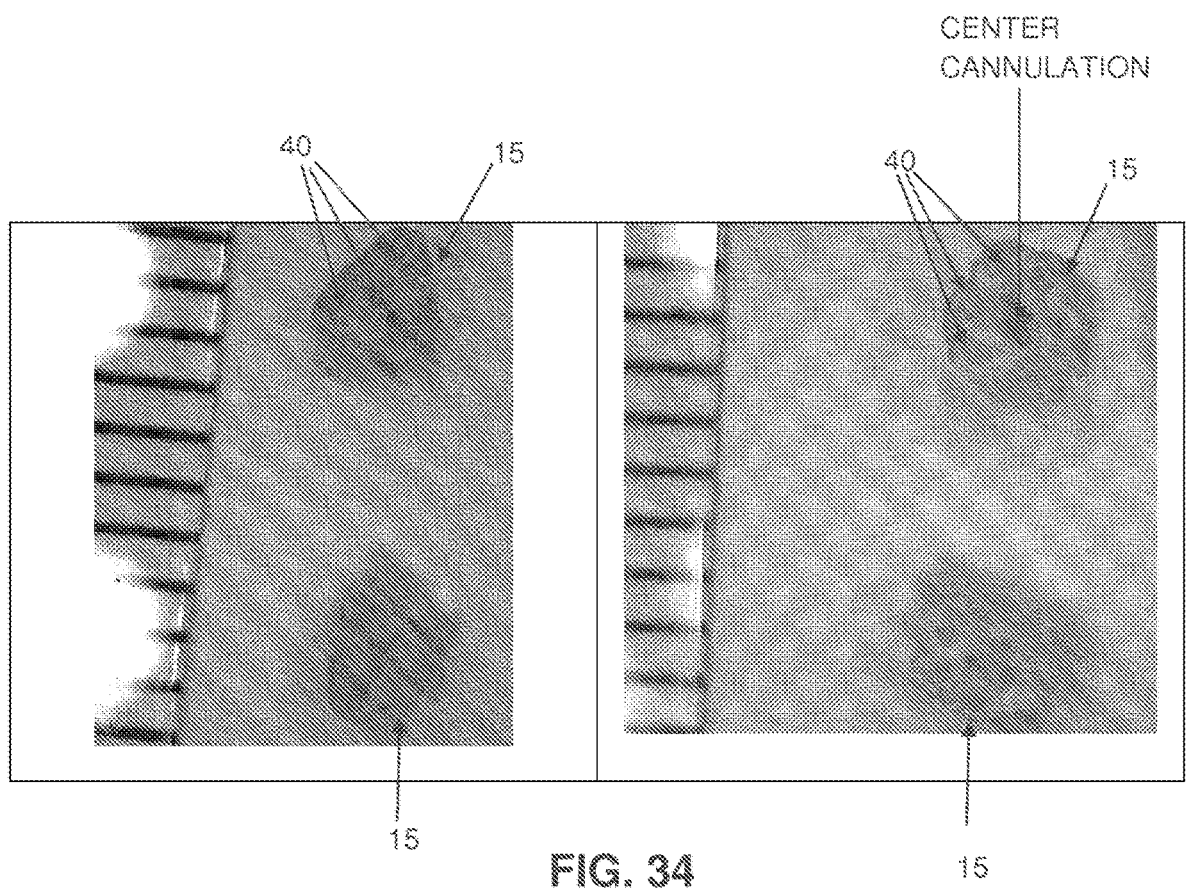
FIG. 34 shows other composite implant configurations.

The measures of flexural modulus for Example 67 showed no significant difference despite the inclusion of more reinforcement rods into the composite. The large number of reinforcement rods makes the difference in mechanical properties small, so the ratio of standard deviation to average value (expressed in %) is used to compare the variability. The triangular vs. circular cross section braids come off of the manufacturing storage roll differently. The triangular braids maintain a shape, while the circular ones come off of the roll in a rectangular shape. The rectangular shape acts to promote intra-braid nesting, creating good axially oriented columns (better bending). The variability in bending performance slightly favors the rectangle/circular design (5% vs. 9% variability). However, in torsion, the triangular shapes are much less variable than the rectangular/circular (2% vs. 13%). Showing that in torsional resistance, the triangular shapes inter-nest much better (see FIG. 34).

The shapes are also important in function. The long triangular shapes hold a vertical posture better in a less hardened, more flexible (non-composite) state, therefore will be better for insertion into long straight bones such as the humerus, tibia or femur. The rectangular shapes bend better around curves in bones such as the clavical without buckling.

Example 69

The value of the braided reinforcement construct is further demonstrated when compared to uni-axial constructs. Uni-axial constructs were made with the same fibers using the same methods as those in Example 67 in similar fiber volumes (45% FV vs. 49.4% FV—triangular constructs and 47% FV for circular constructs). The performance in bending was better than the braids (all fibers are axially oriented), however the results had significantly higher variability (17% compared to 5 or 9%) and took much longer to fill with resin and had spots within the construct that were not completely wet-out after hours of filling. In torsion, the uni-axial composite variability was similar (7% compared to 2%, triangular constructs or 13% circular constructs) but the performance was 29% lower than the braided constructs. This performance is expected is expected since the braided constructs (both circular and triangular) have 50% of the fiber volume contributing 50% of its strength (45° bias angles) to non-axial forces. This is an example of reduced filling variability using braided constructs due to the engineering in of hydrostatic force inducing elements that pull matrix through the full construct. It also demonstrates the advantage of being able to variably assign reinforcement to different directions of support. In addition, the constructs are simple, loadable structures, wherein uni-axial constructs would be very difficult to load without significant coating (that would reduce wet-out and/or fiber volume) to stiffen the components.

Example 70

Figure 35:
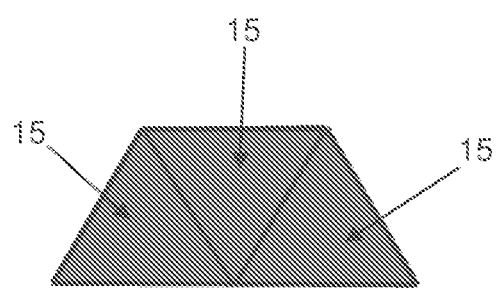
FIG. 35 shows still other composite implant configurations.

An example is depicted in FIG. 35 of how multiple triangular reinforcement shapes such as those depicted in Example 68 can be combined, in pre-cured or thermoplastic molding processes, to create pins of different shapes as well. Three of the triangular reinforcement constructs from Example 68 can be combined to create a well nested final implant of unique shapes

Example 71

Figure 36:
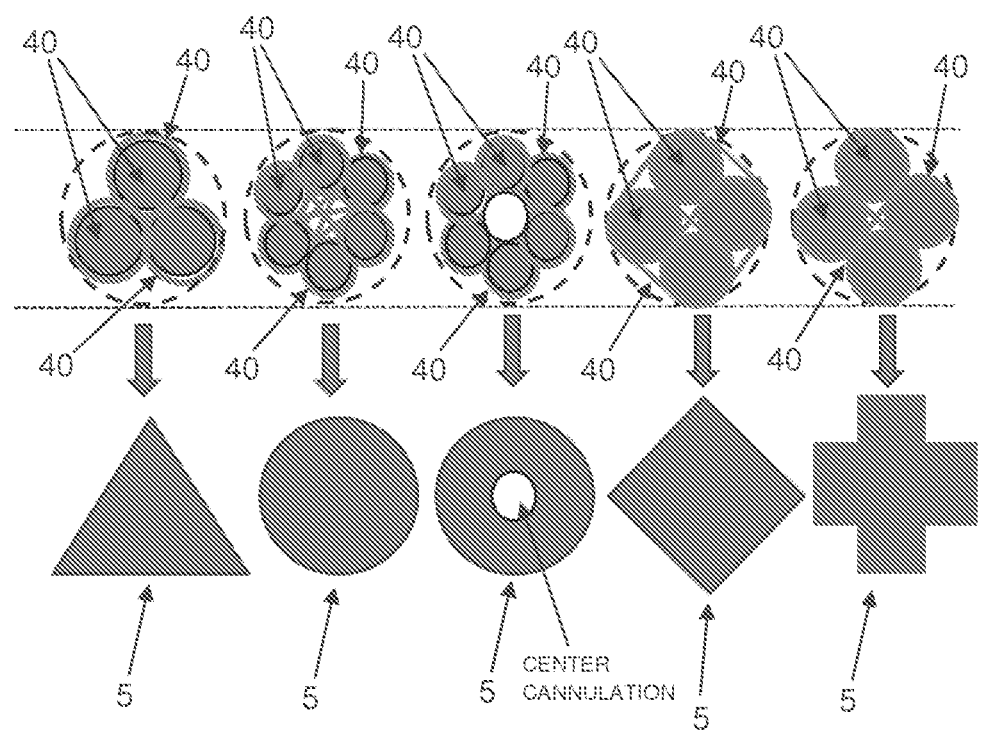
FIG. 36 shows additional composite implant configurations.

FIG. 36 shows how the number, size and orientation of axial fibers could be combined within a thermoplastic, reaction injection molding, or pultrusion/extrusion technique to form different shapes including long continuous shapes and a canulated form for direct implants or as part of the in situ curing method described within this invention. The forms presented in Example 68 are readily applicable to some of the shapes shown in FIG. 36.

Example 72

Figure 37:
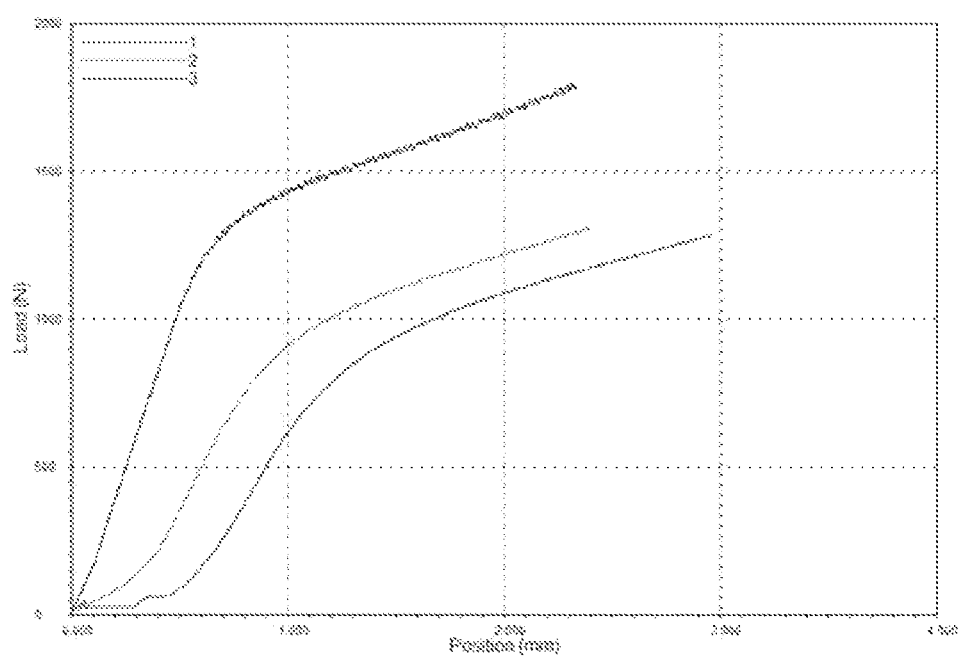
FIG. 37 shows load versus position for various composite implants.

PCL/PLA copolymer thermoplastic (Capa 8502A) was compounded with biodegradable glass (Mo-Sci Corp GL0122P/-53) and assessed for mechanical properties. Biodegradable glass was blended into thermoplastic at 5% glass volume and 25% glass volumes. Blends were molded into cubes (roughly 1 cm×1 cm×1 cm) and tested for compressive modulus. 5% glass volume cubes resulted in a 10% improvement in elastic modulus as compared to control cube of thermoplastic without glass. 25% glass volume cube resulted in a 68% improvement in elastic modulus as compared to control cube of thermoplastic without glass. The results are shown in FIG. 37.

Example 73

An FEA model was created to judge the requirements of an intra-medullar splint. The model was loaded with a 300N force at the proximal end of the bone (shoulder joint) and kept locked at the distal (elbow) end. The whole bone displacement at the proximal end of the bone was measured under unbroken, a partial proximal humeral fracture (a model of a fracture half-way through the bone) and while splinted with an intra-medullar splint with increasing step values of Young's modulus in the partial and full fracture bone. The results demonstrated that a splint with a Young's modulus of greater than 12 GPa was necessary to return the bone to its unbroken performance level.

Example 74

A bone break model was created with a composite tube (Garulite) with an 8.10 mm ID to empirically support the FEA model from Example 73. Nine 75 mm long flexible braided glass reinforcement rods as described in Examples 41-50 (between 30-40% FV) were loaded into a 10 mm diameter PET balloon through a tube that could only accept the rods one at a time. The bag and rods were positioned across an incomplete cut in the tube (approximately 0.7 mm in distance) and filled under vacuum from a single manually extended 60 cc syringe with the polyurethane from Example 51 then cured at 70° C. The tube break was tested pre and post splint positioning in non-destructive and destructive 4 point bend testing. In non-destructive testing, the load needed to cause strain at the fracture line of 0.5% increased from 28 N to 260 N. In destructive testing, the repair withstood 516 N prior to reaching 2% strain and yielded at about 3.5% strain at 800 N of loading with a peak load of 880 N and a non-catastrophic failure mode. Since bone typically breaks at 1.5-2% strain and will experience secondary bone healing between 2-10% strain, this example demonstrates that this invention, with a reasonable final fiber volume will increase the stiffness of a fractured tubular bone to a degree that it approaches the performance criteria of bone and will allow secondary healing to occur.

Example 75

Thermoplastic P4HB beads and PLA beads as received were mixed with phosphate based soluble glasses and incubated in phosphate based buffer solution at 50° C. for 52 days in vials, 50/50 by weight. Buffer was changed periodically as pH shifted. Beads were dried thoroughly after 52 days and analyzed via GPC. For P4HB, the higher molecular weight portion (Mz) decreased significantly regardless of additive. Lower molecular weight portion (Mn) increased slightly more in control than in samples with additives. Addition of 1 glass type effected on speed of degradation for both high molecular weight portion (Mz) as well as lower molecular weight portion (Mn) of samples. For PLA, there was a large decrease in MW regardless of additive. Soluble glass 1 very slightly slows degradation while soluble glass 2 speeds it up. This example demonstrates that a thermoplastic, soluble glass composite degrades. Additionally, P4HB—known to degrade primarily by enzymatic degradation—was demonstrated to have increased hydrolytic degradation due to the addition of soluble glass.

Example 76

Figure 38:
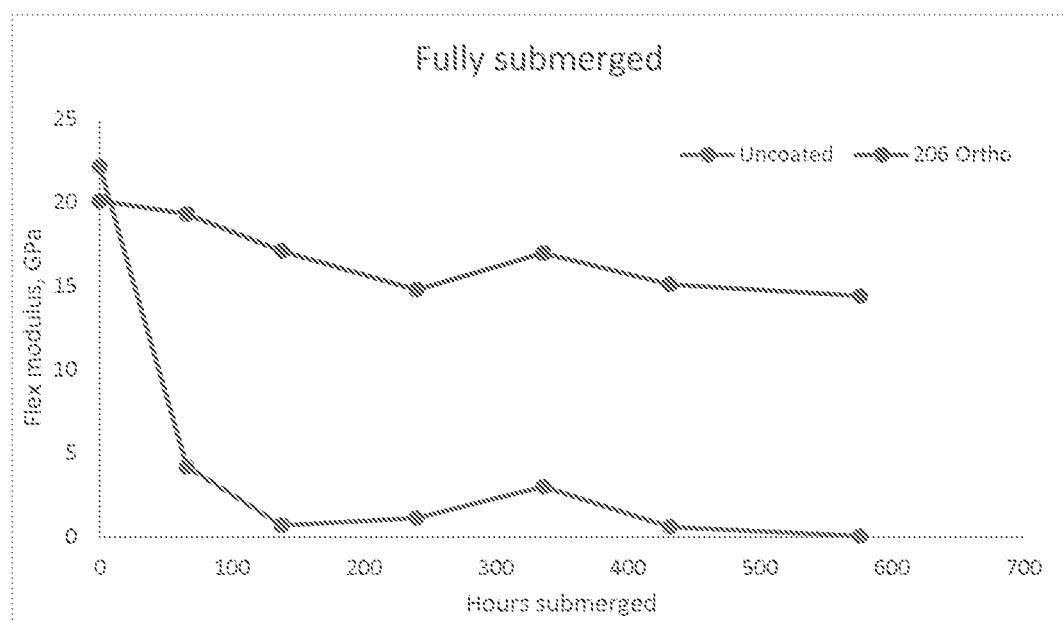
FIG. 38 shows flex modulus versus hours submerged for coated and uncoated containment bags.

2 mm pins were constructed as per Example 62 with the polyurethane of Example 51 and phosphate based soluble glass uni-axial fibers. The pins were coated with a well established material that retards the ingress of water to a rate of 1 gram*mil/(100 in$^2$)*day. The loss of stiffness was severely retarded over a 25 day period with a stiffness that remained well above the need expected in the FEA analysis from Example 73. This demonstrates that the use of an external barrier such as hydrophobic properties of the bag/balloon or an external coating on a pre-formed structure will serve to retard the degradation process of the full implant. See FIG. 38.

Example 77

Figure 39:
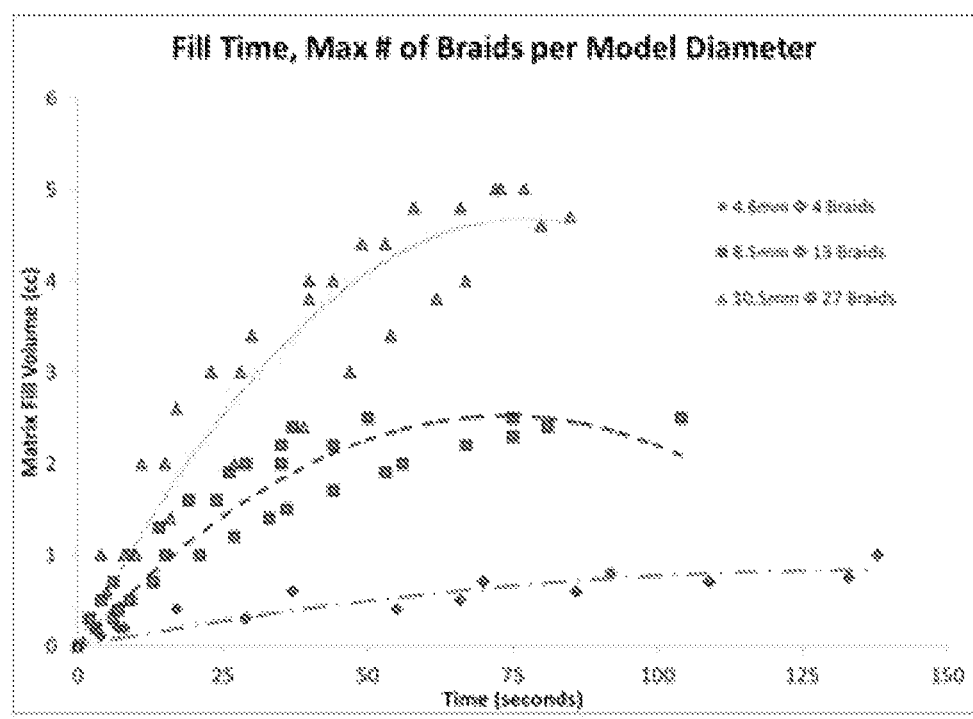
FIG. 39 shows matrix fill volume versus time for different composite implant constructions.
Figure 40:
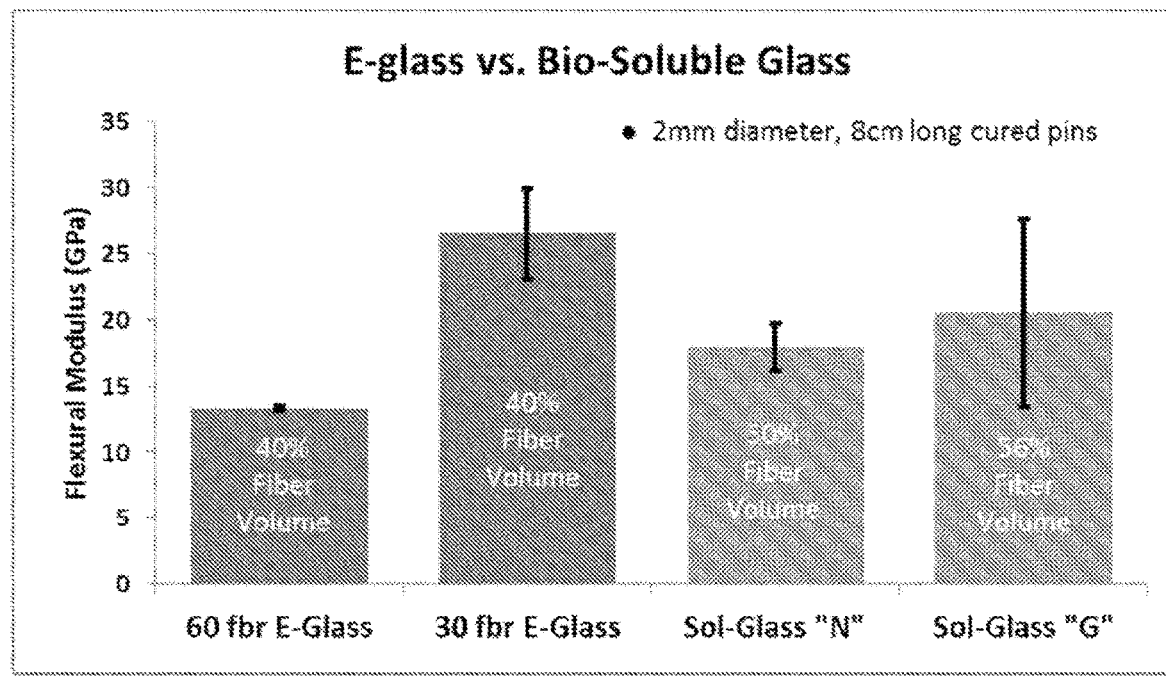
FIG. 40 is a graph showing the flexural modulus of various glass reinforcing elements.

The time it takes to fill a multi-braid structure was measured. A volumetric model was created with an increasing number of triangular braids (as per Examples 41-50) loaded horizontally. A polyurethane as per Example 51 (viscosity approximately 1000 cp) was filled under vacuum alone (no added positive mechanical pressure from the injection syringe) provided by a fully extended 60 cc syringe. The injection time was tracked along with the volume injected. The results are shown below (the fit lines are for visualization only, not a mathematical fit) for the highest fiber volume (# of braids) loaded per model size (described by model diameter). The models all had different overall volumes to fill but the same length (i.e., distance from bottom of model to top; the two largest models had approximately 61% fiber volumes to wet-out and the smallest model was a slightly higher fiber volume of 68% to fill. The fill and wet-out was completed in 90 seconds or less for the two largest volumes and took about 2 minutes for an "over-stuffed" small model. This demonstrates a reasonable fill time for in situ filling in an operative environment for building a splint. There were occasions when the reinforcing rods were too close to the inflow of the resin, this represents instances where the rod insertion could have kinked or blocked the inflow channels. These instances severely retarded inflow and reinforce the importance of relatively robust (but flexible) reinforcement rods. It also highlights the importance and addition of vacuum alone, from a simple disposable device (e.g., a syringe). See FIG. 39.

Example 78

Figure 41:
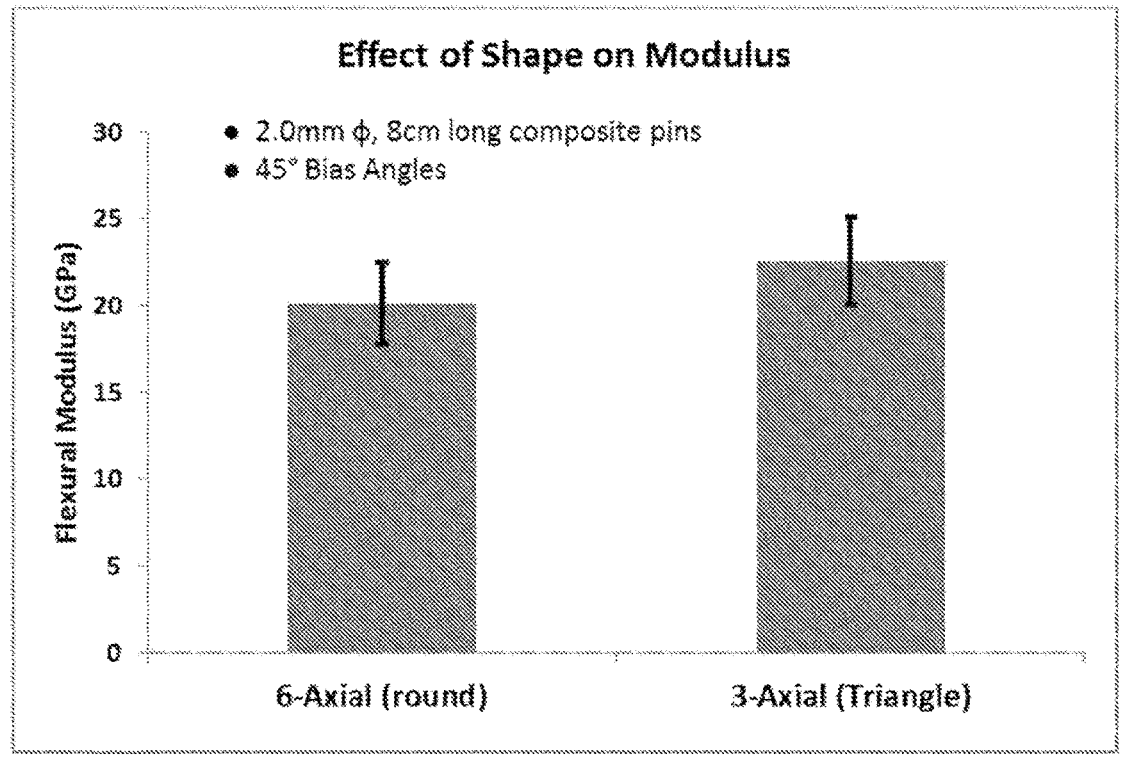
FIG. 41 is a graph showing the flexural modulus for various configurations of reinforcing elements.

Textile E glass braids were prepared having either 6 axial fiber bundles (predominantly circular cross-section) or 3 axial fiber bundles (predominantly circular cross-section) bound by bias fiber bundles orientated at +/−45° to the axial bundles in a glass content ratio of approximately 1:1 axial to bias fiber volume and designed to contain the same volume of fiber per unit length. 2 mm composite pins were built using the same polyurethane matrix and method of construction described in Examples 41-50. The flexural modulus of each are compared in FIG. 41 demonstrating no significant difference. Thus, the shape of a single reinforcing element will not alter its ability to reinforce a matrix.

Example 79

Figure 42:
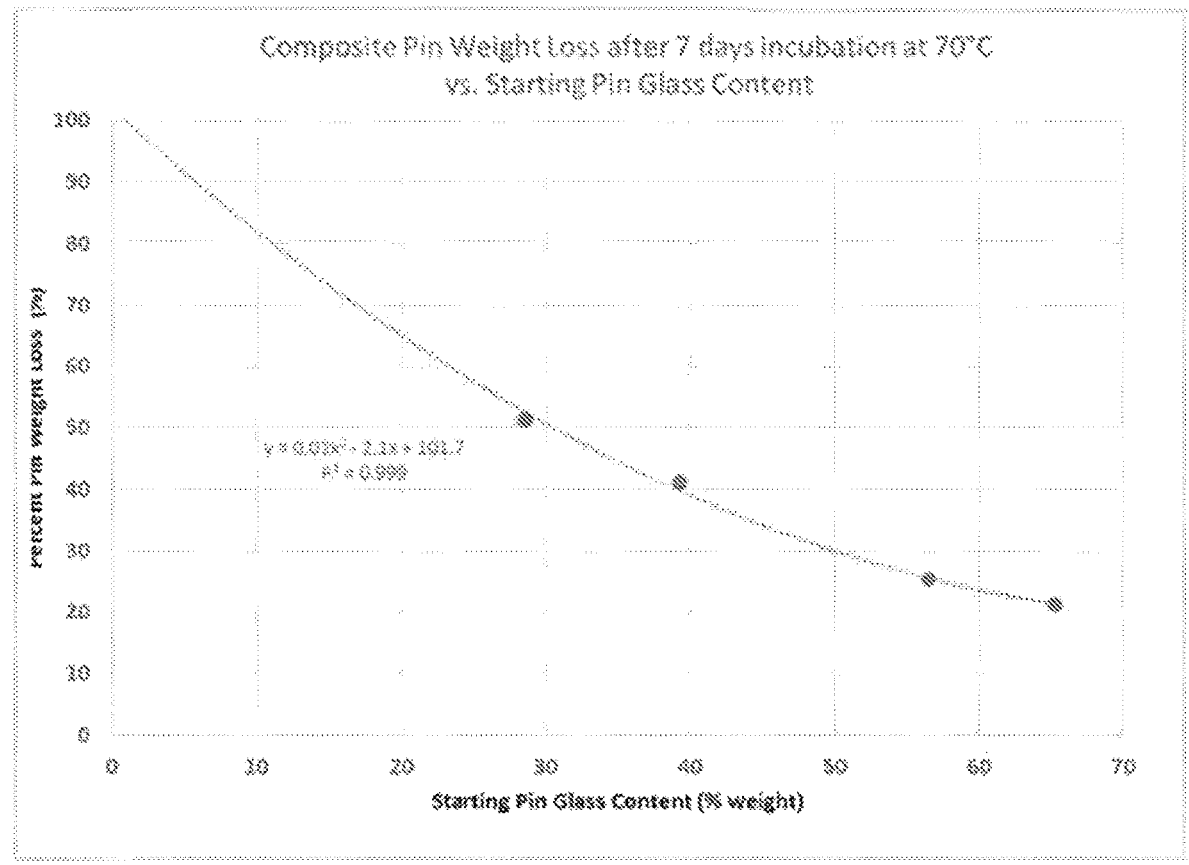
FIG. 42 is a graph showing composite pin weight loss versus starting pin glass content.

Polyurethane matrix was combined with phosphate based soluble glass fibers to produce material pins as per Example 62. The pins were degraded in a buffer solution at 70° C. to accelerate degradation effects. The remaining weight compared to the starting level of soluble glass material was found to correlate with the degradation rate in a non-linear fashion as shown in FIG. 42, thus demonstrating control of degradation rate of the product.

Example 80

Figure 43:
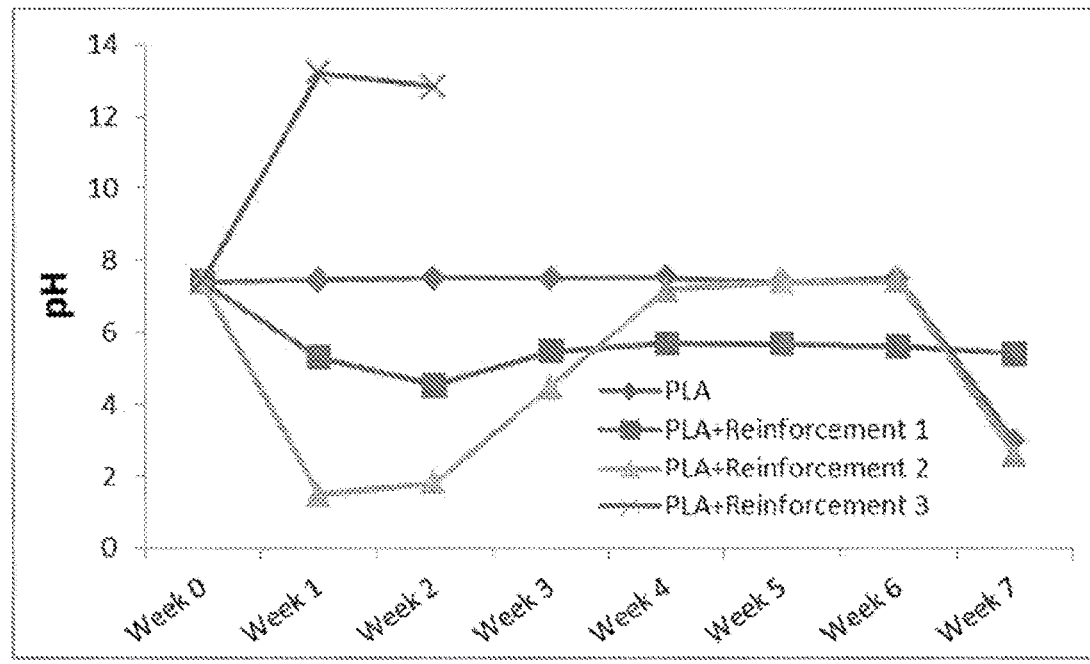
FIG. 43 is a graph showing pH versus time for various composite structures.

Thermoplastic PLA polymer was co-mingled with different types of phosphate based soluble glass fibers and submerged in a 7.4 pH buffer solution with periodic refreshes of the solution. FIG. 43 shows the resulting change in local environmental pH between PLA alone and PLA comingled with 2 different types of soluble glass fibers, each giving a different resulting environment.

Example 81

Figure 44:
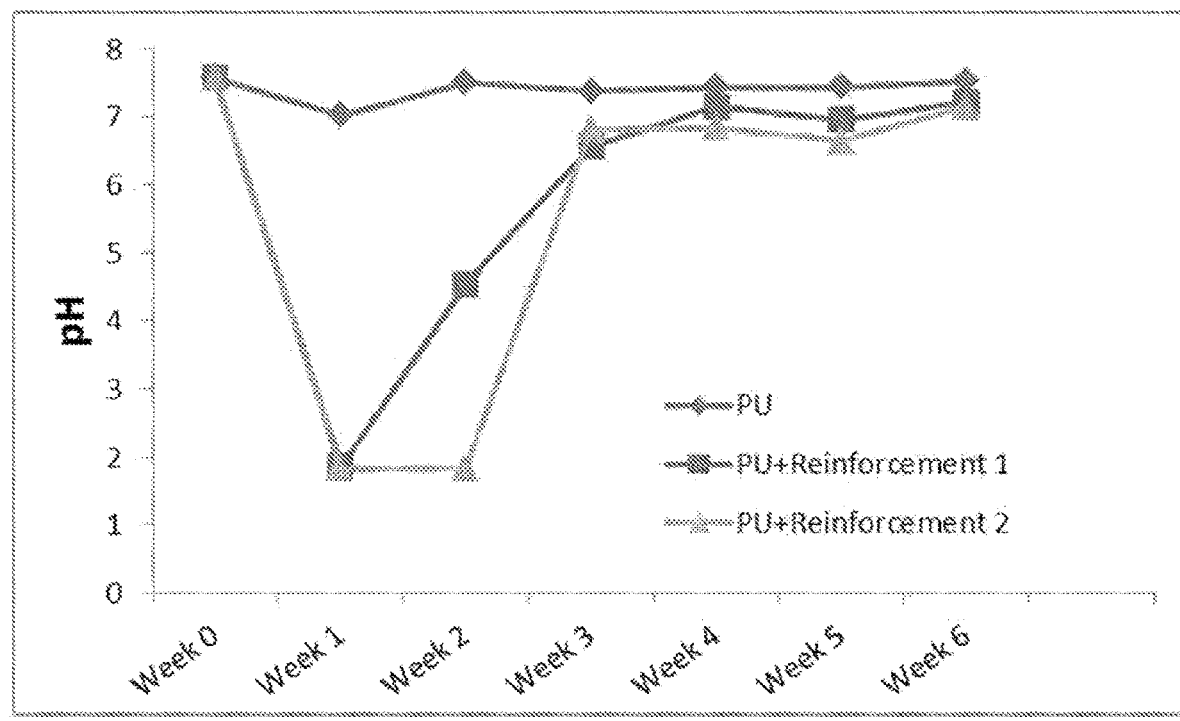
FIG. 44 is a graph showing pH versus time for other composite structures.

Thermoplastic Polyurethane polymer was co-mingled with different types of phosphate based soluble glass fibers and submerged in a 7.4 pH buffer solution with periodic refreshes of the solution. FIG. 44 shows the resulting change in local environmental pH between PLA alone and PLA comingled with 2 different types of soluble glass fibers, each giving a different resulting environment. Thus demonstrating the ability to modify the local environment during or after material degradation.

Example 82

Figure 45:
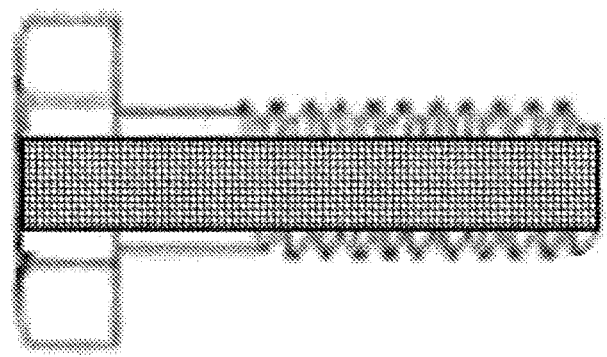
FIG. 45 is a schematic view showing a composite structure in the form of a screw.

The novel composite structure can be used to form various biodegradable devices, e.g., the biodegradable screw shown in FIG. 45. In this form of the invention, a mold, having a cavity which is the shape of a screw, is filled with the matrix material and the reinforcing elements, e.g., by positioning the reinforcing elements (e.g., woven fibers) in the mold cavity and flowing the matrix material around the reinforcing elements. Then the composite structure is cured in the mold and removed as a formed article ready for use. Alternatively, the reinforcing elements (e.g., nanoscale fibers) may be mixed with the flowable matrix material and the mixture flowed into the mold cavity for molding and curing.

Example 83

In another example, the novel structure can be used to form a biodegradable syringe. More particularly, and looking now at FIG. 46, there is shown a syringe system comprising a reservoir of known, well metered volume having a distal injection end and an open end accepting a plunger, contiguously tipped with a low modulus material capable of forming a movable hydrostatic seal with the sides of the reservoir and the plunger having a length enabling single handed actuation. The distal end of the reservoir forms a nozzle that enables a range of injection fluid viscosities and providing a needle sharp enough to penetrate dermus and musculature and strong enough to resist breakage with reasonable use.

Each of the components described above can be constructed of various composites that are created from at least one reinforcing element embedded within a matrix. In a preferred embodiment of the invention, the syringe reservoir is created with a biodegradable thermoplastic material embedded with soluble glass particulate and imparted with hydrophobicity on the internal surface. The hydrophobic surface allows for the storage of pre-filled injectable material for a predictable time frame. The soluble glass has an autocatalytic water initiated relationship with the thermoplastic such that a cascading change in pH accelerates biodegradation in a composting environment.

Figure 46:
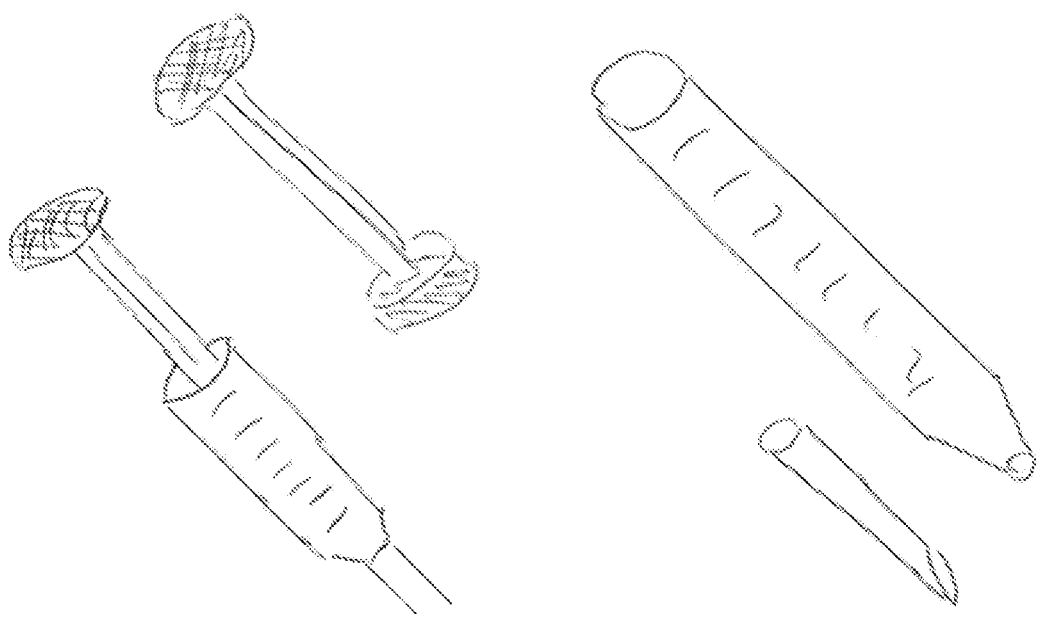
FIG. 46 is a schematic view showing a syringe formed out of a composite structure.

In a preferred embodiment, and referring to FIG. 46, the plunger is constructed of two different parts, one part is a thermoplastic material as described above. The other part is a thermoset or thermoplastic of similar design but having a functional modulus much closer to that of rubber. Soluble glass particulate completes the composite given an autocatalytic water initiated relationship with the thermoplastic such that a cascading change in pH accelerates biodegradation in a composting environment.

Figure 47:
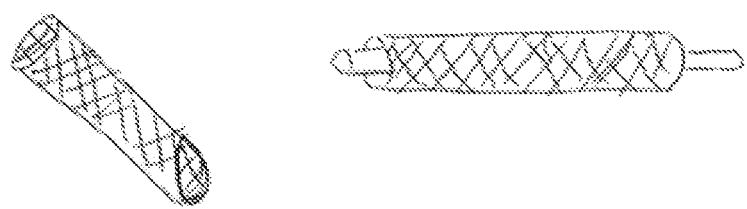
FIG. 47 is a schematic view showing a reinforcing element which may be used in the composite structure forming a syringe.

In a preferred embodiment of this invention, and referring to FIGS. 46 and 2, the needle is of separate construction with a fitted proximal end or with the capability to be attached to the reservoir via adhesion, energy induced welding (RF welding or the like), or some other such means. The needle is constructed of a thermoset or thermoplastic encased circular braid of a high modulus reinforcing element such as soluble glass, FIG. 47. The reinforcing element serves to enhance the needle(s) resistance to axial and bending forces and acts as a biodegradation initiator and/or auto-catalyzing agent enabling practicable composting.

Examples of Barriers Used in Biodegradable High Strength Composite Systems

Example 84

2 mm diameter round pins (5 cm) long were made out of a biodegradable composite like example 62 in Ortho040506. One group of pins was coated with a non-degradable well established and measurable (WVP–1 g*mil/100 in$^2$ day=0.4 g*mm/m$^2$ day)) substance to a thickness of 0.5 mil (13 µm), a control group remained uncoated. The groups of pins were submerged in distilled water at room temperature (20° C.). The loss of mechanical properties (bending stiffness) was measured periodically. The rate of stiffness loss was reduced from 16% per day to 1.1% per day with the coating.

Example 85-89

A fully degradable pin with dimension from above can be reduced to practice using a number of available barrier substances described in literature as listed in the table below (all at temperatures between 20 and 25° C.):

| Example | Material | WVP (g mm/m$^2$* day) | Req Thickness (µm) | Ref |
|---|---|---|---|---|
| 85 | 20 µm thick commercial Poly (Lactic Acid) Film | 1.1 | 44 | [1] |
| 86 | Al$_2$O$_3$ Coated PLA film | 0.7 | 21 | [1] |
| 87 | Poly Hydroxybuterate-co-valerate (6% valerate) | 0.3 | 11 | [2] |
| 88 | Poly (Lactic Acid) 66% Crystallinity | 2.1 | 66 | [2] |
| 89 | Poly ε-capralactone | 4.4 | 143 | [2] |

This table shows that results similar to that above can be achieved with substances considered biodegradable or bio-absorbable with a single barrier layer between 0.8 and 11 times the thickness of the material in example 1 above.

Example 90-93

For the examples above, the temperatures studied were approximately 20-25° C. If the pin were to be designed for use inside of a body, as a small bone splint for example, then the temperature would be 37° C., resulting in more rapid diffusion of water (Brownian motion). A fully degradable pin with dimension from Example 1 above can still be reduced to practice with a variation of the thickness (calculated using an estimate of the Arrhenius equation):

| Example | Material | WVP (g mm/m$^2$* day) | Req Thickness (µm) | Ref |
|---|---|---|---|---|
| 90 | 20 µm thick commercial Poly (Lactic Acid) Film | 3.0 | 96 | calculated |
| 91 | Poly Hydroxybuterate-co-valerate (6% valerate) | 0.8 | 25 | |
| 92 | Poly (Lactic Acid) 66% Crystallinity | 4.9 | 159 | |
| 93 | Poly ε-capralactone (PCL) | 10.6 | 343 | |

This table shows that results similar to Example 84 can be achieved with substances considered biodegradable or bio-absorbable with a single barrier layer between 2 and 27 times the thickness of the material in Example 84 above.

Example 94

The thicknesses of the coatings in Examples 90-93 are high for some of the more readily available and acceptable materials for human implantation. In addition there may be a desire to exact a compliant device, such as an implantable medical balloon. Therefore, the thickness of the barrier would need to stay within the range of a compliant material. To exact this, an insoluble solid suspension is added to the polymer to reduce the permeability rate. It has been reported that amounts as small as 5 wt % of clay added to polymer can halve the permeability [3]. In the same publication, the effect on permeability rises exponentially for up to 20 wt % of additive. To reduce this to practice, the PCL from Example 93 above is compounded with 10 wt % biocompatible insoluble such as Mg(OH)$_2$— which has a plate-like morphology after undergoing a specific heating profile. Mg(OH)$_2$ is estimated to be half as effective as clays, therefore the effect is to reduce the WVP of the material from 10.6 to 5.3 g mm/m$^2$*day. With this material the required barrier thickness is reduced from 343 to 171 µm (≈0.006"). Given the inherent flexibility of PCL, this is a good thickness for a compliant human implantable degradable balloon.

Example 95

An alternate example (to Example 109) of a barrier appropriate for use as a compliant human implantable degradable balloon is enacted by the use of multiple co-extruded layers of polymers. The calculated WVTR of the resulting films of examples 1-4 is 31 g/m$^2$*day. To enact a thinner design with biologic benefits layers of a balloon can be created by co-extrusion of a tube and subsequent expansion using balloon forming methods. Other methods such as dip coating can also be used. The resulting WVTR is calculated using a parallel network equation. [4]

| Layer | Material | WVP (g mm/m²* day) | Thickness (μm) | WVTR (g/m²* day) |
|---|---|---|---|---|
| Out | Poly (Lactic Acid) 66% Crystallinity/ Hydroxyapatite Suspension | 4.9 | 25.4 | 193 |
| Middle | Poly ε-capralactone (PCL)/ Mg (OH)₂ 10 wt % suspension | 5.3* | 25.4 | 209 |
| Inside | Poly (Lactic Acid) 66% Crystallinity/ Mg (OH)₂ 10 wt % suspension | 2.5* | 50.8 | 48 |
| *Estimated halved WVP due to insoluble components at 10 wt % | | | 100 | 33 |

This example shows that by layering three dissimilar materials with different water transfer rates, a barrier with similar water permeability as those of examples 1 through 4 (33 g/m²*day vs. 31 g/m²*day) with a relatively thin material (100 μm, 0.004"). In addition, the material has an outer coating infused with Hydroxyapatite which is advantageous if implanted near bone, and the compliance and adhesive capability of the middle layer of PCL gives some resilience to the overall structure.

REFERENCES FOR EXAMPLES 84-95

[1] T. Hirvikorpi, M. Vähä-Nissi, A. Harlin, M. Salomäki, S. Areva, J. T. Korhonen, and M. Karppinen, "Enhanced water vapor barrier properties for biopolymer films by polyelectrolyte multilayer and atomic layer deposited Al2O3 double-coating," *Appl. Surf Sci.*, vol. 257, no. 22, pp. 9451-9454, September 2011.
[2] R. Shogren, "Water vapor permeability of biodegradable polymers," *J. Environ. Polym. Degrad.*, vol. 5, no. 2, pp. 91-95, 1997.
[3] J.-W. Rhim, H.-M. Park, and C.-S. Ha, "Bio-nanocomposites for food packaging applications," *Prog. Polym. Sci.*, vol. 38, no. 10-11, pp. 1629-1652, October 2013.
[4] K. Cooksey, "Interaction of food and packaging contents," *Intell. Act. Packag. Fruits Veg.*, pp. 201-237, 2007.

Example 96

A two component polyurethane matrix material was made by preparing (component A) polyol blend consisting of a polycaprolactone triol (70% by weight), 1,4;3,6-dianhydrous-d-sorbitol (15%), and a citric acid ester (15%). The polyol was mixed and crosslinked with a hexamethylene diisocyanate trimer (component B) to provide a polyurethane matrix that is used in the application to bind reinforcement fibers to ultimately form a composite. The isocyanate (NCO)/hydroxyl (OH) stoichiometry ratio was 1.1. Catalyst was added to polyisocyanate to catalyze the isocyananate-hydroxyl reaction which forms the polyurethane. Catalyst selection was based on compatibility and stability in the system. In these studies, a zirconium catalyst was added to the isocyanate prior to mixing the polyol and isocyanate components.

Viscosity.

Viscosity for this application is important for the injection process of exiting the syringe, flowing through a static mixer (to mix components A and B), through the catheter, into the implant enclosure which contains reinforcing fibers. Proper viscosity is also critical such that the reinforcing fibers become completely "wet out" by polyurethane before gelling begins. centipoise, respectively. Similar viscosities of components A and B is critical to provide efficient and thorough mixing of the 2 components. The viscosity of the mixed components A and B one minute after mixing was 1440 cps.

Exotherm.

Proper curing of the polyol-isocyanate reaction to form the polyurethane described above causes an exotherm and results in development of critical mechanical properties. The reaction rate and the extent of exotherm can be controlled by altering amount of catalyst used, and by amount of reinforcement. Preparing a 5 gram sample of polyurethane with 0.17% zirconium catalyst resulted in a maximum temperature of 35° C. twenty four minutes after mixing. Increasing the zirconium catalyst level to 0.3% resulted in a maximum temperature of 53° C. twelve minutes after mixing. The final matrix glass transition temperature was 46° C. with each of catalyst levels tested.

With 30% volume fiber reinforcement and 70% polyurethane matrix, and 0.17% zirconium catalyst, the maximum temperature of 24° C. occurs over a time frame of 10 to 20 minutes after mixing. This composite composition with 0.3% catalyst causes a maximum temperature of 33° C. twelve minutes after mixing.

Pot Life.

As with exotherm, pot life can be controlled by varying amount of catalyst used in polyurethane. The polyurethane for this procedure has a usable working/application time (also known as potlife) in which it can be efficiently injected to wet out reinforcement fiber within the implant enclosure. An acceptable viscosity range has been observed to be roughly 500 cps-5000 cps. The useable working time (viscosity of mixed components A and B reaching 5000 cps) with 0.3% zirconium catalyst was six minutes. The working time of this same system with 0.2% zirconium catalyst was eleven minutes.

Mechanical Strength.

Mechanical strength development is very important for implant performance, as it determines when the patient can be moved out of the operating room, and when the patient can support him or herself. A composition containing 50% (by volume) of the above polyurethane with 0.2% zirconium catalyst and 50% by volume glass fibers was prepared into specimens for flexural modulus testing. After 6 days curing at 37° C. the flexural modulus was 12 GPa.

Example 97

A polymer matrix consisting of both caprolactone and lactic acid groups was formulated. Component A of the polymer matrix consisted of a poly(caprolactone) triol (70% by weight), poly(caprolactone-co-lactide) triol (10% by weight), 1,4;3,6-dianhydrous-d-sorbitol (15%), and a citric acid ester (5%), plus a bismuth catalyst (0.09% by weight). The polyol (component A) was mixed and crosslinked with a hexamethylene diisocyanate trimer (component B) to provide a polyurethane matrix that is used in the application to bind reinforcement fibers so as to, ultimately, form a composite implant. The isocyanate (NCO)/hydroxyl (OH) stoichiometry ratio was 1.1. Viscosity of components A and B were 1210 and 1066 cPs, respectively. The pot life of the formulation is around 4 minutes. The maximum temperature reached is 65° C.; however, in the presence of 40% fiber volume, the maximum temperature reached is 45° C.

Example 98

Round pre-cured pins for intramedullary (IM) bone fixation with a 2 mm diameter and 3 cm long, were made out of a biodegradable composite, consisting of glass braid reinforcement, a polymer matrix, and an outer barrier. The glass braids were made out phosphate glass fibers with 3 axial fiber bundles (predominantly circular cross-section) bound by bias fiber bundles orientated at +1-45° to the axial bundles. Component A of the polymer matrix consisted of a poly(caprolactone-lactic acid) triol (80% by weight), 1,4;3,6-dianhydrous-d-sorbitol (15%), and a citric acid ester (5%), plus a tin catalyst (0.13% by weight). The polyol was mixed and crosslinked with a hexamethylene diisocyanate trimer (component B), mixed with 15% hydroxyapatite, to provide a polyurethane matrix that is used in the application to bind reinforcement fibers to, ultimately, form a composite implant. The isocyanate (NCO)/hydroxyl (OH) stoichiometry ratio was 1.1. Hydroxyapatite is added to the polymer matrix as it is biocompatible, osteoinductive, and acts as degradation control buffer. The two parts (components A and B) are mixed in a ratio of 1:2, and reacted with the glass reinforcement (55% fiber volume) with the help of a tin catalyst at a concentration of 0.13%, and cured at 70° C. overnight. The cured rods are coated with a 100 micron thick layer (i.e., a coating) that consists of an inner barrier layer and an outer compatibilizer layer. The inner barrier layer is a 75 micron thick water barrier layer, and consists of high aspect ratio magnesium hydroxide microparticles (average size 10 micron diameter and 200 nm thick), dispersed in a degradable polyester polyurethane matrix. The outer compatibilizer layer consists of beta tricalcium phosphate, dispersed in a degradable polyester polyurethane matrix. To increase the adhesion of the coating to the pins, the pins are slightly roughened/structured. The coating has a water vapor permeability (WVP) of 2 g*mil/100 in$^2$ day (0.8 g*mm/m$^2$ day). Where the pins are used for hammer toe fixation, the cured pins are cut to the desired size, typically ranging from 2-3 cm. Similarly-formed pins, of appropriate size, can be used for other types of IM fixations, including small bones, clavicle, ribs, radius, ulna, etc.

Example 99

Pins are formed as in Example 98, except that one or both the ends of the pins are tapped and/or barbed for securing the pins to bone.

Example 100

This example is for pre-cured rods for fixation of tibia, femur, and humerus. Round rods with 12.5 mm diameter, and 30 cm long, were made out of a biodegradable composite, consisting of glass braid reinforcement, a polymer matrix, and an outer barrier. The glass braids were made out phosphate glass 6 axial fiber bundles (predominantly circular cross-section) bound by bias fiber bundles orientated at +/−45° to the axial bundles. The polymer matrix was a poly(caprolactone-co-lactic-co-glycolide) polyurethane system, and consisted of a mixture of two parts. The first part (Part A) consists of a polyester polyol mixture with a catalyst, whereas the second part (Part B) consists of isocyanate prepolymer with 25% beta tricalciumphosphate, which is biocompatible, osteoinductive, and acts as buffer control. The isocyanate (NCO)/hydroxyl (OH) stoichiometry ratio was 1.05. The two parts are mixed in a ratio of 1:2, and reacted with the glass reinforcement (50% fiber volume) with the help of a tin catalyst at a concentration of 0.07%, and cured at 70° C. overnight. The polyester groups in Part A impart degradability to the cured matrix, and consist of caprolactone, lactic acid, and glycolic acid groups. The cured rods are coated with a 50 micron thick vapor-deposited magnesium coating. To increase the adhesion of the barrier to the pins, the pins are slightly roughened/structured. This rod can then be used for tibia fixation (of femoral fixation, humeral fixation, etc.).

Example 101

This example discusses the splint system with a single pre-cured rod for intramedullary or other bone hole fixation. The diameter of the rod can be any diameter between 0.5 mm and 20 mm depending on the application. For some applications, the diameter of the rod can be between 1 mm and 7 mm. For some other applications, the diameter of the rod can be between 6.5 mm and 14 mm. The length of the rod can be between 0.5 cm and 46 cm depending on the application. For some applications, the length of the rod can be between 2 cm and 15 cm. For some other applications, the length of the rod can be between 12 cm and 30 cm. The rod is placed inside a deflated containment bag. The containment bag is then placed inside the intramedullary (IM) canal of the bone, or inside another bone hole, inflated to the dimensions of the IM canal (e.g., 12.5 mm diameter and 30 cm long) or inflated to the dimensions of another bone hole, and filled with two-part injectable matrix to occupy the remaining space. The pre-cured rod has the same composition as disclosed in Example 100 above, but without a barrier layer. The human implantable degradable containment bag is prepared by with multiple co-extruded layers of polymers, as discussed in Example 96 above. The calculated water vapor transfer rate (WVTR) of the resulting containment bag is 31 g/m$^2$*day. The two-part injectable matrix consists of Part A and Part B. Part A consists of poly(caprolactone-lactic acid) triol (80% by weight), 1,4;3,6-dianhydrous-d-sorbitol (15%), and a citric acid ester (5%). Part B is hexamethylene diisocyanate trimer, mixed with 20% biphasic calcium phosphate. Part A and Part B are then injected through a catheter into the inflated containment bag, and cured under physiological conditions. The resultant curing provides a solid composite implant that substantially conforms to the shape of the IM canal (or other bone hole). Such splint systems can be used for fixation of the tibia, clavicle, humerus, femur, radius, ulna, ribs, etc.

Example 102

This example discusses a splint system with multiple pre-cured pins (rods) for tibial fixation. Multiple pre-cured rods (10-12 in number) of diameter 2.2 mm and length of 28 mm are placed inside a deflated containment bag. The containment bag is then placed inside intramedullary (IM) canal of the tibia, inflated to the dimensions of the tibial IM canal (e.g., 12.5 mm diameter and 30 cm long), and filled with two-part injectable matrix to "glue" the pre-cured pins together and occupy the remaining space. The pre-cured pins consist of 65% phosphate glass reinforcement braids with remainder being a polymer matrix. The composition of the polymer matrix is similar to that disclosed in Example 97 above. The pot life of the two-part injectable matrix after mixing is 3 minutes, and reaches a maximum temperature of 45° C. during the cure. Such a composite implant requires a smaller access hole (e.g., approximately 2.5-3 mm).

Example 103

This example discusses a splint system with multiple pre-cured reinforcement braids (pins). Multiple reinforcement pins (10-12 in number) of diameter 2 mm and length of 28 mm are placed inside a deflated containment bag. The containment bag is then placed inside intramedullary (IM) canal of tibia (or other bone), inflated to the dimensions of the tibial IM canal (e.g., 12.5 mm diameter and 30 cm long), and filled with two-part injectable matrix to "glue" the pre-cured pins and occupy the remaining space. The composition of the polymer matrix is similar to that disclosed in Example 97 above. The pot life of the two-part injectable matrix after mixing is 3 minutes, and reaches a maximum temperature of 45° C. during the cure. Such an implant requires a smaller access hole (e.g., approximately 2.25-3 mm).

Example 104

This example describes a process for forming sheets for coating pre-cured pins and rods. Polycaprolactone (MW of 50,000) was dissolved in ethyl acetate solvent at a concentration of 25%. Particles of beta tricalciumphosphate was then added to the solution at a concentration of 5%. The solution was then thoroughly mixed to dissolve the polycaprolactone (PCL) and efficiently disperse the particles. Sheets were then drawn out of the solution using a drawdown technique, and then dried in an oven at 40° C. to remove all the solvent.

Example 105

This example discusses a pre-cured rod (pin). The rod consists of four elements: glass fibers as reinforcement, sizing on glass fibers, matrix, and a coating. The glass fibers are biodegradable phosphate glass fibers that release sodium and calcium ions as the fibers degrade. A sizing of polyvinylalcohol was applied to the glass fibers for improved wettability of the polymer matrix. Component A of the polymer matrix consisted of a poly(caprolactone) triol (70% by weight), 1,4;3,6-dianhydrous-d-sorbitol (15%), and a citric acid ester (15%), plus a zirconium catalyst (0.3% by weight). The polyol (component A) was mixed and cross-linked with a hexamethylene diisocyanate trimer (component B) and 5% beta tricalciumphosphate, to provide a polyurethane matrix that is used in the application to bind reinforcement fibers so as to, ultimately, form a composite implant. The isocyanate (NCO)/hydroxyl (OH) stoichiometry ratio was 1.1. Hydroxyapatite is added to the polymer matrix as it is biocompatible, osteoinductive, and acts as degradation control buffer. The two parts are reacted with the glass reinforcement (30% fiber volume) with the help of a tin catalyst at a concentration of 0.07%, and cured at 70° C. overnight. After the rods are cured, a coating is applied in two stages. In the first stage the rods were dip-coated in a solution of 18% polylactic acid and 2% magnesium hydroxide in ethyl acetate. The solvent was allowed to completely evaporate by placing them in a 70° C. oven for 1 hour. In the second stage, these rods were then coated with a sheet of polycaprolactone with beta tricalcium phosphate as disclosed in Example 104 above.

Example 106

In this example, a process for making degradable screws is described. A mold, having a cavity which is the shape of a screw, is made by drilling and tapping a Teflon block. Reinforcing glass braid is then inserted through the center of the screw-shaped cavity, followed by filling the cavity with a two-part curable polymer matrix as described in Example 97 above. The matrix is cured, followed by removal of the screw from the mold. An aluminum or stainless steel mold can also be used for improved feature resolution. The matrix formulation can, optionally, contain 10% hydroxyapatite particles as an osteoinductive substance.

Example 107

The selection of a catalyst (see Examples 97-106 above) is dependent on multiple factors, for example, pot life, exotherm properties, mechanical properties, as well as potential foaming in case the injectable polymer matrix comes in contact with water.

| | | | Max Temp During Cure (Celsius) | | |
| --- | --- | --- | --- | --- | --- |
| | | Pot Life | Pure Polymer Matrix | With 30% Fiber | Foaming in Cured Matrix in Presence of Water |
| Tin | 0.05 | >30 min | 38 | 27 | Excessive Foaming |
| | 0.09 | 12 min | 57 | 31 | Excessive Foaming |
| | 0.13 | 3.5 min | 68 | 48 | Excessive Foaming |
| | 0.2 | <1 min | >85 | 77 | Some Foaming |
| Bismuth | 0.05 | >30 min | 32 | 25 | Some Foaming |
| | 0.09 | 20 min | 54 | 31 | Some Foaming |
| | 0.13 | 4 min | 62 | 44 | Minimal/No Foaming |
| | 0.2 | <1 min | >85 | 65 | Minimal/No Foaming |
| Zirconium | 0.05 | >30 min | 21 | 21 | Does not Cure |
| | 0.09 | >30 min | 21 | 21 | Does not Cure |
| | 0.13 | >30 min | 25 | 22 | Some Foaming |
| | 0.2 | 25 min | 31 | 25 | Some Foaming |
| | 0.3 | 6 min | 43 | 35 | Some Foaming |

Example 108

Another important criteria is the hydroxyl content in the polyol part (the aforementioned component A) of the formulation. If the hydroxyl content is too low, the matrix may not cure, or may have lower mechanical properties. On the other hand, if the hydroxyl content is high, the implant can heat up significantly due to the heat generated during the crosslinking reaction. It is important for the hydroxyl content to be in the correct range to achieve the desired cure profile, exotherm properties, mechanical properties and Tg of the cured implant. For example, in a particular set of reactions for degradable polyester, the heat of reaction is 1.4 kcal/gram of hydroxyl groups. With hydroxyl content of 14% in the polyol component, there is a total heat release of 200 cal/g of the polyol component, which provides a maximum temperature of 44° C., and pot life of 4 minutes. However, with a hydroxyl content of 0.5% in the polyol component, we get a total heat release of 6.8 cal/g of the polyol component, which is generally not sufficient to cure the composite implant.

Example 110

As another example of layering materials for a desired goal, a biodegradable polymer, e.g., polycaprolactone (PCL), was wire coated over glass fibers to form a 2 mm diameter cord. The combination yields a useful cord with stiffness properties that can be used for a variety of applications such as parachute cords, fishing nets, etc. The glass fibers, when composed of a soluble glass and exposed to enough water, will change the micro-environment of the fiber and rapidly cause the degradation of the whole biocomposite leaving environmentally-neutral remains. This could be combined with a rapidly soluble glass and material that degrades by primarily enzymatic mechanisms such as with the poly-4-hydroxybutyrate (P4HB) above to create a cord that biodegrades in an very short time period.

Example 111

Specific to this example, PHAs like P4HB rely on enzymes for degradation. The ability to encourage nonenzymatic degradation will likely accelerate the combined rate of degradation and/or allow for degradation in environments free from biologic activity. Enzymatic degradation, a consumption process, is initiated from the surface inwards and therefore depends on a large surface area-to-mass ratio (such as films) in order to be classified as a biodegradable material according to ISO and ASTM standards. The application of the present invention allows simultaneous enzymatic degradation to occur in an outside-in manner, while the enzyme additive initiates and encourages degradation mechanisms within the center of the thicker materials. This will expand the range of materials that can be
classified as biodegradable under ASTM standards, in addition the solubilized filler (glass fiber) will increase the porosity of the material to allow enzymatic degradation throughout the material by increasing the surface area of the material. As a further expansion of this concept, some of the enzyme additives can be produced in a fiber form and used, with appropriate compatibalizers, to increase the mechanical properties (e.g., strength and stiffness) of the material, thereby increasing the utility of the material to higher load-bearing applications while still maintaining a biodegradable classification. The high performance polymers used for engineering applications are highly cross-linked to obtain the mechanical properties desired. These materials are not readily biodegradable in ambient conditions, if biodegradable at all in any relevant conditions. The [resent invention will allow biodegradable polymers to be used for higher performance applications. Currently, biopolymers such as those disclosed above (e.g., PH4B, PLA, etc.) are blended with polysaccharides to increase the degradation rate. The polysaccharides tend to be sticky and difficult to work with, and have relatively poor mechanical properties. The mechanics of fiber-loaded composites are well known in the industry.

Example 112

Another example is the stiffening of a polymer with the addition of an additive (bioglass). In this case, a very low molecular weight polymer, one that can be heated to a low temperature and kneaded by hand with off-the-shelf bioglass (e.g., silicate-based soluble glass), is used. The bioglass additive was used to significantly increase the stiffness of the material, in addition, once dissolving, the bioglass will cause an internal shift to a basic environment, increasing the degradation rate. Given that the polymer is already at a low molecular weight, the time it takes to reach a 10,000 cp level for enzymes to complete the degradation process is much lower and makes this a very rapidly degrading material.

Example 113

Another example is a flexible composite (e.g., in the form of a rope, cord, sheet, mesh, tube, etc.) fabricated with the reinforcement fibers or braids along with a degradable polymer matrix. These flexible composites (e.g., in the form of a rope, cord, sheet, mesh, tube, etc.) have a bending modulus of preferably less than 5 GPa, preferably less than 3 GPa, and more preferably less than 1 GPa. The tensile modulus of the ropes, cords, sheets, meshes, tubes, etc. is preferably less than 200 GPa, preferably less than 150 GPa, and more preferably less than 100 GPa. Also, the tensile modulus of the flexible rope, cord, sheet, mesh, tube, etc. is at least 1 GPa, preferably at least 5 GPa, and more preferably at least 10 GPa.

MODIFICATIONS OF THE PREFERRED EMBODIMENTS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:
1. A composite comprising:
   a layered structure, configured to selectively pass water, the layered structure comprising:
   (a) a core structure, the core structure comprising:
      (i) at least one reinforcement element, the at least one reinforcement element comprising:
         (1) a reinforcement element core structure comprising a degradable matrix and at least one filament, wherein the at least one filament is disposed within the degradable matrix; and
         (2) an outer region formed on the reinforcement element core structure, wherein the outer region of the reinforcement element core structure comprises at least one layer; and
   (b) an outer region formed on the core structure, wherein the outer region of the core structure comprises at least one layer, wherein the at least one filament comprises between 5% and 85% by volume of the reinforcement element.

2. The composite according to claim 1, wherein the degradable matrix comprises biodegradable or bioabsorbable materials selected from the group consisting of polylactic acid homopolymer or copolymer, polycaprolactone, polyglycolide (PGA), glycolide copolymers, glycolide/lactide copolymers (PGA/PLA), polylactic acid cocaprolactone block copolymer or random copolymer, polyglycolic acid copolylactic acid block or random copolymer, stereoisomers and copolymers of polylactide, poly-L lactide (PLLA), poly-D-lactide (PDLA), poly-DL-lactide (PDLLA), L-lactide, DL-lactide copolymers, L-lactide, D-lactide copolymers, lactide tetramethylene glycolide copolymers, polyhydroxyalkanoate (PHA) homopolymer or copolymer, poly-β-hydroxybutyrate (PHB), poly-4-hydroxybutyrate (P4HB), citric acid polymers, and polyurethanes.

3. The composite according to claim 2, wherein the at least one filament comprises at least one biodegradable or bioabsorbable material selected from the group consisting of silk, resorbable metals, resorbable metal alloys, resorbable ceramics, and phosphate, borate, and silicate soluble glasses.

4. The composite according to claim 3, wherein the at least one filament comprises a surface coating for improving integration of the at least one filament with the degradable matrix.

5. The composite according to claim 1, wherein the reinforcement element core structure comprises a plurality of filaments.

6. The composite according to claim 5, wherein at least some of the plurality of filaments are disposed substantially parallel to one another.

7. The composite according to claim 5, wherein at least some of the plurality of filaments are combined so as to form at least one fiber;
wherein at least some of the plurality of filaments are twisted together so as to form at least one fiber; and
wherein at least some of the plurality of filaments are twisted at a rate of up to 2.0 twists per inch.

8. The composite according to claim 7, wherein the at least one fiber is a plurality of fibers and at least some of the plurality of fibers are disposed substantially parallel to one another.

9. The composite according to claim 7, wherein the plurality of filaments is woven, braided, or both.

10. The composite according to claim 7, wherein the composite is a composite implant; and wherein the at least one fiber is present in an amount of about 5 volume percent to about 75 volume percent of the implant.

11. The composite according to claim 10, wherein the at least one fiber is present in an amount of about 25 volume percent to about 50 volume percent of the implant.

12. The composite according to claim 1, wherein the outer region of the reinforcement element core structure comprises a degradable polymer; and
wherein the degradable polymer comprises biodegradable or bioabsorbable materials selected from the group consisting of polylactic acid homopolymer or copolymer, polycaprolactone, polyglycolide (PGA), glycolide copolymers, glycolide/lactide copolymers (PGA/PLA), and polylactic acid cocaprolactone block copolymer or random copolymer, polyglycolic acid copolylactic acid block or random copolymer, stereoisomers and copolymers of polylactide, poly-L lactide (PLLA), poly-D-lactide (PDLA), poly-DL-lactide (PDLLA), L-lactide, DL-lactide copolymers, L-lactide, D-lactide copolymers, lactide tetramethylene glycolide copolymers, polyhydroxyalkanoate (PHA) homopolymer or copolymer, poly-β-hydroxybutyrate (PHB), poly-4-hydroxybutyrate (P4HB), citric acid polymers, and polyurethanes.

13. The composite according to claim 1, wherein the filament volume of the reinforcement element is greater than the filament volume of the composite.

14. The composite according to claim 1, wherein the core structure comprises a plurality of reinforcement elements embedded in a degradable material.

15. The composite according to claim 14, wherein the degradable material comprises biodegradable or bioabsorbable materials selected from the group consisting of polylactic acid homopolymer or copolymer, polycaprolactone, polyglycolide (PGA), glycolide copolymers, glycolide/lactide copolymers (PGA/PLA), and polylactic acid cocaprolactone block copolymer or random copolymer, polyglycolic acid copolylactic acid block or random copolymer, stereoisomers and copolymers of polylactide, poly-L lactide (PLLA), poly-D-lactide (PDLA), poly-DL-lactide (PDLLA), L-lactide, DL-lactide copolymers, L-lactide, D-lactide copolymers, lactide tetramethylene glycolide copolymers, polyhydroxyalkanoate (PHA) homopolymer or copolymer, poly-β-hydroxybutyrate (PHB), poly-4-hydroxybutyrate (P4HB), citric acid polymers, and polyurethanes.

16. The composite according to claim 14, wherein at least some of the plurality of reinforcement elements extend substantially parallel to one another.

17. The composite according to claim 14, wherein at least some of the filaments of the plurality of reinforcement elements extend substantially parallel to one another.

18. The composite according to claim 1, wherein the outer region formed on the core structure comprises a degradable composition; and
wherein the degradable polymer comprises biodegradable or bioabsorbable materials selected from the group consisting of polylactic acid homopolymer or copolymer, polycaprolactone, polyglycolide (PGA), glycolide copolymers, glycolide/lactide copolymers (PGA/PLA), and polylactic acid cocaprolactone block copolymer or random copolymer, polyglycolic acid copolylactic acid block or random copolymer, stereoisomers and copolymers of polylactide, poly-L lactide (PLLA), poly-D-lactide (PDLA), poly-DL-lactide (PDLLA), L-lactide, DL-lactide copolymers, L-lactide, D-lactide copolymers, lactide tetramethylene glycolide copolymers, polyhydroxyalkanoate (PHA) homopolymer or copolymer, poly-β-hydroxybutyrate (PHB), poly-4-hydroxybutyrate (P4HB), citric acid polymers, and polyurethanes.

19. The composite according to claim 1, wherein the outer region formed on the core structure comprises between 2 and 25 layers.

20. The composite according to claim 19, wherein the layers are characterized by at least one of the group consisting of equal thicknesses and varying thicknesses.

21. The composite according to claim 1, wherein the outer region formed on the core structure comprises an inner layer and an outer layer, wherein the inner layer is thicker than the outer layer.

22. The composite according to claim 1, wherein the outer region formed on the core structure is approximately 351 microns thick or less.

23. The composite according to claim 1, wherein the outer region formed on the core structure provides surface features:
wherein the surface features comprise at least one from the group consisting of barbs and threads.

24. The composite according to claim 1, wherein the outer region formed on the core structure provides a desired porosity.

25. The composite according to claim 1, wherein the outer region comprises a bag.

26. The composite according to claim 1, wherein the composite comprises one of the group consisting of a screw, a rod, a pin, a nail, a bone anchor, bent pin, clip with semielastic properties, and a toggling bone anchor.

27. The composite according to claim 1, wherein a cross-sectional profile of the composite comprises one from the group consisting of round, circular, 3-sided, 4-sided, 6-sided, 8-sided, cruciform, and multi-lobed.

28. The composite according to claim 1, wherein the composite is a composite implant.

29. The composite according to claim 28, the composite comprises a barrier, the barrier being configured to selectively pass water.

30. The composite according to claim 29, wherein the filaments are biodegradable and/or bioabsorbable filaments.

31. The composite according to claim 30, wherein the composite comprises one of the group consisting of a screw, a rod, a pin, a nail, a bone anchor, bent pin, clip with semielastic properties, and a toggling bone anchor.

32. The composite according to claim 31, wherein the rod is cannulated.

33. The composite according to claim 31, wherein the at least one reinforcement element comprises a porogen; and wherein the porogen is in the form of a dissolvable fiber.

34. The composite according to claim 33, wherein the composite includes a pultrusion that includes a rolled reinforcement element sheet or a braided or woven core of reinforcement element.

35. The composite according to claim 28, the implant is constructed so it is capable of starting to degrade within a body in which it is implanted within about 1 month to about 24 months after implantation in the body.

36. The composite according to claim 1, wherein the degradable matrix includes inorganic filler particles present in an amount ranging from about 10 to about 50 wt % of the matrix, and such particles enable the implant to become porous after implantation.

37. The composite according to claim 36, wherein the implant includes at least one reinforcing element that includes a flexible reinforcing rod containing a plurality of the at least one filament held together by an outer sheath.

38. The composite according to claim 1, wherein the at least one reinforcement element includes a rod having a substantially triangular cross-section or a substantially circular cross-section.

39. A composite comprising:
a layered structure, configured to selectively pass water, the layered structure comprising:
(a) a core structure, the core structure comprising:
(i) at least one reinforcement element, the at least one reinforcement element comprising:
(1) a reinforcement element core structure comprising a degradable matrix and at least one filament, wherein the at least one filament is disposed within the degradable matrix; and
(2) an outer region formed on the reinforcement element core structure, wherein the outer region of the reinforcement element core structure comprises at least one layer; and
(b) an outer region formed on the core structure, wherein the outer region of the core structure comprises at least one layer;
wherein the at least one filament comprises between 5% and 65% by volume of the composite.

40. The composite according to claim 39, wherein the at least one filament comprises between 5% and 85% by volume of the reinforcement element.

41. The composite according to claim 39, wherein the composite is a composite implant.

42. The composite according to claim 41, wherein the composite comprises one of the group consisting of a screw, a rod, a pin, a nail, a bone anchor, bent pin, clip with semielastic properties, and a toggling bone anchor.

43. A composite comprising:
a layered structure, configured to selectively pass water, the layered structure comprising:
(a) a core structure, the core structure comprising:
(i) at least one reinforcement element, the at least one reinforcement element comprising:
(1) reinforcement element core structure comprising a degradable matrix and at least one filament, wherein the at least one filament is disposed within the degradable matrix; and
(2) an outer region formed on the reinforcement element core structure, wherein the outer region of the reinforcement element core structure comprises at least one layer; and
(b) an outer region formed on the core structure, wherein the outer region of the core structure comprises at least one layer;
wherein the degradable matrix comprises a polylactic acid homopolymer or copolymer, a polycaprolactone, a polyglycolide (PGA), a glycolide copolymers, a glycolide/lactide copolymers (PGA/PLA), a polylactic acid cocaprolactone block copolymer or random copolymer, a polyglycolic acid copolylactic acid block or random copolymer, a stereoisomers or copolymer of polylactide, a poly-L lactide (PLLA), a poly-D-lactide (PDLA), a poly-DL-lactide (PDLLA), a L-lactide, a DL-lactide copolymer, a D-lactide copolymer, a lactide tetramethylene glycolide copolymer, a polyhydroxyalkanoate (PHA) homopolymer or copolymer, poly-β-hydroxybutyrate (PHB), a poly-4-hydroxybutyrate (P4HB), a citric acid polymer, or a polyurethane;
wherein the reinforcement element core structure comprises a plurality of filaments;
wherein at least some of the plurality of filaments are twisted together at a rate of up to 2.0 twists per inch so as to form at least one fiber;
wherein at least some of the plurality of fibers are disposed substantially parallel to one another and at least some of the plurality of fibers are disposed substantially transverse to one another;
wherein the outer region of the reinforcement element core structure comprising comprises a polylactic acid homopolymer or copolymer, a polycaprolactone, a polyglycolide (PGA), a glycolide copolymers, a glycolide/lactide copolymers (PGA/PLA), a polylactic acid cocaprolactone block copolymer or random copolymer, a polyglycolic acid copolylactic acid block or random copolymer, a stereoisomers or copolymer of polylactide, a poly-L lactide (PLLA), a poly-D-lactide (PDLA), a poly-DL-lactide (PDLLA), a L-lactide, a DL-lactide copolymer, a D-lactide copolymer, a lactide tetramethylene glycolide copolymer, a polyhydroxyalkanoate (PHA) homopolymer or copolymer, a poly-β-hydroxybutyrate (PHB), a poly-4-hydroxybutyrate (P4HB), a citric acid polymer, or a polyurethane;

wherein the at least one filament comprises between 5% and 85% by volume of the reinforcement element, and the filament volume of the reinforcement element is greater than the filament volume of the composite;

wherein the surface features comprise at least one from the group consisting of barbs and threads; and wherein the outer region formed on the core structure provides a desired porosity.

44. The composite according to claim 43, wherein the composite is a composite implant.

45. The composite according to claim 44, wherein the composite comprises one of the group consisting of a screw, a rod, a pin, a nail, a bone anchor, bent pin, clip with semielastic properties, and a toggling bone anchor.

* * * * *